US010561707B2

(12) United States Patent
Toledano et al.

(10) Patent No.: US 10,561,707 B2
(45) Date of Patent: Feb. 18, 2020

(54) SEMAPHORIN 3C VARIANTS, COMPOSITIONS COMPRISING SAID VARIANTS AND METHODS OF USE THEREOF IN TREATING EYE DISEASES

(71) Applicants: Technion Research & Development Foundation Limited, Haifa (IL); Rambam Med-Tech Ltd., Haifa (IL)

(72) Inventors: Shira Toledano, Haifa (IL); Ofra Kessler, Haifa (IL); Gera Neufeld, Haifa (IL); Yoreh Barak, Moshav Yodfat (IL); Yelena Mumblat, Haifa (IL)

(73) Assignees: TECHNION RESEARCH AND DEVELOPMENT FOUNDATION LTD., Haifa (IL); RAMBAM MED-TECH LTD., Haifa (IL)

( * ) Notice: Subject to any disclaimer, the term of this patent is extended or adjusted under 35 U.S.C. 154(b) by 0 days.

(21) Appl. No.: 15/413,991

(22) Filed: Jan. 24, 2017

(65) Prior Publication Data
US 2017/0173111 A1 Jun. 22, 2017

Related U.S. Application Data

(63) Continuation-in-part of application No. 14/917,152, filed as application No. PCT/IL2014/050797 on Sep. 7, 2014, now Pat. No. 9,896,490.

(60) Provisional application No. 62/286,488, filed on Jan. 25, 2016, provisional application No. 61/875,060, filed on Sep. 8, 2013.

(51) Int. Cl.
*A61K 38/17* (2006.01)
*A61K 9/00* (2006.01)
*A61K 45/06* (2006.01)

(52) U.S. Cl.
CPC ........ *A61K 38/1709* (2013.01); *A61K 9/0048* (2013.01); *A61K 45/06* (2013.01)

(58) Field of Classification Search
CPC ................................................ A61K 38/1709
See application file for complete search history.

(56) References Cited

U.S. PATENT DOCUMENTS

| 8,088,735 | B2 * | 1/2012 | Neufeld | A61K 38/1709 |
| | | | | 514/1.1 |
| 8,513,194 | B2 * | 8/2013 | Neufeld | A61K 38/1709 |
| | | | | 514/1.1 |
| 8,808,693 | B2 | 8/2014 | Ong et al. | |
| 2008/0153819 | A1 * | 6/2008 | Bingaman | A61K 31/416 |
| | | | | 514/233.8 |
| 2008/0261956 | A1 * | 10/2008 | Choi | C07D 209/08 |
| | | | | 514/218 |
| 2009/0042866 | A1 * | 2/2009 | Lennox | C07D 209/08 |
| | | | | 514/219 |
| 2010/0222401 | A1 * | 9/2010 | Li | A61K 38/1709 |
| | | | | 514/384 |
| 2012/0101029 | A1 * | 4/2012 | Neufeld | A61K 38/1709 |
| | | | | 514/1.9 |
| 2013/0028896 | A1 | 1/2013 | Ong et al. | |
| 2013/0122006 | A1 * | 5/2013 | Le Bouteiller | C07K 16/22 |
| | | | | 424/135.1 |
| 2013/0287726 | A1 | 10/2013 | Neufeld et al. | |

FOREIGN PATENT DOCUMENTS

| WO | WO2010/11792 | 10/2010 |
| WO | WO2011/127519 | 10/2011 |
| WO | WO2015/033345 | 3/2015 |
| WO | WO2016/159652 | 10/2015 |

OTHER PUBLICATIONS

Tao et al., 2010, Intravireal Bevacizumab Combined with Intravitreal Trimcinolone for Therapy-Resistant Exudative Age-Related Macular Degeneration, Journal of Ocular Pharmacology and Therapeutics, 26(2): 207-211.*
Mumblat et al., 2015, Full-Length Semaphorin-3C is an Inhibitor of Tumor Lymphangiogenesis and Metastasis, Cancer Research, 75(11):2177-2186.*
Herman et al., 2007, Increased class 3 semaphorin expression modulates the invasive and adhesive properties of prostate cancer cells, International Journal of Oncology, 30: 1231-1238.*
Neufeld et al., 2005, Semaphorins in Cancer, Frontiers in Bioscience, 10: 751-760.*
Banu et al., 2006, Semaphorin 3C regulates endothelial cell function by increasing integrin activity, The FASEB Journal, 20: E1520-E1527.*
Miyato et al., 2012, Semaphorin 3C is involved in the progression of gastric cancer, Cancer Sci, 103(11): 1961-1966.*
Neufeld et al., "The semaphorins: versatile regulators of tumour progression and tumour angiogenesis", Nat. Rev. Cancer, Jun. 26, 2008, vol. 8, pp. 632-645.
Miyato, H. et al., "Semaphorin 3C is involved in the progression of gastric cancer", Cancer Sci., Aug. 24, 2012, vol. 103, No. 11, pp. 1961-1966.
Becker et al., "Potent Inhibitors of Furin and Furin-like Proprotein Convertases Containing Decarboxylated P1 Arginine Mimetics", J. Med. Chem. 2010, Dec. 28, 2009, vol. 53, No. 3, pp. 1067-1075.
Seidah N.G. et al., "The biology and therapeutic targeting of the proprotein convertases", Nat Rev. Drug. Discov., May 2012, vol. 11, pp. 367-383.
Varshavsky et al. "Semaphorin-3B is an Angiogenesis Inhibitor That is Inactivated by Furin-Like Pro-Protein Convertases", Cancer Res., Sep. 1, 2008, vol. 68, No. 17, pp. 6922-6931.

(Continued)

Primary Examiner — Amber D Steele
(74) Attorney, Agent, or Firm — Pearl Cohen Zedek Latzer Baratz LLP

(57) ABSTRACT

The present invention relates, according to some embodiments, method of treating eye diseases, such as AMD by administering Semaphorin 3C (Sema3C) or a variant thereof having amino acid modifications at furin-like pro-protein convertase cleavage sites, rendering these sites resistant to cleavage.

20 Claims, 36 Drawing Sheets

Specification includes a Sequence Listing.

(56) References Cited

OTHER PUBLICATIONS

Casazza et al., "Tumour growth inhibition and anti-metastatic activity of a mutated furin-resistant Semaphorin 3E isoform", EMBO Mol. Med., Mar. 8, 2012, vol. 4, No. 1-17, pp. 234-250.
Kontermann, "Strategies for extended serum half-life of protein therapeutics", Biotechnology, Aug. 20, 2011, vol. 22 pp. 868-876.
Herman et al. "Increased class 3 semaphorin expression modulates the invasive and adhesive properties of prostate cancer cells". International Journal of Oncology. May 2007, vol. 30, No. 5. pp. 1231-1238.
Hideyo et al. "Semaphorin 3C is involved in the progression of gastric cancer." Cancer Science. Nov. 15, 2012, vol. 103, No. 11, pp. 1961-1966.
Casazza et al., "Tumor growth inhibition and anti-metastatic activity of isoform" EMBO Molecular Medicine. Mar. 13, 2012, vol. 4, No. 3, pp. 234-250.
N. Banu "Semaphorin 3C regulates endothelial cell function by increasing intergrin activity" The FASEB Journal. Oct. 1, 2006, vol. 20 No. 12. pp. 2150-2152.
Tina Dietrich et al. "Inhibition of Inflammatory Lymphangiogenesis by Intergrin [alpha]5 Blockade" The American Journal of Pathology. Jul. 1, 2007, vol. 171 No. 1 pp. 361-372.
Esselens et al. "The Cleavage of Semaphorin 3C Induced by ADAMTS1 Promotes Cell Migration" Journal of Biological Chemistry. Nov. 13, 2009, vol. 285 No. 4. pp. 2463-2473.
Atsuko Sakurai et al. "Semaphorin signaling in angiogenesis, lymphangiogenesis and cancer" Cell Research. Jan. 1, 2012, vol. 22 No. 1. pp. 23-32.
International Search Report for International App. No. PCT/IL2014/050797 dated Jan. 9, 2015.
Barak et al. "A Sema3E mutant resistant to cleavage by furins (UNCL-SEMA3E E) inhibits laser induced Choroidal Neovasculizarisation" Investigative Ophthalmology & Visual Science, May 3, 2015;56(7):2362-2362.
Buehler et al. "Semaphorin 3F forms an anti-angiogenic barrier in outer retina" FEBS Lett. Jun. 5, 2013;587(11):1650-5.
European Search Report of EP 17743846 dated Jul. 18, 2019.
International Search Report of PCT/IL2017/050093 dated Jun. 2, 2017.
Mumblat et al. "Full-Length Semaphorin-3C is an Inhibitor of Tumor Lymphangiogenesis and Metastasis" Cancer Res. Jun. 1, 2015;75(11):2177-86.
Toledano et al. "A SEMA3E mutant resistant to cleavage by furins (UNCL-SEMA3E) inhibits choroidal neovascularization" Exp Eye Res. Dec. 2016;153:186-194.
Toledano et al. "A Sema3C Mutant Resistant to Cleavage by Furin (FR-Sema3C) Inhibits Choroidal Neovascularization" PLoS One. Dec. 30, 2016;11(12):e0168122.
Toledano et al. "Semaphorin-3C Resistant to Cleavage by Furins Inhibits Choroidal Neovascularization" ARVO 2016, Annual Meeting Abstracts, May 4, 2016.
Yang et al. "Semaphorin-3C signals through Neuropilin-1 and PlexinD1 receptors to inhibit pathological angiogenesis" EMBO Mol Med. Oct. 2015;7(10):1267-84.

* cited by examiner

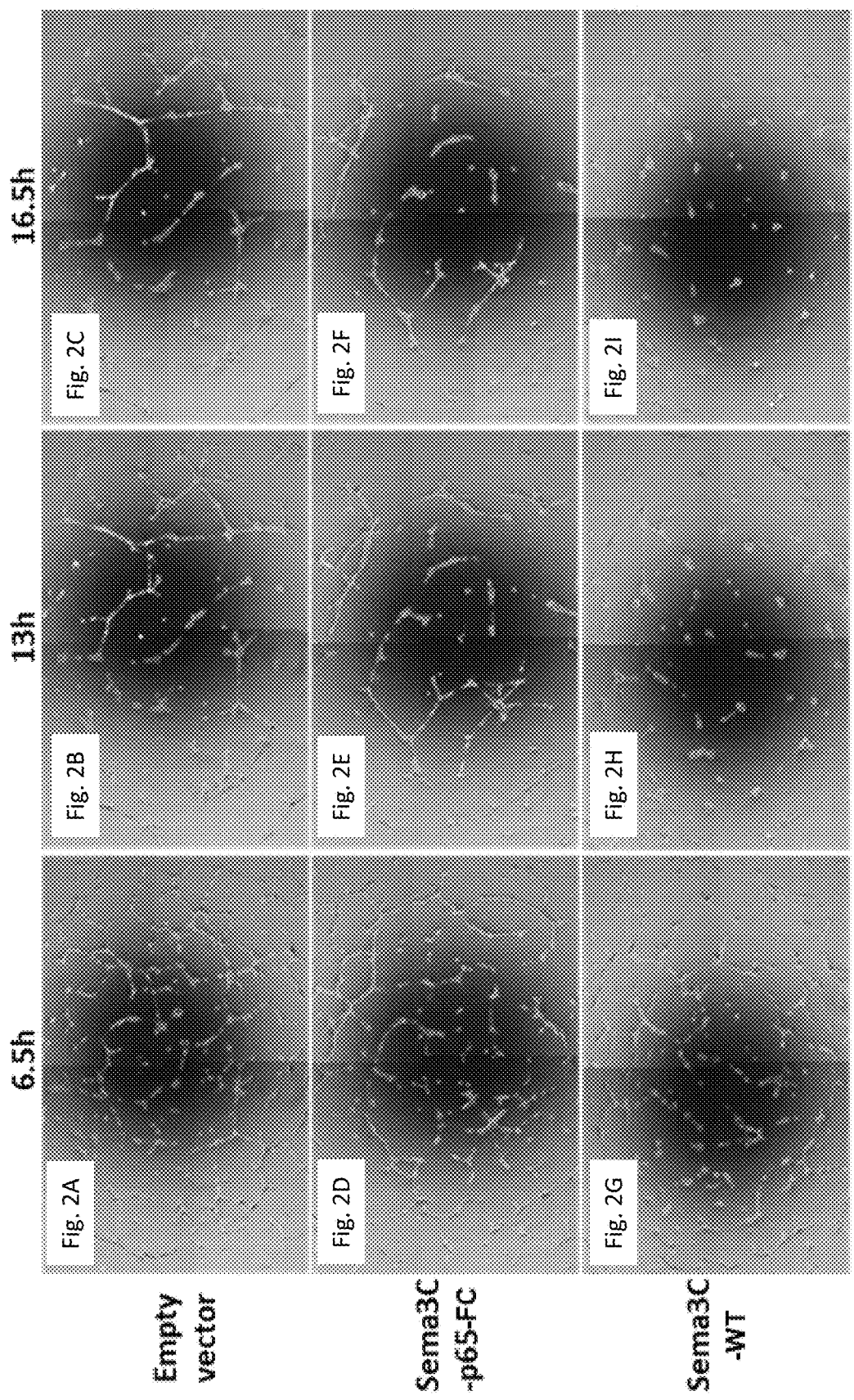

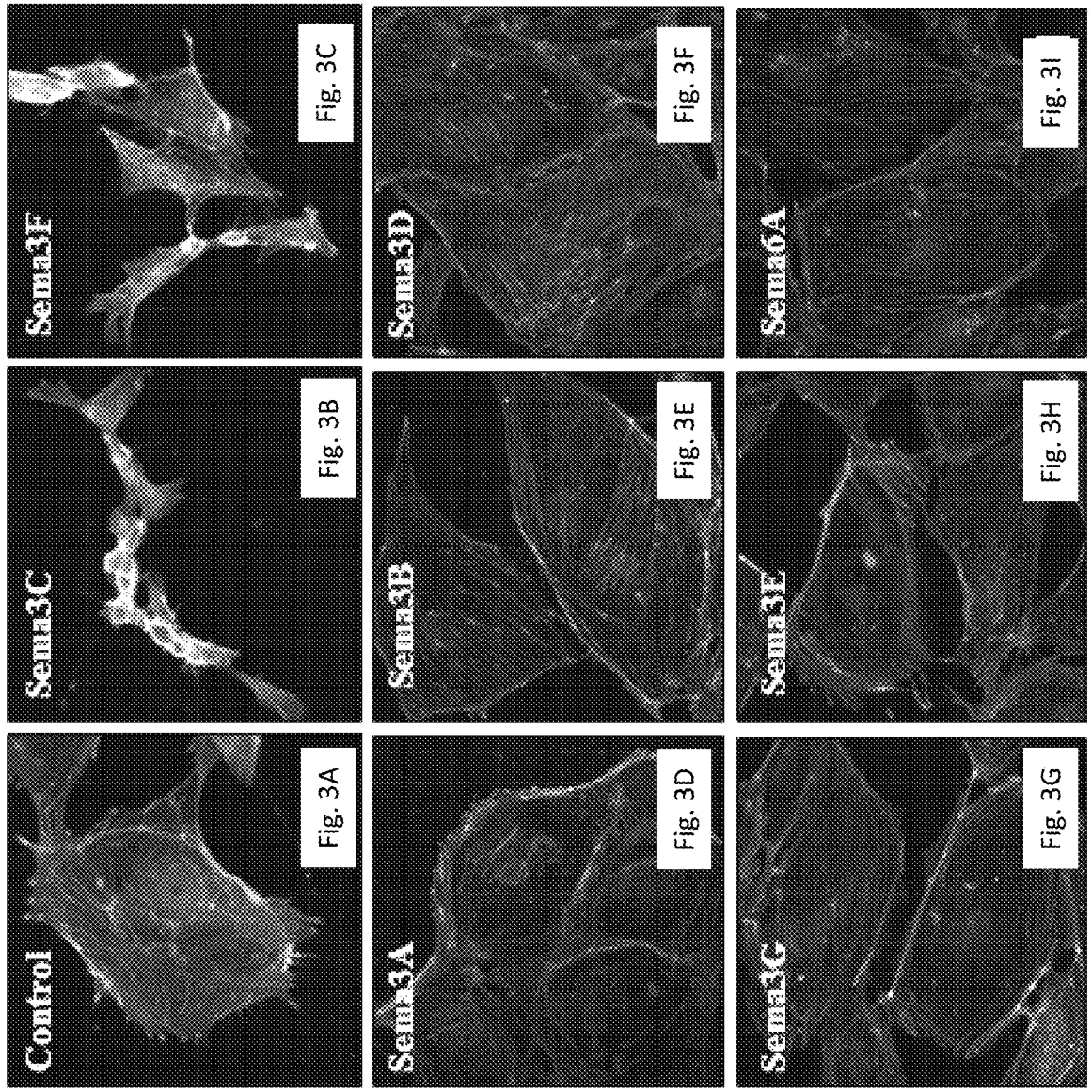

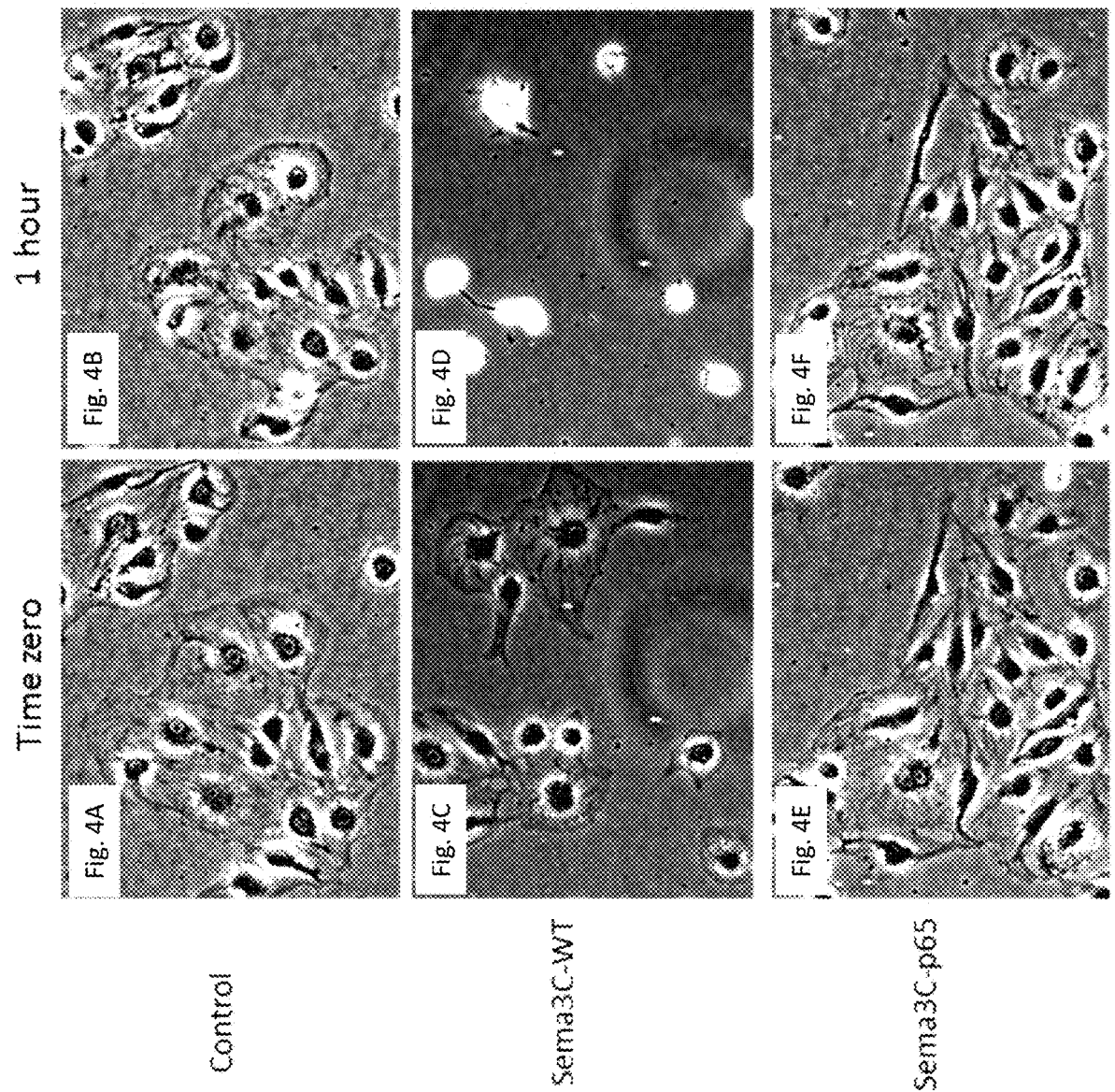

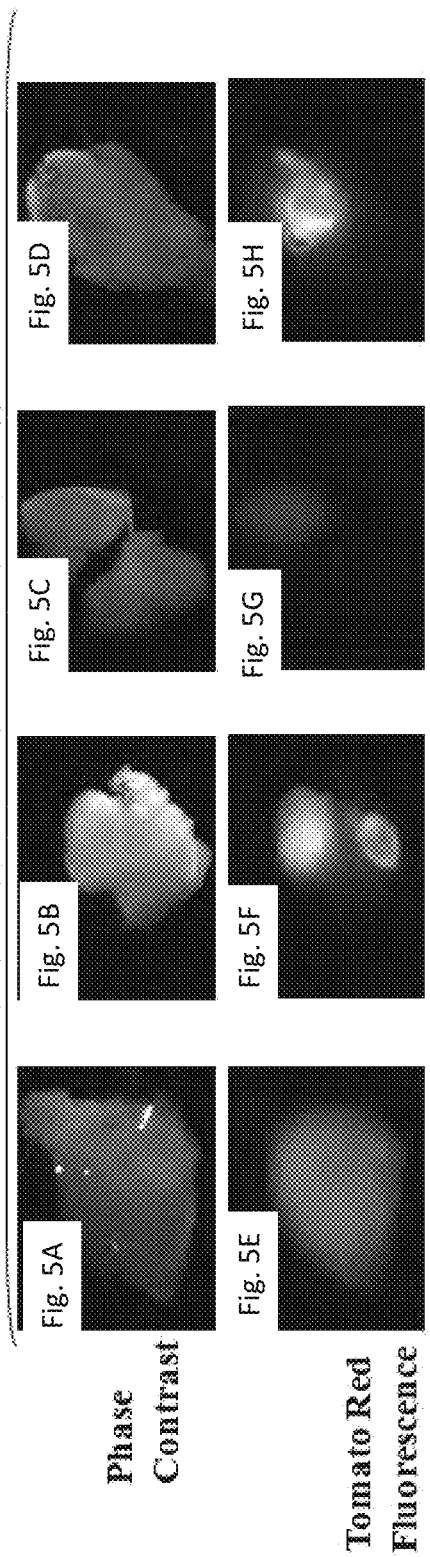
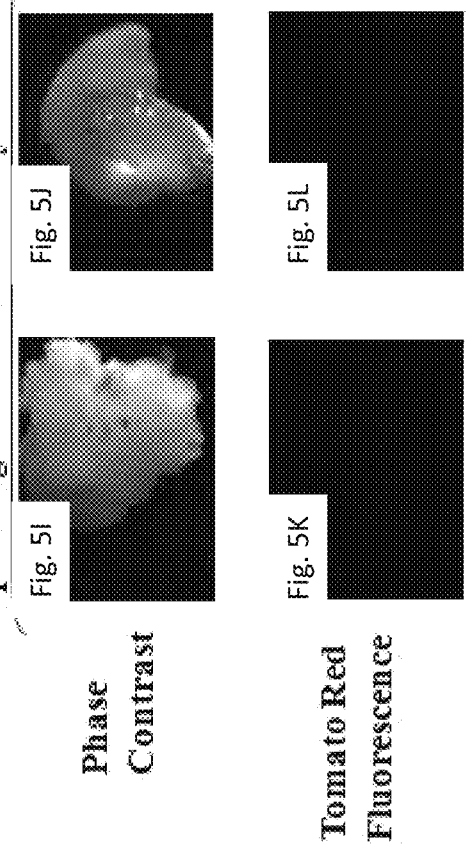
Fig. 4A ited sentinel lymph nodes adjacent to LM2-4 derived tumors from four control mice
Isolated sentinel lymph nodes adjacent to LM2-4 derived tumors expressing UNCL-sema3C/myc from two mice

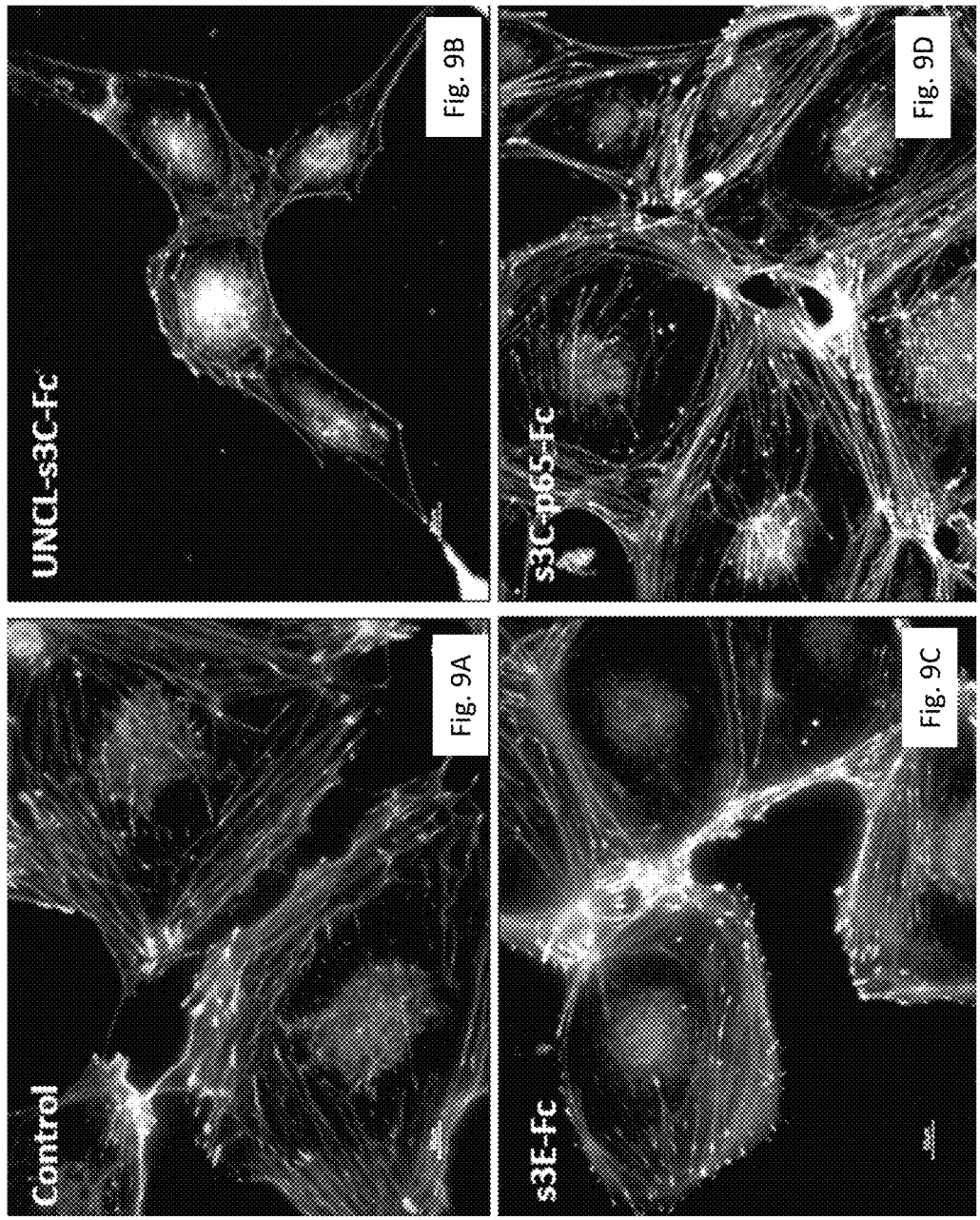

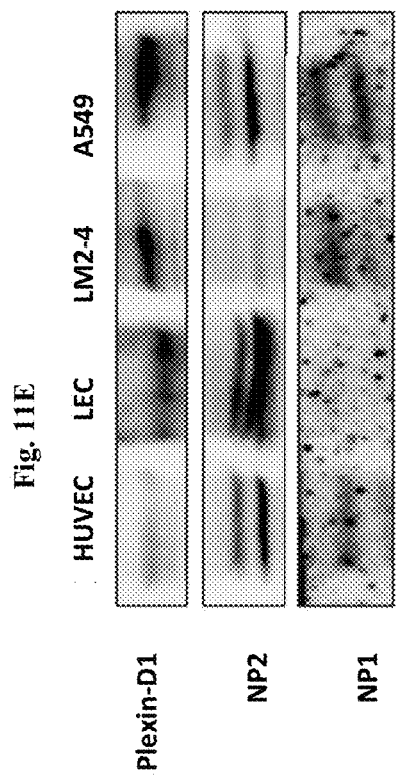

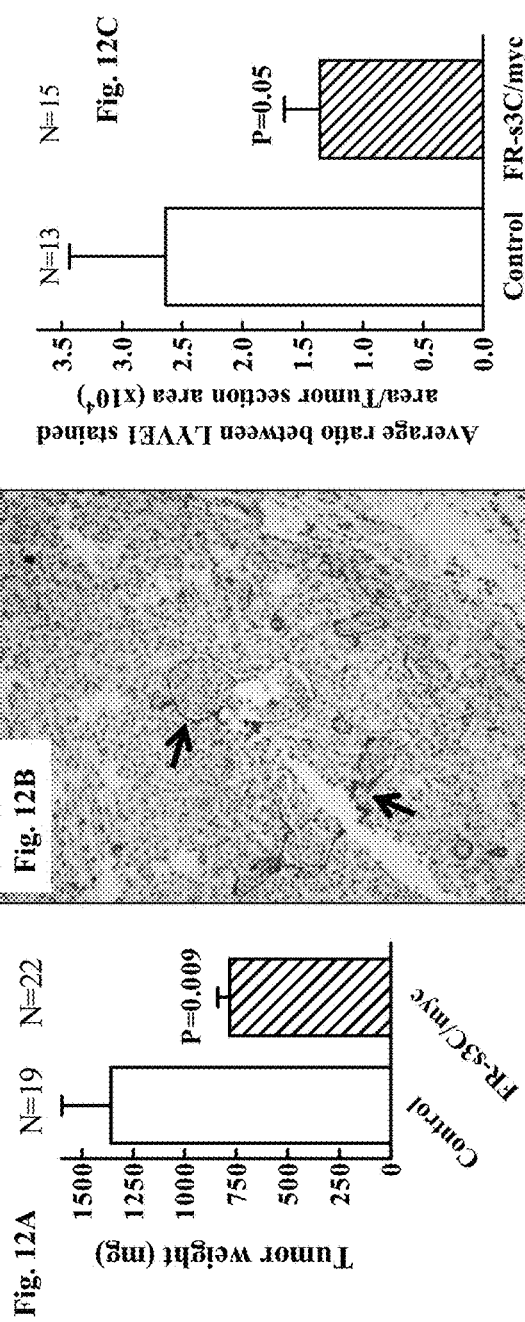
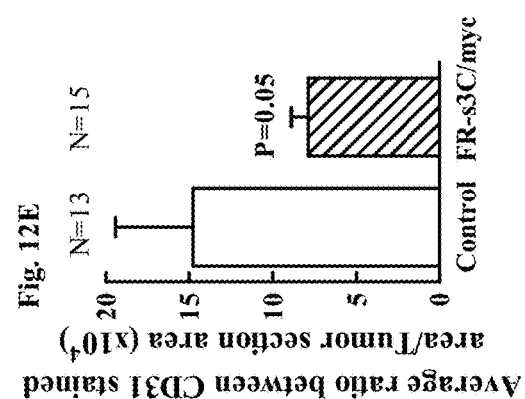
Fig. 12A, Fig. 12B, Fig. 12C, Fig. 12D, Fig. 12E

Fig. 13B
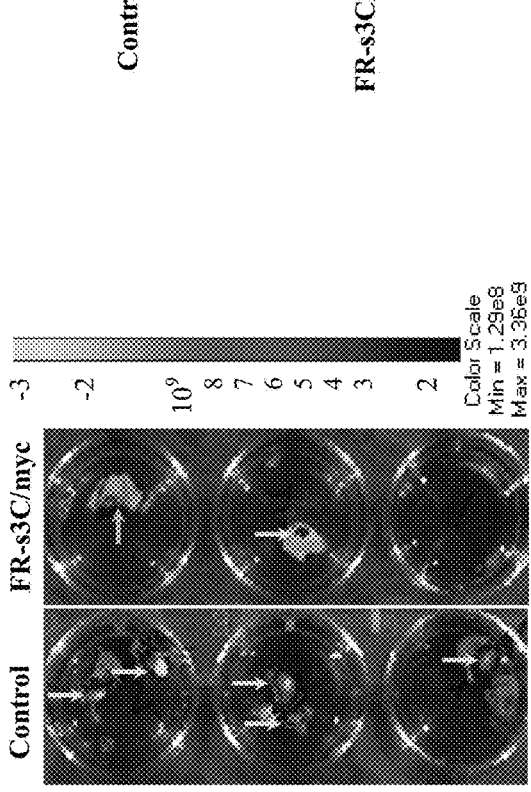
Fig. 13D
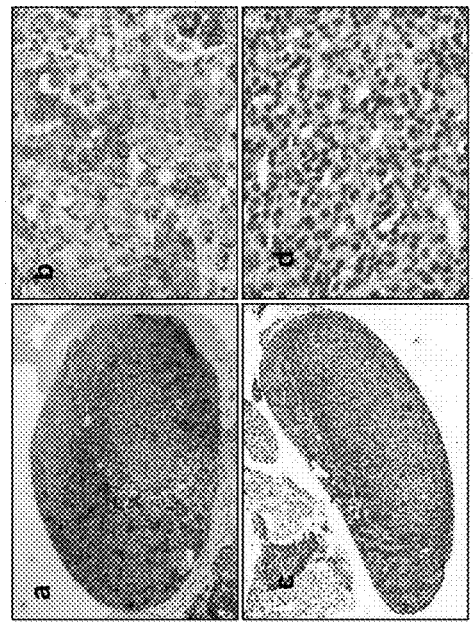
Fig. 13A
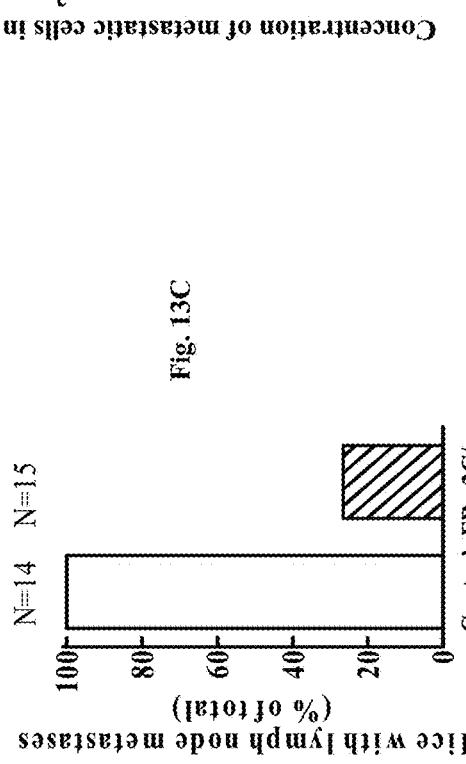
Fig. 13C

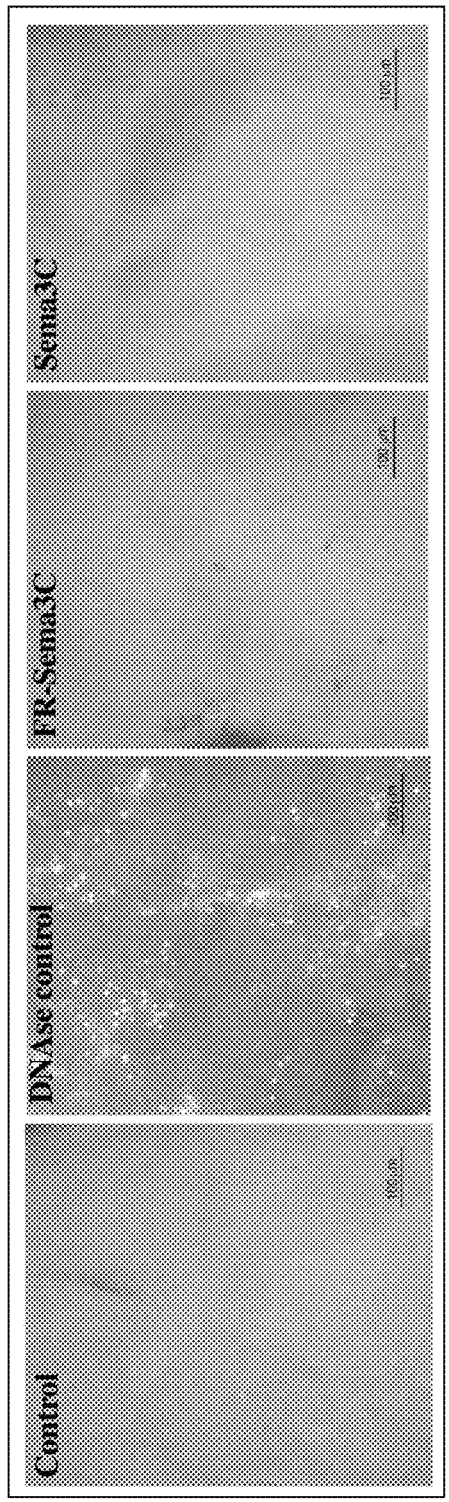
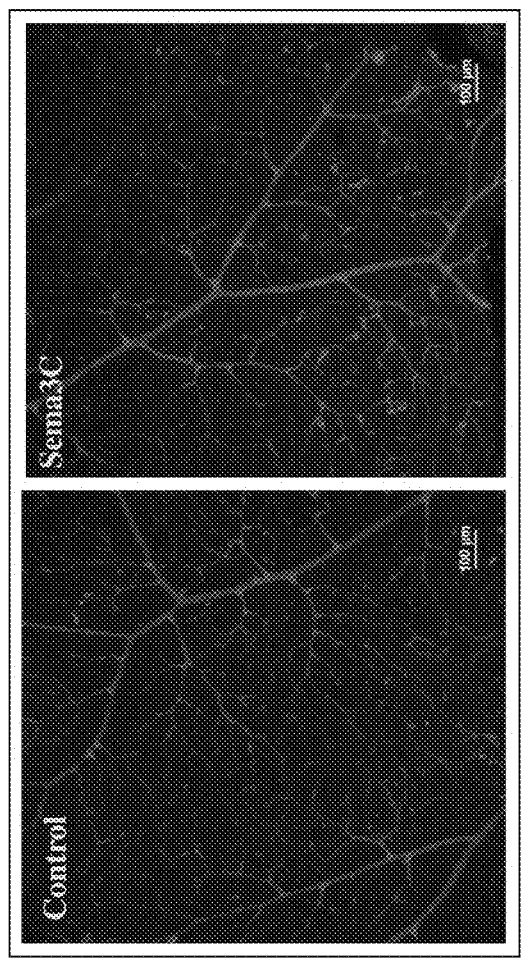
Fig. 20A
Fig. 20B

SEMAPHORIN 3C VARIANTS, COMPOSITIONS COMPRISING SAID VARIANTS AND METHODS OF USE THEREOF IN TREATING EYE DISEASES

CROSS REFERENCE TO RELATED APPLICATIONS

This application is a continuation-in-part of U.S. application Ser. No. 14/917,152, filed Mar. 7, 2016, now U.S. Pat. No. 9,896,490, which is a National Phase Application of PCT International Application No. PCT/IL2014/050797, International Filing Date Sep. 7, 2014, entitled "SEMAPHORIN 3C VARIANTS, COMPOSITIONS COMPRISING SAID VARIANTS AND METHODS OF USE THEREOF", published on Mar. 12, 2015 as International Publication No. WO 2015/033345, claiming the benefit of U.S. Provisional Patent Application No. 61/875,060, filed Sep. 8, 2013, all of which are hereby incorporated in their entirety.

This application also claims the benefit of U.S. Provisional Application No. 62/286,488, filed on Jan. 25, 2016 and entitled SEMA3C MUTANT RESISTANT TO CLEAVAGE BY FURINS (FR-SEMA3C) INHIBITS LASER-INDUCED CHOROIDAL NEOVASCULARIZATION, which is hereby incorporated in its entirety.

FIELD OF THE INVENTION

The present invention relates, inter alia, to variants of Semaphorin 3C (Sema3C) having amino acid modifications at furin-like pro-protein convertase cleavage sites, rendering these sites resistant to cleavage and methods of using same for treatment of eye diseases.

BACKGROUND OF THE INVENTION

Semaphorins are a family of membrane bound and soluble proteins classified into eight sub-classes based on their structural domains Semaphorins mainly regulate focal adhesion assembly/disassembly and induce cytoskeletal remodeling, thus affecting cell shape, cell attachment to the extracellular matrix, cell motility, and cell migration. Although originally identified as axon guidance factors that control the development of central nervous system, different Semaphorins have been shown to participate in many other processes, such as immune response, angiogenesis and lymphangiogenesis.

The seven class-3 Semaphorins (Sema3s), designated by the letters A-G, are the only vertebrate secreted Semaphorins. Neuropilins (Nrps) and the type A/D family Plexins (Plexin-A1, -A2, and -A3, and Plexin-D1) act as receptors for Sema3s. Each Sema3 family member shows distinct binding preference for Nrps. Each Sema3-Nrp complex associates with specific plexins to mediate downstream signaling.

Semaphorin 3C (Sema3C), a class-3 Semaphorin, is known to affect neuronal migration, such as by providing chemorepulsive cues to sympathetic neurons or chemoattractive cues to GABAergic neurons. In addition to its role as affecting neuronal migration, Sema3C has been shown to have additional functions. As opposed to most class-3 Semaphorins, found to function as inhibitors of endothelial cell migration and proliferation and as inhibitors of angiogenesis (Neufeld et al., 2008, Nat. Rev. Cancer, 8: 632-645), several studies indicate that Sema3C plays a distinct role in promoting angiogenesis, endothelial cell guidance and vascular morphogenesis. For example, Sema3C has been shown to induce proliferation and adhesion of mouse glomerular endothelial cells (MGEC). Additionally, Sema3C has been shown to induce an increase in MGEC directional migration and to stimulate MGEC capillary-like network formation on Collagen I gels (Banu N. et al., 2006, FASEB J., 20:2150-2152).

Sema3C has also been suggested to be involved in tumor progression, to promote tumor migration and to be highly expressed in metastatic tumor cells. For example, Sema3C was shown to be highly expressed in neoplastic cells of gastric cancer. Additionally, primary stomach tumors, as well as metastatic liver tumors, were significantly suppressed by Sema3C miRNA-induced silencing in nude mice (Miyato, H. et al., 2012, Cancer Sci., 103: 1961-1966).

The seven class-3 Semaphorins contain conserved furin like pro-protein convertases (FPPC) cleavage sites. The functional activity of class-3 Semaphorins is subject to regulation by cleavage at the FPPC cleavage sites. Furin like pro-protein convertases (FPPC) are a family of proteolytic enzymes which convert proteins from their inactive immature form to their active form through cleavage of the immature proteins at FPPC cleavage sites. Furin and six other members of this family (PC2, PC1/3, PACE4, PC4, PC5/6, and PC7) possess a strong preference for substrates containing the multi-basic cleavage motif Arg-X-Arg/Lys-Arg-X (Becker et al., 2010, J. Med. Chem., 53(3):1067-1075). Furin and its analogues are responsible for the maturation of a large number of inactive protein precursors and are thus involved in many normal physiological processes. Expression of FPPC is often upregulated in tumors and metastases (Seidah N. G. et al., 2012, Nat. Rev. Drug. Discov., 11:367-383).

In some cases, cleavage of class-3 Semaphorins at FPPC cleavage sites was found to result in the complete inhibition of biological activity, as in the case of Sema3B (Varshaysky et al., 2008, Cancer Res., 68:6922-6931). In another case, cleavage at FPPC cleavage sites of Sema3E was found to result in Sema3E's pro-metastatic activity. The proteolytic processing of Sema3E was found to have no role in regulating its inhibitory activity towards endothelial cells (Casazza et al., 2012, EMBO Mol. Med., 4:234-250).

Sema3C comprises conserved FPPC cleavage sites and further comprises a cleavage site for the ADAMTS1 extracellular metalloprotease. Naturally occurring Sema3C is present as a mixture of the FPPC-cleaved and non-cleaved forms. Cleavage of Semaphorin 3C induced by ADAMTS1 has been shown to promote in-vitro cell migration (Esselens C. et al., 2009, J. Biol. Chem., 285: 2463-2473). However, the functional properties of the various FPPC-cleaved and un-cleaved forms of Sema3C have not been characterized.

U.S. Patent Application Publication No. US2013/0028896 discloses methods, uses and pharmaceutical compositions for treatment of prostate cancer using a Sema 3C inhibitor that may be selected may from: an antibody, a Sema 3C peptide, an antisense RNA, a siRNA, a shRNA or a small molecule.

U.S. Patent Application Publication No. US2012/0101029 by some of the inventors of the present invention discloses a method of treating cancer in a subject in need thereof comprising administering to the subject a therapeutically effective amount of a pro-protein convertase resistant Semaphorin 3E.

Age-related macular degeneration (AMD) is the leading cause of blindness in elderly patients in developed countries. Although both forms of AMD (geographic atrophy or dry AMD and choroidal neovascularization or exudative AMD)

affect central vision, the exudative form poses the greatest risk for severe visual loss. The exudative form is relatively fast progressing and is characterized by choroidal neovascularization (CNV), a process in which new leaky blood vessels originating in the choroid invade the retina. Among the angiogenic factors investigated, VEGF-A was found to be a key factor in animal models, and human wet AMD patients. Although additional angiogenic factors such as basic fibroblast growth factor (bFGF), platelet derived growth factor (PDGF) and hepatocyte growth factor (HGF) play a role as well. VEGF-A inhibitors such as ranibizumab (Lucentis™) or aflibercept (Eylea™) have proven to be effective in treating exudative AMD in the clinic and represent the current mainstay therapeutic treatment. The magnitude of non-response to treatment, defined as no improvement in visual acuity or in reading ability, is evident from recently published large clinical prospective randomized trials. In the Comparison of Age-Related Macular Degeneration Treatments Trial (CATT), more than 12% of patients lost more than 5 letters and more than 30% of patients experienced no significant change or suffered deterioration in visual acuity despite intensive and regular intra-vitreal injections of either bevacizumab or ranibizumab. Similarly, in the ANCHOR study, 22% of patients treated with monthly ranibizumab injections experienced no significant change or suffered deterioration in visual acuity Smaller prospective studies concluded that 45% of patients treated with intravitreal bevacizumab were non-responders. Furthermore, patients treated repetitively with anti-VEGF medication may be prone to develop geographic macular atrophy. There are also indications suggesting that patients develop resistance to treatment over time. Thus, novel therapeutics based on non-VEGF targeted mechanisms are required for a more effective treatment of this disease.

SUMMARY OF THE INVENTION

The present invention relates to variants of Semaphorin 3C (Sema 3C) comprising modifications in furin-like pro-protein convertase (FPPC) cleavage sites, such that the modifications render the sites resistant to cleavage. The present invention further provides, according to some embodiments, methods of inhibiting or suppressing lymphangiogenesis and/or angiogenesis in an eye of a subject in need by administering into the eye of a subject a composition comprising the Semaphorin 3C variants of the invention including for example, FR-sema3C, as set forth in SEQ. ID 8 and/or wild-type Semaphorin 3C. Each possibility represents a separate embodiment of the present invention.

In an embodiment of the invention, the invention provides Semaphorin 3C variants of the invention and/or wild-type Semaphorin 3C for use in inhibiting or suppressing lymphangiogenesis and/or angiogenesis. The invention further relates to the Semaphorin 3C variants of the invention and/or wild-type Semaphorin 3C for use in treating eye disease, such as, but not limited, AMD or other retinal disease.

As used herein, the terms "the Semaphorin 3C variants of the invention", "Semaphorin 3C variants", "the variants of the invention" and "the variants" are used interchangeably. As used herein, the terms "Semaphorin 3C" and "Sema 3C" are used interchangeably.

According to an aspect of the invention "wild-type Semaphorin 3C" encompass also Semaphorin 3C which has at least 80%, 90%, 95%, 99% or 100% sequence identity with the amino acid set forth in SEQ ID NO: 1.

According to one aspect, the present invention provides a variant of Semaphorin 3C which has at least 80%, 90%, 95%, 99% or 100% sequence identity with the amino acid set forth in SEQ ID NO: 1, wherein the variant comprises at least one modification in furin-like pro-protein convertase (FPPC) cleavage site 2 consisting of amino acid residues 549-552; and wherein the modification renders the variant resistant to cleavage at the cleavage site 2.

According to another aspect, there is provided a variant of Semaphorin 3C which has at least 80%, 90%, 95%, 99% or 100% sequence identity with the amino acid set forth in SEQ ID NO: 1, wherein the variant has at least one modification in furin-like pro-protein convertase cleavage site 3 consisting of amino acid residues 742-745; and wherein the modification renders said variant resistant to cleavage at the cleavage site 3.

According to another aspect, the present invention provides a variant of Semaphorin 3C Semaphorin 3C which has at least 80%, 90%, 95%, 99% or 100% sequence identity with the amino acid set forth in SEQ ID NO: 1, wherein the variant comprises at least one modification in furin-like pro-protein convertase (FPPC) cleavage site 2 consisting of amino acid residues 549-552 and at least one modification in furin-like pro-protein convertase cleavage site 3 consisting of amino acid residues 742-745; and wherein the modifications render the variant resistant to cleavage at the cleavage site 2 and at the cleavage site 3.

According to one aspect, the present invention provides a variant of Semaphorin 3C as set forth in SEQ ID NO: 1, wherein the variant (also termed herein "the variant of the invention") comprises at least one modification in furin-like pro-protein convertase (FPPC) cleavage site 2 consisting of amino acid residues 549-552; and wherein the modification renders said variant resistant to cleavage at said cleavage site 2.

According to some embodiments, a modification which renders an FPPC cleavage site resistant to cleavage prevents cleavage of at least 80% of Sema3C variants harboring the modification, possibly at least 90% of said variants, alternatively at least 95% of said variants as compared to cleavage of wild-type Sema3C. Each possibility represents a separate embodiment of the present invention. As used herein, the phrases "a modification which renders a variant resistant to cleavage" and "a modification which prevents a variant from being cleaved" are used interchangeably. As used herein, an un-cleavable variant refers to a variant resistant to cleavage at a furin-like pro-protein convertase cleavage site. According to some embodiments, a Sema3C variant which is un-cleavable due to a modification rendering an FPPC cleavage site resistant to cleavage retains residual cleavage. According to some embodiments, residual cleavage is cleavage of the variant of the invention to a degree of up to 30%, possibly up to 20%, possibly up to 10%, alternatively up to 5% of as compared to the cleavage of wild-type Sema3C. Each possibility represents a separate embodiment of the present invention. According to some embodiments, residual cleavage is cleavage of less than 50%, possibly less than 40%, alternatively less than 30%, typically less than 20% of the variant of the invention. Each possibility represents a separate embodiment of the present invention. According to some embodiments, the variant of the invention comprises at least one modification in furin-like pro-protein convertase cleavage site 3 consisting of amino acid residues 742-745 of Sema3C as set forth in SEQ ID NO: 1; wherein the modification renders the variant resistant to cleavage at the cleavage site.

According to some embodiments, the modification is selected from the group consisting of: at least one amino-acid substitution, at least one amino-acid deletion and a combination thereof. Each possibility represents a separate embodiment of the present invention. According to some embodiments, the modification is an amino-acid deletion comprising at least part of the amino acids within the furin-like pro-protein convertase cleavage site. According to some embodiments, the modification is a modification of at least one Arginine residue within a furin-like pro-protein convertase cleavage site. According to some embodiments, the modification is a modification of at least one Arginine residue within a furin-like pro-protein convertase cleavage site to a Lysine residue. According to other embodiments, the modification is a modification of all Arginine residues within a furin-like pro-protein convertase cleavage site.

According to some embodiments, the variant of the invention comprises at least one modification in furin-like pro-protein convertase cleavage site 2 consisting of amino acid residues 549-552 of Sema3C as set forth in SEQ ID NO: 1 and at least one modification in furin-like pro-protein convertase cleavage site 3 consisting of amino acid residues 742-745 of Sema3C as set forth in SEQ ID NO: 1; wherein the modifications render the variant resistant to cleavage at the cleavage sites. According to some embodiments, the at least one modification in cleavage site 2 is a modification from the sequence RSRR as set forth in SEQ ID NO: 3 to the sequence KSKK as set forth in SEQ ID NO: 13. According to some embodiments, the at least one modification in cleavage site 3 is a truncation of at least part of the C-terminus of said variant as set forth in SEQ ID NO: 34. According to some embodiments, the at least one modification in cleavage site 3 is a truncation of the entire C-terminus of said variant as set forth in SEQ ID NO: 34. According to some embodiments, the variant of the invention is a variant of Semaphorin 3C as set forth in SEQ ID NO: 1, wherein the variant comprises a modification at furin-like pro-protein convertase (FPPC) cleavage site 2 as set forth in SEQ ID NO: 13 and a truncation of the C-terminus section of said variant as set forth in SEQ ID NO: 34. According to some embodiments, the variant of the invention further comprises at least one modification in a basic domain of said variant, the basic domain having an amino acid sequence as set forth in SEQ ID NO: 5. As used herein, the basic domain of Sema3C as set forth in SEQ ID NO: 5 consists of amino acids 724-745 of Sema3C as set forth in SEQ ID NO: 1.

According to some embodiments, the variant of the invention comprises at least one modification in furin-like pro-protein convertase cleavage site 2 consisting of amino acid residues 549-552 of Sema3C as set forth in SEQ ID NO: 1 or has at least 80%, preferably at least 90%, more preferably at least 95%, even more preferably at least 99% sequence identity) with the amino acid set forth in SEQ ID NO: 1, and at least one modification in furin-like pro-protein convertase cleavage site 3 consisting of amino acid residues 742-745 of Sema3C as set forth in SEQ ID NO: 1; wherein the modifications render the variant resistant to cleavage at the cleavage sites. According to some embodiments, the at least one modification in cleavage site 2 is a modification from the sequence RSRR as set forth in SEQ ID NO: 3 to the sequence KSKK as set forth in SEQ ID NO: 13. According to some embodiments, the at least one modification in cleavage site 3 is a truncation of at least part of the C-terminus of said variant as set forth in SEQ ID NO: 34. According to some embodiments, the at least one modification in cleavage site 3 is a truncation of the entire C-terminus of said variant as set forth in SEQ ID NO: 34. According to some embodiments, the variant of the invention is a variant of Semaphorin 3C as set forth in SEQ ID NO: 1, wherein the variant comprises a modification at furin-like pro-protein convertase (FPPC) cleavage site 2 as set forth in SEQ ID NO: 13 and a truncation of the C-terminus section of said variant as set forth in SEQ ID NO: 34. According to some embodiments, the variant of the invention further comprises at least one modification in a basic domain of said variant, the basic domain having an amino acid sequence as set forth in SEQ ID NO: 5. As used herein, the basic domain of Sema3C as set forth in SEQ ID NO: 5 consists of amino acids 724-745 of Sema3C as set forth in SEQ ID NO: 1.

According to some embodiments, the modification renders the variant of the invention resistant to cleavage by members of the furin-like pro-protein convertases. According to some embodiments, the members of the furin-like pro-protein convertases are selected from the group consisting of: furin, PC 1/3, PC2, PC4, PC 5/6, PACE4, PC7, Site-1 Protease, NARC-1 and a combination thereof. Each possibility represents a separate embodiment of the present invention.

According to some embodiments, the present invention provides a polynucleotide comprising cDNA corresponding to the variant of the invention. According to some embodiments, the present invention provides a polynucleotide encoding cDNA corresponding to the variant of the invention.

According to another aspect, the present invention provides a pharmaceutical composition comprising Semaphorin 3C or a variant of Semaphorin 3C as set forth in SEQ ID NO: 1, the variant comprising at least one modification in furin-like pro-protein convertase (FPPC) cleavage site 2 consisting of amino acid residues 549-552; and wherein the modification renders said variant resistant to cleavage at said cleavage site.

According to some embodiments, the present invention provides a pharmaceutical composition (also termed herein "the pharmaceutical composition of the invention") comprising at least one variant of the variants of the invention. According to some embodiments, the present invention provides the pharmaceutical composition comprising an effective amount of the variant of Semaphorin 3C or the wild type Semaphorin 3C of the invention for treating eye disease in a subject.

According to some embodiments, the present invention provides a pharmaceutical composition comprising at least one variant of Semaphorin 3C as set forth in SEQ ID NO: 1, the variant comprising at least one modification in furin-like pro-protein convertase (FPPC) cleavage site 2 consisting of amino acid residues 549-552 and wherein the modification renders said variant resistant to cleavage at said cleavage site, for treating eye disease in a subject.

According to some embodiments, the present invention provides a method for treating eye disease in a subject, the method comprising administering to the subject a pharmaceutical composition comprising at least one variant of Semaphorin 3C as set forth in SEQ ID NO: 1, the variant comprising at least one modification in furin-like pro-protein convertase (FPPC) cleavage site 2 consisting of amino acid residues 549-552 and wherein the modification renders said variant resistant to cleavage at said cleavage site.

According to some embodiments, the present invention provides a pharmaceutical composition comprising an effective amount of least one variant of Semaphorin 3C as set forth in SEQ ID NO: 1, the variant comprising at least one modification in furin-like pro-protein convertase (FPPC) cleavage site 2 consisting of amino acid residues 549-552 and wherein the modification renders said variant resistant to cleavage at said cleavage site for use for treating eye disease.

According to some embodiments, administration to the subject is by a route selected from the group consisting of: application of eye drop and intravitreal injection. Each possibility represents a separate embodiment of the present invention.

According to another aspect, the present invention provides an ophthalmologic pharmaceutical composition for treating an eye disease comprising as an active ingredient a therapeutically effective amount of wild-type Semaphorin 3C as set forth in SEQ ID NO: 1 or a variant thereof such as for example, the variant according to SEQ ID No. 8.

According to another aspect, the present invention provides a method for inhibiting or reducing lymphangiogenesis in an eye of a subject, the method comprising administering the pharmaceutical composition of the invention into the eye of the subject. According to some embodiments, the present invention provides a method for inhibiting or reducing lymphangiogenesis in an eye of a subject, the method comprising administering to the subject a pharmaceutical composition comprising at least one variant of Semaphorin 3C as set forth in SEQ ID NO: 1, the variant comprising at least one modification in furin-like pro-protein convertase (FPPC) cleavage site 2 consisting of amino acid residues 549-552; and wherein the modification renders said variant resistant to cleavage at said cleavage site.

According to some embodiments, the present invention provides a method for inhibiting or reducing lymphangiogenesis in an eye of a subject, the method comprising administering to the subject a pharmaceutical composition comprising as an active ingredient a therapeutically effective amount of wild-type Semaphorin 3C as set forth in set forth in SEQ ID NO: 1.

According to another aspect, the present invention provides a method for inhibiting or reducing angiogenesis in an eye of a subject, the method comprising administering the pharmaceutical composition of the invention to the subject. According to some embodiments, the present invention provides a method for inhibiting angiogenesis in a an eye of a subject, the method comprising administering to the subject a pharmaceutical composition comprising at least one variant of Semaphorin 3C as set forth in SEQ ID NO: 1, the variant comprising at least one modification in furin-like pro-protein convertase (FPPC) cleavage site 2 consisting of amino acid residues 549-552; and wherein the modification renders the variant resistant to cleavage at the cleavage site.

According to some embodiments, the present invention provides a method for inhibiting or reducing angiogenesis in an eye of a subject, the method comprising administering to the subject a pharmaceutical composition comprising as an active ingredient a therapeutically effective amount of wild-type Semaphorin 3C as set forth in SEQ ID NO: 1.

In an embodiment of the invention there is provided a method of treating age-related macular degeneration (AMD) and/or reducing abnormal angiogenesis and lymphangiogenesis in an eye of a patient comprising administering into an eye of a subject in need an effective amount of Semaphorin 3C as set forth in SEQ ID no. 1 or a variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders the variant resistant to cleavage at said cleavage site 2 and a pharmaceutically effective carrier. In some embodiments of the invention, the subject in need does not response to an anti VEGF, FGF, PDGF, FGFR, VEGFR, PDGFR eye therapy or developed resistance to anti VEGF, FGF, PDGF, FGFR, VEGFR, PDGFR eye therapy.

In some embodiments, the AMD is geographic atrophy or dry AMD or choroidal neovascularization or exudative AMD.

In some embodiments, the modification in furin-like pro-protein convertase cleavage site 2 is a modification of at least one arginine residue within said furin-like pro-protein convertase cleavage site 2. In some embodiments of the invention, the modification is a modification of at least one arginine residue within said furin-like pro-protein convertase cleavage site to a lysine residue. In some embodiments of the invention, the sema 3C variant further comprises at least one modification in a basic domain of said variant, the basic domain having an amino acid sequence as set forth in SEQ ID NO: 5. In some embodiments of the invention, the at least one modification in cleavage site 2 is a modification as set forth in SEQ ID NO: 13.

In some embodiments, the variant of sema3C further comprises a modification which is a truncation of at least part of the C-terminus of said variant as set forth in SEQ ID NO: 34.

In some embodiments, the one or more modifications render the sema3C variant resistant to cleavage at the cleavage site by members of the furin-like pro-protein convertases.

In some embodiments of the invention, the variant of Semaphorin 3C to be used for treating eye disease such as AMD, retinal diseases or eye diseases related to angiogenesis or lymphangiogenesis is as set forth in SEQ ID No. 8.

In some embodiments of the invention, the administration of the sema3C, the sema3C variant as described herein or the FR Sema3C into the eye of the subject need is by a direct injection into the eye, by intravitreal, ocular, intraocular application or by application of eye drops.

In some embodiments of the invention, the Semaphorin 3C as set forth in SEQ ID no. 1 or the variant of Semaphorin 3C, which has at least 80%, 90%, 95%, 99% or 100% sequence identity with the amino acid set forth in SEQ ID NO:1 are administered together with another therapeutic agent or with another treatment for age-related macular degeneration (AMD) and/or reducing abnormal angiogenesis and lymphangiogenesis. The another therapeutic agent is a VEGF inhibitor, or one or more inhibitors to FGF, PDGF, FGFR, VEGFR, PDGFR, wherein the another therapeutic agent is administered simultaneously or consecutively with the semaphorin 3C or the variant thereof.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The patent or application file contains at least one drawing executed in color. Copies of this patent or patent application publication with color drawings will be provided by the Office upon request and payment of the necessary fee.

FC (marked "UNCL-Sema3C/FC"; SEQ ID NO: 8), as described in Example 1 herein below (BD=Basic Domain; 1,2,3=FPPC cleavage sites 1, 2 and 3, respectively; Fc=FC tag). FPPC cleavage site 1 (RGRR; SEQ ID NO: 2) is identical in Sema3C and UNCL-Sema3C/Fc; FPPC cleavage site 2 comprises RSRR (SEQ ID NO: 3) in Sema3C and KSKK (SEQ ID NO: 13) in UNCL-Sema3C/Fc, FPPC cleavage site 3 comprises RNRR (SEQ ID NO: 4) in Sema3C and is replaced with Fc in UNCL-Sema3C/Fc. (B) A western-blot analysis, using an anti-FC antibody, analyzing conditioned media from HEK293 cells transfected with either an empty expression vector (NC), a construct encoding FC-tagged wild type Sema3C (Sema3C-wt) or a construct encoding UNCL-Sema3C/FC (UNCL-Sema3C).

FIGS. 2A-I show micrographs depicting cultures of human umbilical vein-derived endothelial cells (HUVEC) which were incubated with conditioned media from HEK293 cells transfected with either an empty expression vector (FIGS. 2A-C, termed "Empty Vector"), a construct encoding an FC-tagged variant of Sema3C cleaved at FPPC site 2 (FIGS. 2D-F, termed "Sema3C-p65-FC") or a construct encoding FC-tagged wild type Sema3C (FIGS. 2G-I, termed "Sema3C-wt") at 6.5, 13 or 16.5 hours following incubation.

FIGS. 3A-I show micrographs depicting Lymphatic Endothelial Cells (LEC) which were treated for 30 min with purified sema3E (H) or conditioned medium of HEK293 cells transfected with an empty vector (A) or a construct encoding either sema3A (D), sema3B (E), sema3C (B), sema3D (F), sema3F (C), sema3G (G) or sema6A (I). After the semaphorin treatment the cells were fixed and immno stained for actin and vinculin.

FIGS. 4A-F show micrographs depicting Lymphatic Endothelial Cells (LEC) which were incubated with conditioned media from HEK293 cells transfected with either an empty expression vector (FIGS. 4A-B, termed "Control"), a construct encoding FC-tagged wild type Sema3C (FIGS. 4C-D, termed "Sema3C-wt") or a construct encoding an FC-tagged variant of Sema3C cleaved at FPPC site 2 (FIGS. 4E-F, termed "Sema3C-p65-FC") at the beginning of the incubation (Time zero) and 1 hour following incubation.

Figures 1A, 1B:
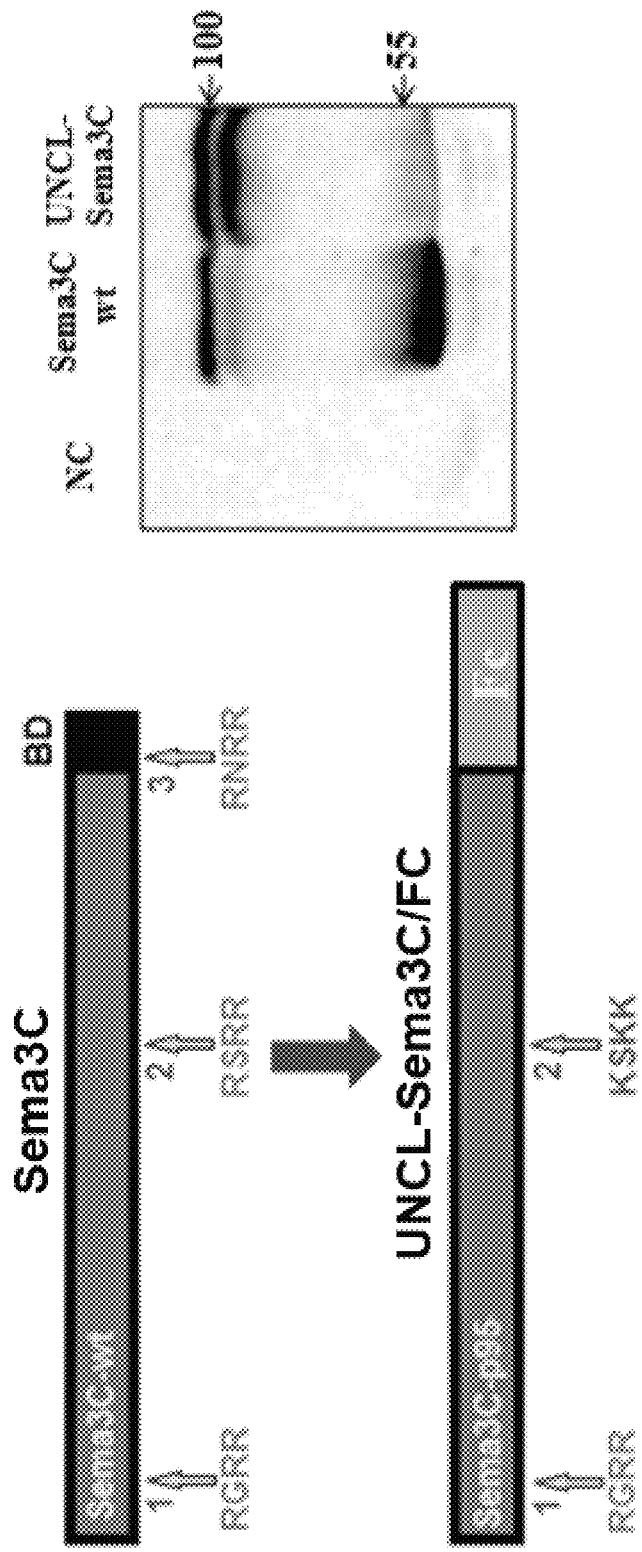
FIGS. 1A-B depict (A) a schematic representation of wild-type Sema3C (marked "Sema3C"; SEQ ID NO: 1) and an un-cleavable variant of Sema3C, termed UNCL-Sema3C/
Figure 5M:
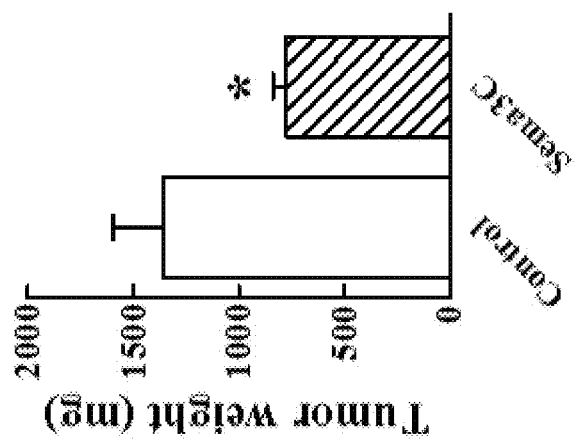

FIGS. 5A-M show micrographs (A-L) and a bar graph (M). FIGS. 5A-L depict micrographs of isolated sentinel lymph nodes which were adjacent to LM2-4 cells-induced tumors in mice visualized using phase contrast (A-D, I-J, marked "phase contrast") or fluorescent microscope detecting tomato-red fluorescence (E-H, K-L, marked "tomato-red fluorescence"). FIGS. 5A-H show lymph nodes extracted from mice in which tumors were induced by LM2-4 cells. FIGS. 5I-L show lymph nodes extracted from mice in which tumors were induced by LM2-4 cells expressing the uncleavable UNCL-Sema3C/myc-His construct, as described in Example 1. FIG. 5M shows a bar graph comparing tumor weights of tumors extracted from mice injected with LM2-4 cells (marked "control") or LM2-4 cells expressing the uncleavable UNCL-Sema3C/myc-His construct, as described in Example 1 (marked "Sema3C").

Figure 6:
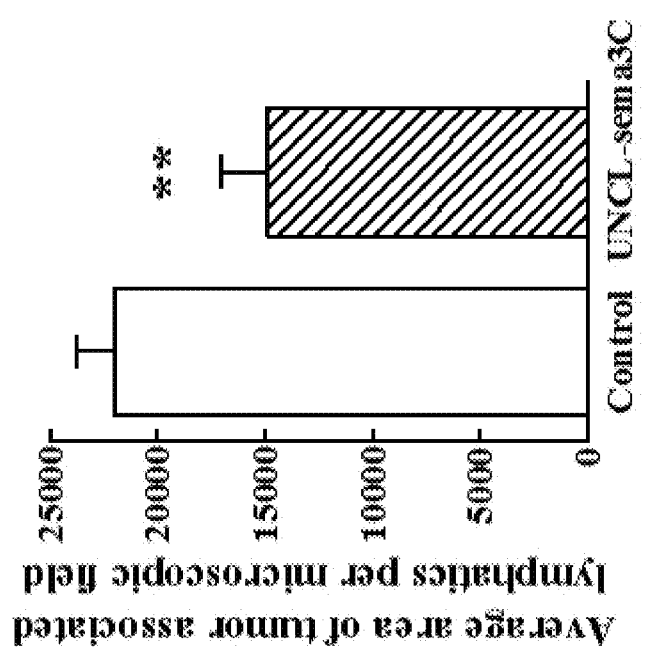

FIG. 6 shows a bar graph comparing the density of tumor associated lymph vessels in sections of tumors extracted from mice injected with LM2-4 cells (marked "control") or LM2-4 cells expressing the uncleavable UNCL-Sema3C/myc-His construct, as described in Example 1 (marked "UNCL-Sema3C").

Figure 7:
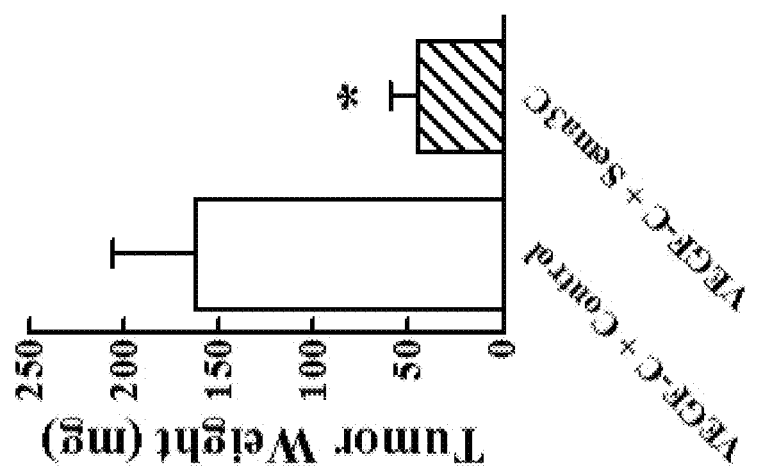

FIG. 7 shows a bar graph comparing tumor weights of tumors extracted from mice injected with MDA-MB-231 cells expressing human VEGF-C (marked "VEGFC+Control") or MDA-MB-231 cells expressing human VEGF-C and the uncleavable UNCL-Sema3C/myc-His construct, as described in Example 1 (marked "VEGF-C+Sema3C").

Figure 8:
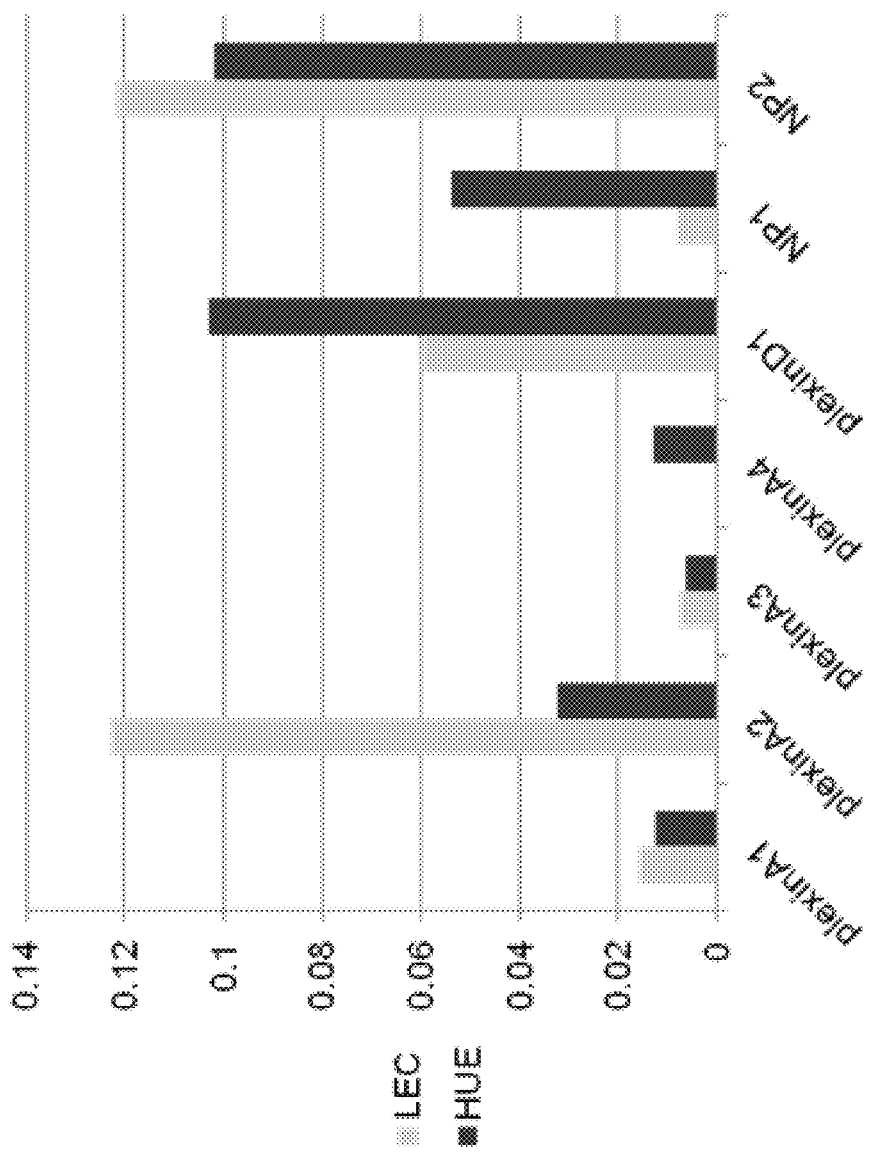

FIG. 8 shows a bar graph comparing real-time PCR quantification of expression for PlexinA1, PlexinA2, PlexinA3, PlexinA4, Plexin D1, NP1 and NP2 in cultured Lymphatic Endothelial Cells (marked "LEC") versus cultured Human Umbilical Vein-derived Endothelial Cells (marked "HUE").

FIGS. 9A-D show micrographs depicting Lymphatic Endothelial Cells (LEC) which were incubated with either elution buffer (A), UNCL-Sema3C-FC (B), Semaphorin 3E-FC (C) or Sema3C-p65-FC (D). The cells were stained with Phalloidin and an anti-Vinculin antibody and visualized using a fluorescent microscope (magnification: ×40).

FIGS. 10A-F show micrographs and graphs depicting HUVEC or LEC cells. A: HUVEC or LEC were seeded in 12 well dishes ($2 \times 10^4$ and $5 \times 10^4$ cells/well respectively) in LEC growth medium in the presence of vehicle (control) or FR-sema3C/Fc (2 µg/ml). Cells were photographed after 72 h. B. LEC and HUVEC were seeded in fibronectin coated 96 well dishes and the effect of FR-sema3C/Fc (2 µg/ml) on their proliferation was measured using the WST-1 proliferation assay kit. Shown is the average of N independent experiments. C. Confluent 6 well dishes containing LEC were incubated with vehicle or FR-Sema3C-Fc and stimulated with VEGF-C. Cell extracts were then subjected to western blot analysis using antibodies directed against phosphorylated VEGFR-3, phosphorylated-ERK1/2 and phosphorylated AKT. The blots were then stripped and re-probed with antibodies against VEGFR-3, ERK1/2 and AKT. Shown is a representative experiment out of several that were performed with similar results F. LEC silenced for the expression of the indicated receptors or control cells expressing a non-targeting shRNA (sh-control) were seeded in wells of the xCELLigence machine ($2 \times 10^4$ cells/well) and cultured for 24 h. They were subsequently stimulated with FR-sema3C/Fc (1 µg/ml). Cell contraction over time was then measured. Maximal contraction was determined as described in FIG. 10E. *** indicate P<0.001. D. The expression of the indicated receptors was silenced in LEC using lentiviral vectors encoding appropriate shRNA species. Total RNA was prepared from cells infected with a non-targeting sh-RNA (Sh-Control) or from cells in which the expression of the indicated receptors was silenced. Quantitative reverse PCR was used to determine the degree of silencing. E. Cells were seeded in wells of an E-plate 24 h prior to the experiment. In this example the cells were then stimulated with FR-sema3C/Fc (1 µg/ml) or with vehicle (Control). The difference between the response to the vehicle and FR-sema3C/Fc was defined as the maximal contraction and as shown by the double headed arrow.

FIGS. 11A-E show micrographs and graphs showing that FR-sema3C/myc does not affect cultured LM2-4 cells: A. Conditioned medium from LM2-4 cells expressing tomato red RFP and either empty vector (control) or a FR-Sema3C/myc encoding lentiviral vector was subjected to western blot analysis using anti-myc antibodies. B. HUVEC and LM2-4 were seeded in gelatin coated 12 well plates ($10^4$ cells/well). After 24 hours the medium was exchanged with conditioned media from LM2-4 cells infected with empty lentiviruses (control) or with conditioned medium from FR-sema3C/myc expressing LM2-4 cells and cell contraction assayed (mag. ×10). C. LM2-4 cells infected with FR-Sema3C/myc or with empty (Control) lentiviral vectors were seeded in 24 well dishes ($1 \times 10^5$ cells/well). The number of adherent cells after seeding (Day 0) or after 3 days was determined using a coulter-counter. Error bars represent the standard error of the mean derived from three independent experiments. D. The migration of LM2-4 cells infected with empty lentiviral vector (control) or with lentiviruses directing expression of FR-sema3C/myc was measured using the xCELLigence machine. E. The expression of the neuropilin-1 (NP1), neuropilin-2 (NP2) and plexin-D1 was examined in the indicated cell types using western blot analysis.

FIGS. 12A-G show micrographs and graphs demonstrating that FR-sema3C inhibits tumor development, tumor angiogenesis and tumor lymphangiogenesis: A. LM2-4 cells expressing tomato red RFP and either empty vector (control) or a FR-Sema3C/myc encoding lentiviral vector (2×106 cells in 50 µl PBS) were implanted in mammary fat pads of scid/nod mice. Tumors were excised after 30 days. Shown are the average tumor weights from N tumors obtained from three independent experiments. B. Representative paraffin section stained with hematoxilin and an antibody directed against LYVE-1. Arrows indicate intra-tumoral lymph vessels. C. The entire cross-section derived from each tumor was scanned and photographed. The ratio between the average area of LYVE-1 staining and the average area of the tumor sections (derived from N tumors) was determined using ImagePro. D. Representative paraffin section from a control tumor stained with hematoxilin and an antibody directed against CD31. Intra-tumoral blood vessels are indicated (arrows). E. The ratio between the average area of CD31 staining per tumor section from control and FR-sema3C/myc expressing tumors was determined as described under C. F. Single cell suspensions were prepared from control and FR-sema3C/myc expressing tumors. Cells were then incubated with antibodies directed against CD31. Flow cytometry was performed and results analyzed and quantified with Summit Version 4.3. Shown is the percentage of CD31 positive cells out of the total cell population of the tumor. G. The single cell suspensions described under C were incubated with antibodies directed against F4-80, CD11c and CD206. Flow cytometry was performed and results analyzed and quantified with Summit Version 4.3. The percentage of CD11c positive cells and CD206 positive cells out of the total F4-80 positive cells is shown. Error bars represent the standard error of the mean between different tumors.

FIGS. 13A-D show that FR-sema3C inhibit the spontaneous metastasis of LM2-4 cells to lymph nodes: A. LM2-4 cells expressing tomato red RFP and either empty vector (control) or a FR-Sema3C/myc encoding lentiviral vector were implanted in mammary fat pads. The proper axillary, lumbar aortic, and subiliac lymph nodes were excised after 30 days. The size of metastases in excised lymph nodes was quantified using the IVIS-200 imaging system. Lymph nodes containing metastases (yellow arrows) or not (green arrows) are shown. B. A representative histological section derived from a metastase containing lymph node derived from a mouse harboring a control tumor is shown at two different magnifications (a: ×10 and b: ×40). Also shown are histological sections from a clean lymph node from a mouse harboring a tumor containing FR-sema3C/myc expressing LM2-4 cells (c: ×10 and d: ×40). The sections were stained with Anti human-HLA-1 antibodies and counterstained with hematoxilin C. The percentage of mice containing detectable metastases in their lymph nodes in two independent experiments is depicted. D. The relative concentration of tomato red expressing LM2-4 cells in lymph nodes containing metastases was determined using the IVIS-200 system by measurement of the normalized photon density (photon/sec/cm2/sr) emitted.

FIGS. 14A-E: FR-sema3C inhibits VEGF and PDGF-BB-induced phosphorylation of ERK1/2 in endothelial cells (A) HUVEC were stimulated or not with VEGF (30 ng/ml) in the presence of elution buffer (100 mM glycine, 24 mM Tris, pH-7.2) or FR-sema3C/Fc (2 µg/ml). After ten minutes at room temperature the cells were lysed and ERK1/2 phosphorylation was determined by western blot as described. Shown is a representative experiment out of three that gave similar results. Below is shown a histogram depicting the ratio between the intensity of the respective phospho-ERK1/2 bands and the total ERK bands. (B) HUVEC were stimulated with PDGF-BB (50 ng/ml) in the presence or absence of FR-sema3C/Fc (2 µg/ml). ERK1/2 phosphorylation was determined and quantified as described under A. Shown is a representative experiment out of three that gave similar results. (C) HUVEC were stimulated with bFGF (5 ng/ml) in the presence or absence of FR-sema3C/Fc (2 µg/ml). ERK1/2 phosphorylation was determined and quantified as described under A. Shown is a representative experiment out of three that gave similar results. (D) HUVEC were stimulated with HGF (50 ng/ml) in the presence or absence of FR-sema3C/Fc (2 µg/ml). ERK1/2 phosphorylation was determined and quantified as described under A. Shown is a representative experiment out of three that gave similar results. (E) HUVEC were stimulated with EGF (50 ng/ml) in the presence or absence of FR-sema3C/Fc (2 µg/ml). ERK1/2 phosphorylation was determined and quantified as described under A. Shown is a representative experiment out of three that gave similar results. Statistical significance was evaluated using the one tailed Mann-Whitney test. Error bars represent the standard error of the mean. *: $p<0.05$ FIGS. 15A-C: FR-Sema3C inhibits CNV induced by laser photocoagulation (A) Four laser burns were made around the optic nerve in each eye of C57 black mice (6 mice per group). Eyes were injected immediately after with FR-sema3C/Fc (0.1 µg) or with aflibercept (5 µg) in a 2 µl volume, or with an equal volume of vehicle (100 mM glycine, 24 mM Tris, pH-7.2) (Control) as described. The RPE/choroid/sclera complex was excised after a week following injection of FITC-dextran into the circulation. Shown are representative fluorescent photographs of blood vessels invading laser burns from control, aflibercept and FR-Sema3C/Fc treated eyes. The area representing the CNV area measured in B is encircled by a yellow line. (B) Quantification of the area of stained blood vessels that invaded laser burns in the experiment described under A was performed as described in the Examples section below. The means obtained from individual mice within an experimental group were then compared and evaluated for statistical significance using one way ANOVA followed by Bonferroni's multiple comparison post test. (C) The effect of increasing FR-Sema3C/Fc concentrations on CNV was evaluated as described. To assess the effects of FR-sema3C on CNV induced by laser photocoagulation, the mean area of invading blood vessels per laser burn was determined from eight separate laser burns that were performed in both eyes. The means obtained from individual mice within an experimental group (4 mice) were then compared and evaluated for statistical significance using one way ANOVA followed by Bonferroni's multiple comparison post test. Error bars represent the standard error of the mean. *: $p<0.05$, **: $p<0.01$ FIGS. 16A-E. The function of the retina is not compromised after a single bolus intravitreal injection of FR-sema3C (A) Six mice were injected with 2 μL of vehicle (100 mM glycine, 24 mM Tris, pH-7.2) in their right eyes and with 2 μl of FR-sema3C/Fc (0.1 μg) in their left eyes. Visual function was measured by OKR tests performed on day-3 and 24 after intravitreal injection as described in materials and methods, and compared to the Visual function of both eyes prior to injection (day 0). (B and D) Vehicle alone (control) was injected into the vitreal cavities of the left eyes of six mice and FR-sema3C/Fc (see FIG. 20C) (0.1 μg) was injected into the vitreal cavities of their right eyes as described under A. Scotopic (B) and photopic (D) ERG responses of a- and b-wave amplitudes were measured 23 days after injection as described in materials and methods and compared to the scotopic and photopic ERG responses of both eyes prior to injection (day 0). (C and E). The average maximal ERG response amplitude of scotopic (C) and photopic (E) a-waves and b-waves of eyes treated with vehicle alone (Cont.) or with FR-sema3C/Fc (see FIG. 20C) 23 days after FR-sema3C/Fc injection. Error bars represent the standard error of the mean. Statistical significance was evaluated using student's t-test. ns: non-specific.

FIGS. 17A-D: Injection of FR-sema3C does not affect retinal morphology (A) Shown are representative photographs of haematoxy-lin-eosin stained transverse sections from a retina derived from the eye of a mouse injected with vehicle alone (Control) or from an eye injected with FR-sema3C/Fc after 23 days. (B) Shown are representative photographs of a GFAP stained retina derived from the eye of a mouse injected with vehicle (control) or from an eye injected with FR-sema3C/Fc after 23 days. Both retinas were devoid of GFAP labeling in Müller cells. (C) Shown are representative photographs of PKCα stained retinas derived from the eye of a mouse injected with vehicle alone (control) or from an eye injected with FR-sema3C/Fc 23 days previously. (D) Shown are representative photographs of isolectin-IB4 stained retinal blood vessels. The retinas were collected after a week following intravitreal injection with FR-Sema3C/Fc (0.1 μg) or Vehicle alone (control). O.N.L—Outer nuclear layer, I.N.L—Inner nuclear layer.

FIGS. 18A-E: FR-sema3C inhibits in endothelial cells VEGF-induced phosphorylation of P38 MAP-Kinase, AKT and FAK[125]

(A) HUVEC were stimulated or not with VEGF (30 ng/ml) in the presence of elution buffer (100 mM glycine, 24 mM Tris, pH-7.2) or FR-sema3C/Fc (2 μg/ml). After ten minutes at room temperature the cells were lysed and p38 MAPK phosphorylation on T180 and Y182 was determined using western blot analysis as described in the Examples section below. Shown is a representative experiment out of three that produced similar results. Below is shown a histogram depicting the ratio between the intensity of the respective pT180/Y182-p38 MAPK bands and the total p38 MAPK bands. (B) HUVEC were stimulated as described under A. FAK[125] phosphorylation was determined and quantified as described in the Examples section below. Below is shown a histogram depicting the ratio between the intensity of the phosphorylated FAK[125] pY397 bands and total FAK. Shown is a representative experiment out of two that produced similar results. (C) HUVEC were stimulated as described under A. AKT phosphorylation was determined and quantified as described in the Examples section below. Shown is a representative experiment out of two that gave similar results. A histogram depicting the ratio between the intensity of the respective pS473-AKT bands and the total AKT bands is shown below. (D) HUVEC were stimulated or not with PDGF-BB (50 ng/ml) in the presence or absence of Aflibercept (2 μg/ml). Shown is a representative experiment out of three that gave similar results. ERK1/2 phosphorylation was determined and quantified as described in the Examples section below. (E) HUVEC were stimulated or not with bFGF (5 ng/ml) in the presence or absence of Aflibercept (2 μg/ml). ERK1/2 phosphorylation was determined and quantified as described in materials and methods. Shown is a representative experiment out of two that gave similar results. Below is shown a histogram depicting the ratio between the intensity of the respective phospho-ERK1/2 bands and the total ERK1/2 bands.

Figure 19B:
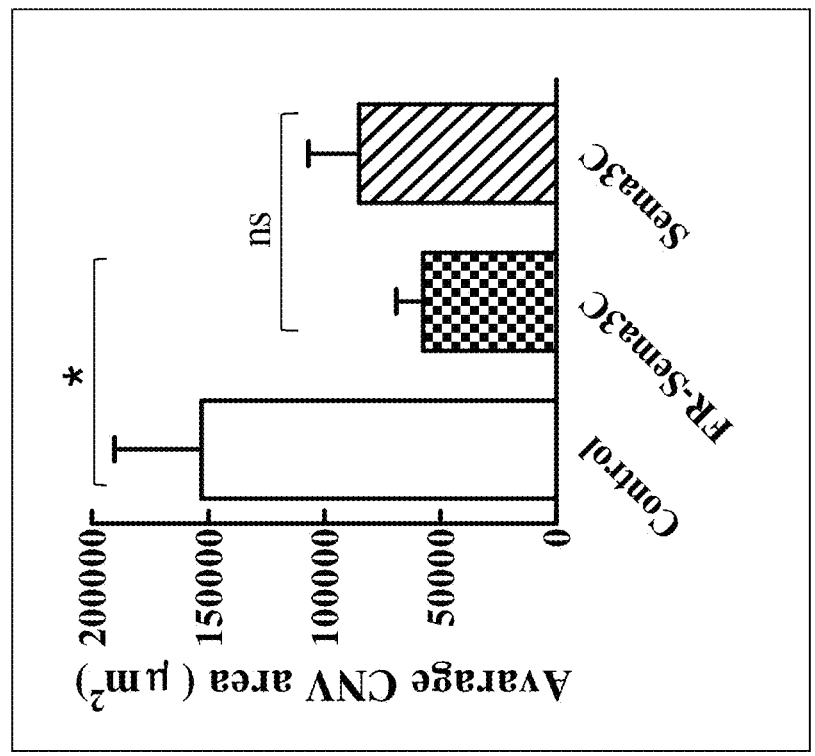
Figure 19A:
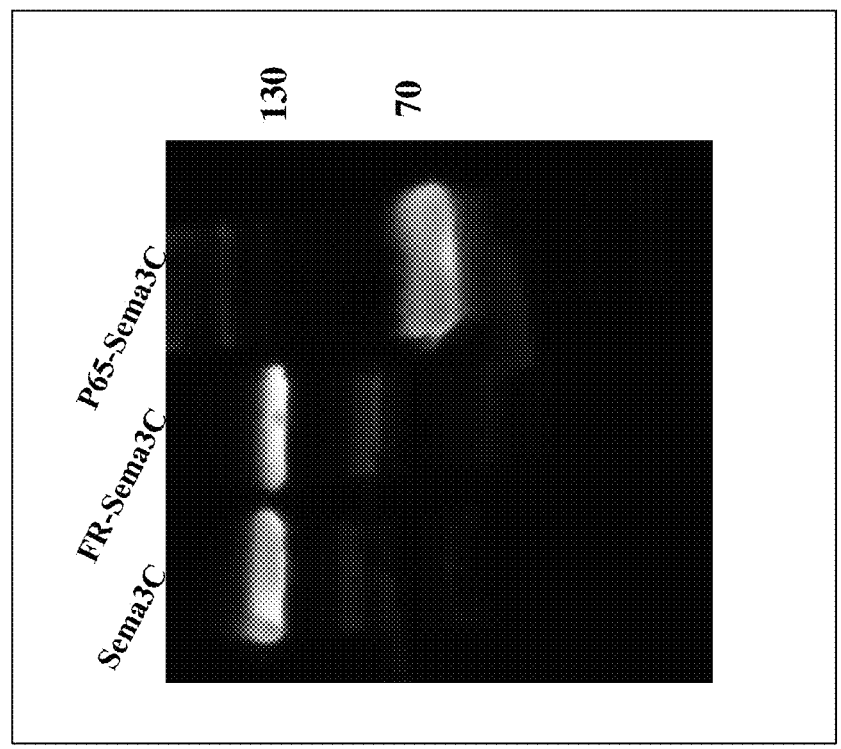
Figure 19C:
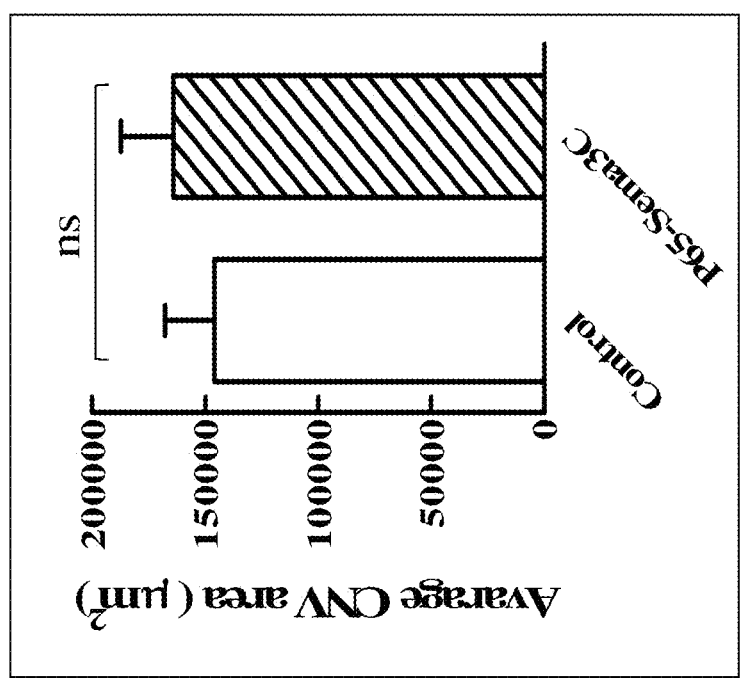

FIGS. 19A-C: Comparison of the effects of sema3C, FR-sema3C and p65-Sema3C on laser photocoagulation-induced CNV (A) FR-Sema3C, Sema3C and p65-Sema3C were resolved on an 8% SDS/PAGE gel and subjected to western blot analysis using antibodies directed against the N-terminal of Sema3C (B) Four laser burns were made around the optic nerve in each eye of C57 black mice (3 mice per group). Eyes were injected immediately after with FR-sema3C/Fc (0.1 μg) or with Sema3C (0.1 μg) in a 2 μl volume, or with an equal volume of vehicle (100 mM glycine, 24 mM Tris, pH-7.2) (Control) as described. The RPE/choroid/sclera complex was excised after a week following injection of FITC-dextran into the circulation. Quantification of the area of stained blood vessels that invaded laser burns was performed as described. Statistical analysis was performed as described in FIG. 2. Error bars represent the standard error of the mean. *: p<0.05. (C) Four laser burns were made around the optic nerve in each eye of the C57 black mice (3 mice per group). Eyes were injected immediately after with p65-Sema3C (0.1 μg) in a 2 μl volume, or with an equal volume of vehicle (Control) as described above. The RPE/choroid/sclera complex was excised after a week following injection of FITC-dextran into the circulation. Quantification of the area of stained blood vessels that invaded laser burns and statistical analysis were performed as described above.

Figure 20C:
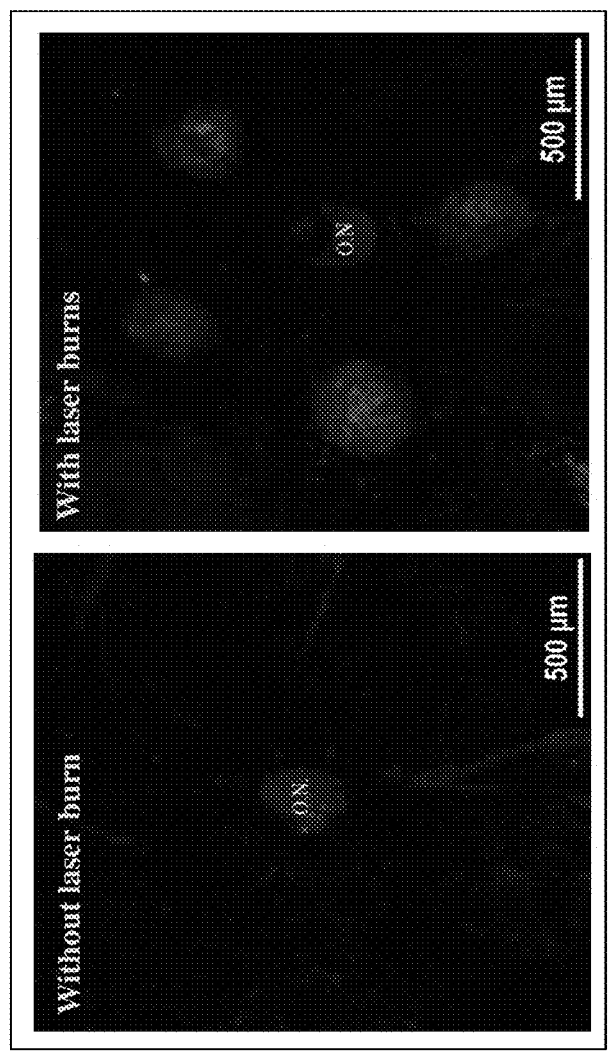

FIGS. 20A-C: Images of retinas and flat mounted choroid before and after treatment (A) Mice were intravitreally injected with FR-Sema3C (0.1 μg) or with Sema3C (0.1 μg) or with Vehicle alone (control). Retinas were collected after a week and apoptotic cells were visualized by TUNEL staining. The bright dots represent the TUNEL-stained pyknotic bodies. For positive control, retinas were treated with 2,500 units/ml of DNAse I for ten minutes. Shown are representative images out of four retinas that were assayed in each group. (B) Mice were intravitreally injected with Sema3C (0.1 μg) or Vehicle alone (control), and retinas were collected after a week as described. Retinal vessels were visualized following staining with Isolectin-IB4. (C) Representative images of flat-mounted choroid after isolectin-IB$_4$ staining a week after laser photocoagulation in comparison with FR-Sema3C/Fc treated eyes that were not subjected to laser photocoagulation. O.N, optic nerve.

DETAILED DESCRIPTION OF THE INVENTION

The present invention provides, for the first time, variants of Semaphorin 3C (Sema 3C) having modifications in furin-like pro-protein convertase (FPPC) cleavage sites, such that the modifications render the sites resistant to cleavage. Unexpectedly, the un-cleavable Sema 3C variants were found to suppress growth of a breast-cancer-induced tumor and to prevent the spreading of metastases to sentinel lymph nodes surrounding the tumor. Surprisingly, the Sema 3C variants were further found to reduce the formation of tumor associated lymph vessels.

As used herein, the terms "Semaphorin 3C" and "Sema 3C" are used interchangeably and refer to human Semaphorin 3C as set forth in SEQ ID NO: 1. The polynucleotide sequence encoding Sema3C (as set forth in SEQ ID NO: 1) is set forth in SEQ ID NO: 15. Human Semaphorin 3C, as set forth in SEQ ID NO: 1, comprises three furin-like pro-protein convertase (FPPC) cleavage sites, referred to herein as site 1, site 2 and site 3:

1. As used herein, the terms "site 1", "cleavage site 1" and "furin-like pro-protein convertase cleavage site 1" are used interchangeably and refer to a site having SEQ ID NO: 2, consisting of amino acids 144-147 of SEQ ID NO: 1;
2. As used herein, the terms "site 2", "cleavage site 2" and "furin-like pro-protein convertase cleavage site 2" are used interchangeably and refer to a site having SEQ ID NO: 3, consisting of amino acids 549-552 of SEQ ID NO: 1; and
3. As used herein, the terms "site 3", "cleavage site 3" and "furin-like pro-protein convertase cleavage site 3" are used interchangeably and refer to a site having SEQ ID NO: 4, consisting of amino acids 742-745 of SEQ ID NO: 1 within the basic domain of Sema 3C.

As used herein, the basic domain of Sema 3C (referred to herein also as "the basic domain"), as set forth in SEQ ID NO: 5, consists of amino acids 724-745 of SEQ ID NO: 1.

According to some embodiments, the FPPC cleavage sites are cleavable by furin-like pro-protein convertases. According to some embodiments, furin-like pro-protein convertases (FPPCs) able to cleave the FPPC cleavage sites according to the present invention are selected from the group consisting of: furin, PC 1/3, PC2, PC4, PC 5/6, PACE4, PC7, Site-1 Protease, NARC-1 and a combination thereof. Each possibility represents a separate embodiment of the present invention.

Naturally occurring Sema3C is present as a mixture of the FPPC-cleaved and non-cleaved forms. As exemplified herein below, Sema 3C cleaved at site 2 is unable to induce contraction of Vascular Endothelial Cells (VECs) and/or Lymphatic Endothelial Cells (LECs). According to some embodiments, Sema 3C cleaved at site 2 does not possess anti-angiogenic properties and/or anti-lymphangiogenic properties. Each possibility represents a separate embodiment of the present invention. Without wishing to be bound by any theory or mechanism, cleavage of Sema 3C at FPPC cleavage site 2 by FPPCs secreted by cells, such as malignant tumour cells, results in loss or decrease of anti-angiogenic and/or anti-lymphangiogenic properties possessed by un-cleavable Sema 3C variants. It is therefore contemplated, in a non-limiting manner, that the ability of naturally occurring Sema3C (referred to herein also as wild-type Sema3C) to inhibit angiogenic and lymphangiogenic properties is attributed to the non-cleaved form of Sema3C. According to some embodiments, the N-terminal part of Sema 3C which has undergone at site 2 is termed Sema 3C-p65, as set forth in SEQ ID NO: 6. It is to be understood that variants of Sema3C which are cleaved at site 2, such as Sema3C-p65, are not included in the variants of the invention.

According to one aspect, the present invention provides a variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site.

The term "variant" as used herein refers to a polypeptide sequence that possesses some modified structural property of the native Sema3C either as set forth in SEQ ID NO: 1 or which has at least 80%, 90%, 95% or 99% sequence identity) with the amino acid set forth in SEQ ID NO: 1.

According to some embodiments, the term "variant" as used herein refers to native Sema3C as set forth in SEQ ID NO: 1 which possesses at least one modification in FPPC site 2 which renders the variant resistant to cleavage. As used herein, the terms "polypeptide" and "protein" are used interchangeably and refer to a polymer of amino acid residues.

According to some embodiments, the variant of the invention comprises at least one modification in furin-like pro-protein convertase cleavage site 2 consisting of amino acid residues 549-552 of Sema3C as set forth in SEQ ID NO: 1; wherein the modification prevents the variant from being cleaved at cleavage site 2. According to some embodiments, the variant of the invention comprises at least one modification in furin-like pro-protein convertase cleavage site 2 consisting of amino acid residues 549-552 of Sema3C as set forth in SEQ ID NO: 1; wherein the modification prevents the variant from being cleaved at cleavage site 2 by furin-like pro-protein convertases (FPPCs).

According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to RSKR (as set forth in SEQ ID NO: 11), preferably to KSKR (as set forth in SEQ ID NO: 12), most preferably to KSKK (as set forth in SEQ ID NO: 13). Each possibility represents a separate embodiment of the present invention. According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13). According to some embodiments, the variant of the invention comprises a deletion of at least part of furin-like pro-protein convertase cleavage site 2 consisting of amino acid residues 549-552 of Sema3C as set forth in SEQ ID NO: 1.

According to some embodiments, the variant of the invention comprises at least one modification in furin-like pro-protein convertase cleavage site 3 consisting of amino acid residues 742-745 of Sema3C as set forth in SEQ ID NO: 1; wherein the modification renders the variant resistant to cleavage at cleavage site 3. According to some embodiments, the variant of the invention comprises at least one modification in furin-like pro-protein convertase cleavage site 3 consisting of amino acid residues 742-745 of Sema3C as set forth in SEQ ID NO: 1; wherein the modification prevents the variant from being cleaved at cleavage site 3 by furin-like pro-protein convertases (FPPCs). According to some embodiments, a modification in furin-like pro-protein convertase cleavage site 3 of Sema3C as set forth in SEQ ID NO: 1, preventing cleavage at site 3, is a modification selected from the group consisting of: at least one amino-acid substitution within site 3, at least one amino-acid deletion within site 3 and a combination thereof. Each possibility represents a separate embodiment of the present invention.

According to some embodiments, the variant of the invention comprises a deletion of at least part of furin-like pro-protein convertase cleavage site 3 consisting of amino acid residues 742-745 of Sema3C as set forth in SEQ ID NO: 1. According to some embodiments, the variant of the invention comprises a deletion of furin-like pro-protein convertase cleavage site 3 consisting of amino acid residues 742-745 of Sema3C as set forth in SEQ NO: 1.

According to some embodiments, the variant of the invention comprises a truncation of at least part of the C-terminus of Sema3C as set forth in SEQ ID NO: 34. According to some embodiments, the variant of the invention comprises a truncation of at least part of the C-terminus of Sema3C from FPPC cleavage site 3 and downstream, as set forth in SEQ ID NO: 36. According to some embodiments, the variant of the invention comprises a truncation of the C-terminus of Sema3C as set forth in SEQ ID NO: 34. According to some embodiments, the variant of the invention comprises a truncation of the C-terminus of Sema3C from FPPC cleavage site 3 and downstream, as set forth in SEQ ID NO: 36. According to some embodiments, a truncation of the C-terminus of Sema3C as set forth in SEQ ID NO: 34 comprises FPPC site 3. According to some embodiments, a truncation of the C-terminus of Sema3C as set forth in SEQ ID NO: 36 comprises FPPC site 3. According to some embodiments, the variant of the invention comprises a truncation of at least part of the C-terminus of said variant, such that at least FPPC cleavage site 3 is truncated.

According to some embodiments, a variant according to the invention is a variant of Sema3C as set forth in SEQ ID NO: 1, the variant comprising a truncation of part of the basic domain such that furin-like pro-protein convertase cleavage site 3 is deleted. According to some embodiments, the variant of the invention in which the C-terminus as set forth in SEQ ID NO: 34 is truncated, is missing both furin-like pro-protein convertase cleavage site 3 and the ADAMTS1 cleavage site.

It is to be understood that the exact amino-acid sequence of the ADAMTS1 cleavage site in Sema3C is unknown, although it is believed to be within the 13 C-terminal amino acids as set forth in SEQ ID NO: 34 (Esselens C. et al., 2009, J. Biol. Chem., 285: 2463-2473). According to some embodiments, the variant of the invention comprises at least one modification of the ADAMTS1 cleavage site. According to some embodiments, the variant of the invention comprises at least one modification of the ADAMTS1 cleavage site rendering the site non-cleavable. According to some embodiments, the variant of the invention comprises at least one modification of the ADAMTS1 cleavage site rendering the site non-cleavable by members of the ADAMTS extracellular metalloproteases. According to some embodiments, the variant of the invention comprises a deletion of at least part of the ADAMTS1 cleavage site. According to some embodiments, the variant of the invention comprises a deletion of the ADAMTS1 cleavage site.

According to some embodiments, the variant of the invention comprises at least one modification in furin-like pro-protein convertase cleavage site 2 consisting of amino acid residues 549-552 of Sema3C as set forth in SEQ ID NO: 1, and at least one modification in furin-like pro-protein convertase cleavage site 3 consisting of amino acid residues 742-745 of Sema3C as set forth in SEQ ID NO: 1; wherein the modifications render the variant resistant to cleavage at the cleavage sites.

According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of the amino acid sequence set forth in SEQ ID NO: 34. According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of at least part of the amino acid sequence set forth in SEQ ID NO: 34. According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of the amino acid sequence set forth in SEQ ID NO: 34; wherein said variant is as set forth in SEQ ID NO: 35.

According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of the amino acid sequence set forth in SEQ ID NO: 36. According to some embodiments, a variant according to the invention is a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of at least part of the amino acid sequence set forth in SEQ ID NO: 36.

According to some embodiments, a variant of Sema3C as set forth in SEQ ID NO:1, comprising a modification of furin-like pro-protein convertase cleavage site 2 from RSRR (as set forth in SEQ ID NO: 3) to KSKK (as set forth in SEQ ID NO: 13) and further comprising a C-terminal truncation of the amino acid sequence set forth in SEQ ID NO: 34 is referred to herein as "UNCL-Sema3C" also termed here "FR-Sema3C". According to some embodiments, UNCL-Sema3C comprises a C-terminal tag. According to some embodiments, UNCL-Sema3C comprises a C-terminal FC-tag, having a sequence as set forth in SEQ ID NO: 8. According to some embodiments, UNCL-Sema3C comprises a C-terminal myc-6His tag, having a sequence as set forth in SEQ ID NO: 9.

Bioactivity of Sema 3C variants, as used herein, refers to the ability of Sema3C variants to elicit at least one of Sema 3C's biological responses, such as, but not limited to, the ability to inhibit cell migration or the ability to induce collapse of cellular cytoskeleton in HUVECs. According to some embodiments, the variants of the invention are bioactive. The bioactivity of Sema 3C variants may be assayed by any method known in the art, such as, but not limited to, induction of HUVEC contraction, cell migration assays, immune-staining of cells for cytoskeletal markers and the like.

According to some embodiments, modification in an FPPC cleavage site according to the present invention is a modification which renders said site resistant to cleavage. According to some embodiments, modification in an FPPC cleavage site according to the present invention is a modification which renders said site resistant to cleavage by furin-like pro-protein convertases (FPPCs).

According to some embodiments, a modification according to the invention is selected from the group consisting of: at least one amino-acid substitution, at least one amino-acid deletion and a combination thereof. Each possibility represents a separate embodiment of the present invention. According to some embodiments, a modification according to the invention is at least one amino-acid substitution. According to some embodiments, a modification according to the invention is at least one amino-acid deletion. According to some embodiments, a modification according to the invention is a modification which prevents cleavage at a furin-like pro-protein convertase cleavage site. According to some embodiments, the modification is an amino acid deletion comprising at least part of the amino acids of an FPPC cleavage site. According to some embodiments, the modification is a truncation comprising at least part of the amino acids of the FPPC cleavage site.

According to some embodiments, a modification according to the invention is an amino acid truncation. According to some embodiments, a modification of furin-like pro-protein convertase cleavage site 3 which renders this site non-cleavable is a truncation of at least part of the basic domain as set forth in SEQ ID NO: 5. According to some embodiments, the variant of the invention comprises a truncation of at least part of the basic domain of Sema3C as set forth in SEQ ID NO: 5. According to some embodiments, the Sema3C variant of the invention comprises a complete truncation of the basic domain. According to some embodiments, the variant of the invention comprises at least one modification in the basic domain of Sema3C as set forth in SEQ ID NO: 5.

According to some embodiments, a modification of furin-like pro-protein convertase cleavage site 3 which renders this site non-cleavable is a truncation of at least part of the C-terminus of Sema3C, the C-terminus set forth in SEQ ID NO: 34. According to some embodiments, the variant of the invention comprises a truncation of at least part of the C-terminus of Sema3C, the C-terminus set forth in SEQ ID NO: 34. According to some embodiments, the Sema3C variant of the invention comprises a complete truncation of the C-terminus of Sema3C, the C-terminus set forth in SEQ ID NO: 34. According to some embodiments, the variant of the invention comprises at least one modification in the C-terminus of Sema3C, the C-terminus set forth in SEQ ID NO: 34.

According to some embodiments, the modification is a modification of at least one Arginine residue within a furin-like pro-protein convertase cleavage site. Non-limiting examples of modifications of at least one Arginine residue within furin-like pro protein convertase cleavage site 2 are modifications of site 2 from RSRR (as set forth in SEQ ID NO: 3) to RSKR (as set forth in SEQ ID NO: 11), KSKR (as set forth in SEQ ID NO: 12), or KSKK (as set forth in SEQ ID NO: 13). Each possibility represents a separate embodiment of the present invention.

According to some embodiments, the modification is a modification of at least one Arginine residue within a furin-like pro-protein convertase cleavage site to a Lysine residue. According to other embodiments, the modification is a modification of all Arginine residues within a furin-like pro-protein convertase cleavage site.

According to some embodiments, the modification prevents the variant of the invention from being cleaved at a furin-like pro-protein convertase cleavage site. According to some embodiments, the modification prevents the variant of the invention from being cleaved at a furin-like pro-protein convertase cleavage site by members of the furin-like pro-protein convertases (FPPCs). According to some embodiments, the members of the furin-like pro-protein convertases are selected from the group consisting of: furin, PC 1/3, PC2, PC4, PC 5/6, PACE4, PC7, Site-1 Protease, NARC-1 and a combination thereof. Each possibility represents a separate embodiment of the present invention.

According to some embodiments, the Semaphorin 3C variant of the invention further comprises a protein tag. According to some embodiments, the protein tag is selected from the group consisting of: an N-terminal protein tag, a C-terminal protein tag and a combination thereof. Each possibility represents a separate embodiment of the present invention. According to some embodiments, the Semaphorin 3C variant of the invention is conjugated to a moiety which extends the half-life of said variant. According to some embodiments, wild-type Semaphorin 3C according to the invention is conjugated to a moiety which extends the half-life of said variant. Non-limiting examples of moieties which may extend the half-life of the Semaphorin3C variants of the invention are polyethylene glycol (PEG), polypeptides such as poly-glycine and XTEN (Amunix), hyaluronic acid, albumin and an immunoglobulin or a part thereof, such as, but not limited to, the Fc region.

According to some embodiments, the Semaphorin 3C variant of the invention comprises a protein tag. According to some embodiments, the Semaphorin 3C variant of the invention comprises a protein tag upon production but the tag is cleaved and/or removed from the variant prior to incorporation into the composition of the invention and/or use in treating cancer. Each possibility represents a separate embodiment of the present invention. Cleavage and/or removal of a protein tag may be performed by any methods known in the art, such as, but not limited to, enzymatic and/or chemical cleavage, so as long as the Sema3C variant remains functional. According to some embodiments, a functional Semaphorin3C variant refers to a variant which is able to treat cancer. According to some embodiments, a functional Semaphorin3C variant refers to a variant which is able to suppress growth of a tumor and/or reduce occurrence of metastases. Each possibility represents a separate embodiment of the present invention. According to some embodiments, a functional Semaphorin3C variant refers to a variant which is able to inhibit angiogenesis. According to some embodiments, a functional Semaphorin3C variant refers to a variant which is able to inhibit lymphangiogenesis. According to some embodiments, a functional Semaphorin3C variant refers to a variant which is able to elicit at least one activity selected from the group consisting of: inhibit angiogenesis, inhibit lymphangiogenesis, suppress growth of a cancerous tumor and reduce occurrence of metastases. Each possibility represents a separate embodiment of the present invention. Non-limiting examples of Sema3C variants comprising a protein tag according to the present invention are: UNCL-Sema3C/FC (as set forth in SEQ ID NO: 8) and UNCL-Sema3C/myc-6His (as set forth in SEQ ID NO: 9), produced as described herein below in Example 1.

According to some embodiments, wild-type Semaphorin 3C as set forth in SEQ ID NO: 1 further comprises a protein tag. According to some embodiments, wild-type Semaphorin 3C as set forth in SEQ ID NO: 1 comprises a protein tag upon production but the tag is cleaved and/or removed from the variant prior to incorporation into a pharmaceutical composition of the invention and/or use in inhibiting lymphogenesis and/or angiogenesis. Each possibility represents a separate embodiment of the present invention.

As used herein, the term "protein tag" refers to a peptide sequence bound to the N-terminus or C-terminus of a protein. According to some embodiments, protein tags may comprise glycoproteins. According to some embodiments, protein tags may be used for separation and/or purification and/or visualization of the bound proteins. Each possibility represents a separate embodiment of the present invention. Non-limiting examples of protein tags are: Fc, Myc, Human influenza hemaglutinin (HA), Flag, His, Gluthathione-S-Transferase (GST) and a combination thereof. Each possibility represents a separate embodiment of the present invention. As used herein, an Fc tag refers to a tag encoding at least part of the Fc region of an immunoglobulin G (IgG) class antibody.

According to some embodiments, the Sema3C variant of the invention is an isolated variant. As used herein, the term "isolated" means either: 1) separated from at least some of the components with which it is usually associated in nature; 2) prepared or purified by a process that involves the hand of man; and/or 3) not occurring in nature.

According to some embodiments, the Semaphorin 3C variants of the invention, as disclosed herein, may be produced by recombinant or chemical synthetic methods. According to some embodiments, the Semaphorin 3C variants of the invention, as disclosed herein may be produced by recombinant methods from genetically-modified host cells. Any host cell known in the art for the production of recombinant proteins may be used for the present invention. In some embodiments, the host cell is a prokaryotic cell. Representative, non-limiting examples of appropriate prokaryotic hosts include bacterial cells, such as cells of *Escherictahia coli* and *Bacillus subtilis*. In other embodiments, the host cell is a eukaryotic cell. In some exemplary embodiments, the host cell is a fungal cell, such as yeast. Representative, non-limiting examples of appropriate yeast cells include *Saccharomyces cerevisiae* and *Pichia pastoris*. In additional exemplary embodiments, the host cell is a plant cell. According to other exemplary embodiments, the host cell is a mammalian cell in culture. Following are non-limiting examples of recombinant and chemical synthetic methods suitable for production of the Semaphorin 3C variants of the invention.

Recombinant Expression

As used herein, the term "gene" has its meaning as understood in the art. In general, a gene is taken to include gene regulatory sequences (e.g. promoters, enhancers, etc.) and/or intron sequences, in addition to coding sequences (open reading frames).

As used herein, the terms "polypeptide" and "protein" are used interchangeably and refer to a polymer of amino acid residues.

As used herein, the term "DNA construct" refers to an artificially assembled or isolated nucleic acid molecule which comprises a gene of interest or a coding region of interest. According to some embodiments, the coding region of interest is cDNA encoding a Sema3C variant of the invention, such as, but not limited to variants set forth in sequences selected from the group consisting of: SEQ ID NO. 8, SEQ ID NO. 9, SEQ ID NO. 10, SEQ ID NO. 35. Each possibility represents a separate embodiment of the present invention.

As used herein, the term "vector" refers to any recombinant polynucleotide construct (such as a DNA construct) that may be used for the purpose of transformation, i.e. the introduction of heterologous DNA into a host cell. One exemplary type of vector is a "plasmid" which refers to a circular double stranded DNA loop into which additional DNA segments can be ligated. Another exemplary type of vector is a viral vector, wherein additional DNA segments can be ligated into the viral genome. Certain vectors are capable of autonomous replication in a host cell into which they are introduced.

As used herein, a "primer" defines an oligonucleotide which is capable of annealing to (hybridizing with) a target nucleotide sequence, thereby creating a double stranded region which can serve as an initiation point for DNA synthesis under suitable conditions.

As used herein, the terms "transformation" refers to the introduction of foreign DNA into cells. The terms "transformants" or "transformed cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

A Semaphorin 3C variant may be synthesized by expressing a polynucleotide molecule encoding the variant in a host cell, for example, a microorganism cell transformed with the nucleic acid molecule.

DNA sequences encoding wild type polypeptides, such as Semaphorin 3C, may be isolated from any cell producing them, using various methods well known in the art. For example, a DNA encoding the wild-type polypeptide may be amplified from genomic DNA by polymerase chain reaction (PCR) using specific primers, constructed on the basis of the nucleotide sequence of the known wild type sequence. The genomic DNA may be extracted from the cell prior to the amplification using various methods known in the art.

The isolated polynucleotide encoding the wild type polypeptide may be cloned into a vector, such as, but not limited to, the pET28a or pGEM-T easy plasmids.

Upon isolation and cloning of the polynucleotide encoding the wild type polypeptide, desired mutation(s) may be introduced, in order to arrive at a polynucleotide sequence encoding a desired Sema3C variant according to the invention, by modification at one or more base pairs, using methods known in the art. Such methods include, for example, site-specific mutagenesis, cassette mutagenesis, recursive ensemble mutagenesis and gene site saturation mutagenesis. Methods are also well known for introducing multiple mutations into a polynucleotide. For example, introduction of two and/or three mutations can be performed using commercially available kits, such as the QuickChange site-directed mutagenesis kit (Stratagene).

An alternative method to producing a polynucleotide with a desired sequence is the use of a synthetic gene. A polynucleotide encoding a desired polypeptide may be prepared synthetically, for example using the phosphoroamidite method. The polynucleotide thus produced may then be subjected to further manipulations, including one or more of purification, annealing, ligation, amplification, digestion by restriction endonucleases and cloning into appropriate vectors. The polynucleotide may be ligated either initially into a cloning vector, or directly into an expression vector that is appropriate for its expression in a particular host cell type. In the case of a fusion protein, or a protein fused with a protein tag, different polynucleotides may be ligated to form one polynucleotide. For example, different polynucleotides may be ligated into linearized pET21a.

The polynucleotide encoding the Sema3C variant of the invention may be incorporated into a wide variety of expression vectors, which may be transformed into in a wide variety of host cells.

Introduction of a polynucleotide into the host cell can be effected by well-known methods, such as chemical transformation (e.g. calcium chloride treatment), electroporation, conjugation, transduction, calcium phosphate transfection, DEAE-dextran mediated transfection, transvection, micro-injection, cationic lipid-mediated transfection, scrape loading, ballistic introduction and infection.

Representative, non-limiting examples of appropriate hosts include bacterial cells, such as cells of *E. coli* and *Bacillus subtilis*. The variants of the invention may be encoded in any vector suitable for expression. The appropriate vector is determined according to the selected host cell. Vectors for expressing proteins in *E. coli*, for example, include, but are not limited to, pET, pK233, pT7 and lambda pSKF. Other expression vector systems are based on beta-galactosidase (pEX); maltose binding protein (pMAL); and glutathione S-transferase (pGST). The polypeptides may be designed to include a protein tag, for example, a His-Tag (six consecutive histidine residues), which can be isolated and purified by conventional methods.

Selection of a host cell transformed with the desired vector may be accomplished using standard selection protocols involving growth in a selection medium which is toxic to non-transformed cells. For example, in the case of *E. coli*, it may be grown in a medium containing an antibiotic selection agent; cells transformed with the expression vector which further provides an antibiotic resistance gene, will grow in the selection medium.

Upon transformation of a suitable host cell, and propagation under conditions appropriate for protein expression, the variant of the invention may be identified in cell extracts of the transformed cells. Transformed hosts expressing the variant of the invention may be identified by analyzing the proteins expressed by the host, for example, using SDS-PAGE and comparing the gel to an SDS-PAGE gel obtained from the host which was transformed with the same vector but not containing a nucleic acid sequence encoding the desired variant.

The desired variants which have been identified in cell extracts may be isolated and purified by conventional methods, including ammonium sulfate or ethanol precipitation, acid extraction, salt fractionation, ion exchange chromatography, hydrophobic interaction chromatography, gel permeation chromatography, affinity chromatography, and combinations thereof.

The isolated variants may be analyzed for their various properties, for example specific activity, using methods known in the art. In a non-limiting example, Semaphorin 3C variants according to the invention may be analyzed for their ability to induce contraction of human umbilical vein-derived endothelial cells (HUVECs). Conditions for carrying out the aforementioned procedures as well as other useful methods are readily determined by those of ordinary skill in the art.

Synthetic Production

Semaphorin 3C variants according to the present invention may also be produced by synthetic means using well known techniques, such as solid phase synthesis. Synthetic polypeptides may be produced using commercially available laboratory peptide design and synthesis kits. In addition, a number of available FMOC peptide synthesis systems are available. Assembly of a polypeptide or fragment can be carried out on a solid support using for example, an Applied Biosystems, Inc. Model 431A automated peptide synthesizer. The polypeptides may be made by either direct synthesis or by synthesis of a series of fragments that can be coupled using other known techniques.

According to some embodiments, the present invention provides a polynucleotide corresponding to the Sema3C variant of the invention. According to some embodiments, the present invention provides a polynucleotide encoding cDNA which corresponds to the Sema3C variant of the invention.

According to some embodiments, the present invention provides a polynucleotide encoding the Sema3C variant of the invention. According to some embodiments, the present invention provides a polynucleotide encoding a variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site.

According to some embodiments, the present invention provides a polynucleotide encoding a variant of Semaphorin 3C as set forth in SEQ ID NO: 1, wherein the variant comprises at least one modification in furin-like pro-protein convertase cleavage site 2 consisting of amino acid residues 549-552 and at least one modification in furin-like pro-protein convertase cleavage site 3 consisting of amino acid residues 742-745; and wherein the modifications render said variant resistant to cleavage at said cleavage sites.

According to some embodiments, the present invention provides a polynucleotide encoding a Sema3C variant according to the invention which comprises a protein-tag, such as, but not limited to, the polynucleotides encoded by SEQ ID NO: 22 and SEQ ID NO: 23 encoding the variants having SEQ ID NO:8 or SEQ ID NO: 9, respectively. According to some embodiments, the present invention provides a polynucleotide encoding the Sema3C variant encoded by SEQ ID NO: 35.

According to some embodiments, the invention provides a vector comprising the polynucleotide of the invention. As used herein, the term "the polynucleotide of the invention" refers to a polynucleotide encoding the variant of the invention. According to some embodiments, the present invention provides a host cell transfected with a vector comprising the polynucleotide of the invention.

According to some embodiments, the present invention provides a pharmaceutical composition comprising a variant of Semaphorin 3C as set forth in SEQ ID NO: 1, wherein the variant comprises at least one modification in furin-like pro-protein convertase cleavage site 2 consisting of amino acid residues 549-552 of Sema3C as set forth in SEQ ID NO: 1; wherein the modification renders the variant resistant to cleavage at cleavage site 2.

According to some embodiments, the present invention provides a pharmaceutical composition comprising a variant of Semaphorin 3C as set forth in SEQ ID NO: 1, wherein the variant comprises at least one modification in furin-like pro-protein convertase cleavage site 2 consisting of amino acid residues 549-552 and at least one modification in furin-like pro-protein convertase cleavage site 3 consisting of amino acid residues 742-745; and wherein the modifications render said variant resistant to cleavage at said cleavage sites.

According to some embodiments, the present invention provides a pharmaceutical composition comprising at least one of the Sema3C variants of the invention. According to some embodiments, the present invention provides a pharmaceutical composition comprising a therapeutically effective amount of at least one of the Sema3C variants of the invention. According to some embodiments, the pharmaceutical composition of the invention further comprises a pharmaceutically acceptable carrier. As used herein, the term "the pharmaceutical composition of the invention" refers to a composition comprising at least one of the Sema3C variants of the invention.

According to another aspect, the present invention provides a pharmaceutical composition comprising as an active ingredient a therapeutically effective amount of wild-type Semaphorin 3C as set forth in SEQ ID NO: 1.

According to another aspect, the present invention provides a method for treating cancer in a subject, the method comprising administering the pharmaceutical composition of the invention to the subject. According to some embodiments, the present invention provides a method for treating cancer in a subject, the method comprising administering to the subject a pharmaceutical composition comprising a therapeutically effective amount of at least one of the Sema3C variants of the invention. According to some embodiments, the present invention provides a method for treating cancer in a subject, the method comprising administering to the subject a pharmaceutical composition comprising as an active ingredient a therapeutically effective amount of wild-type Semaphorin 3C as set forth in SEQ ID NO: 1.

According to some embodiments, the present invention provides a method for treating cancer in a subject, the method comprising administering to the subject a pharmaceutical composition comprising a therapeutically effective amount of at least one variant of Semaphorin 3C as set forth in SEQ ID NO: 1, wherein the variant comprises at least one modification in furin-like pro-protein convertase cleavage site 2 consisting of amino acid residues 549-552 of Sema3C as set forth in SEQ ID NO: 1; wherein the modification renders the variant resistant to cleavage at cleavage site 2.

The experiments in the Examples Section show that the class-3 semaphorin sema3C is the only class-3 semaphorin besides sema3F that is able to induce the collapse of the cytoskeleton of LEC suggesting that sema3C may function as a modulator of lymphangiogenesis and of lymph vessels mediated tumor metastasis. The sema3C cleavage product p65-Sema3C was inactive when its ability to induce the collapse of the cytoskeleton of LEC was examined. Accordingly, the point mutated FR-sema3C variant of sema3C which is resistant to cleavage by FPPC was used in the experiments.

FR-sema3C effectively induced the collapse of the cytoskeleton of LEC and HUVEC. These effects were mediated in LEC by the neuropilin-2 receptor and by the D1 and A1 plexin receptors which form functional class-3 semaphorin receptors when they associate with neuropilins. Silencing plexin-A3 had no effect on FR-sema3C/Fc-induced contraction of LEC. This is surprising because sema3F, the other semaphorin that induces contraction of LEC is known to transduce signals using neuropilin-2 and plexin-A3. FR-sema3C also inhibited potently the proliferation of LEC and less effectively the proliferation of vascular endothelial cells. Like wild type sema3C, FR-sema3C had no effect either on the proliferation or on the cytoskeletal organization of the highly metastatic LM2-4 breast cancer cells, possibly because these cells do not express the neuropilin-2 receptor. FR-sema3C inhibited VEGF-C-induced signal transduction in LEC suggesting that it may indeed function in-vivo as an inhibitor of lymphangiogenesis. FR-sema3C expressing LM2-4 cells formed tumors in mammary fat pads of mice but their growth was inhibited by about 50% as compared with the growth rate of control tumors. This was probably the result of an anti-angiogenic effect because the concentration of blood vessels in tumors formed from FR-sema3C expressing cells was reduced by 50% as compared to their concentration in tumors that developed from control cells. The reduced concentration of blood vessels cannot be explained solely by a direct effect of FR-sema3C on endothelial cells of blood vessels because in-vitro FR-sema3C only inhibited the proliferation of vascular endothelial cells by about 20%. A reduction in the concentration of activated M2 macrophages in the FR-sema3C expressing tumors. M2 tumor associated macrophages were found to enhance angiogenesis and lymphangiogenesis was also observed and it is possible that inhibition of their recruitment by FR-sema3C contributes to the FR-sema3C-induced inhibition of angiogenesis and lymphangiogenesis.

The concentration of lymph vessels in the tumors that developed from the FR-sema3C expressing cells was also reduced by about 50% as compared to their density in control tumors, suggesting that FR-sema3C does indeed function as an anti-lymphangiogenic factor. The expression of FR-sema3C in the tumor cells inhibited potently the spread of tumor cells to lymph nodes Similar effects were observed when signal transduction induced by lymphangiogenic factors such as VEGF-C and VEGF-D was inhibited, suggesting that the inhibition of metastasis by FR-sema3C is indeed due to its anti-lymphangiogenic activity. Both the number of metastases containing lymph nodes as well as the size of metastases in metastases containing lymph nodes were reduced in mice harbouring tumors derived from FR-sema3C expressing LM2-4 cells. These results suggest that FR-sema3C may be used to inhibit the metastatic spread of breast cancer tumors and possibly of additional types of tumors that disseminate using the lymphatic system.

According to some embodiments, the present invention provides a method for treating cancer in a subject, the method comprising administering to the subject a pharmaceutical composition comprising a therapeutically effective amount of at least one variant of Semaphorin 3C as set forth in SEQ ID NO: 1, wherein the variant comprises at least one modification in furin-like pro-protein convertase cleavage site 2 consisting of amino acid residues 549-552 and at least one modification in furin-like pro-protein convertase cleavage site 3 consisting of amino acid residues 742-745; and wherein the modifications render said variant resistant to cleavage at said cleavage sites.

According to some embodiments, as used herein, the term "therapeutically effective amount" relates to an amount sufficient to induce at least one of the following clinical effects when administered to a subject: suppression of tumor growth in the subject, reduction of metastases occurrence in the subject, inhibition of lymphangiogenesis, inhibition of angiogenesis and a combination thereof. Each possibility represents a separate embodiment of the present invention.

According to some embodiments, treating is selected from the group consisting of: suppressing growth of a tumor, reducing occurrence of metastases and a combination thereof. Each possibility represents a separate embodiment of the present invention. According to some embodiments, treating is suppressing growth of a tumor in a subject. According to some embodiments, treating is arresting growth of a tumor in a subject. According to some embodiments, a tumor in a subject treated with the composition of the invention according to the methods of the invention is of a smaller size and/or weight than a comparable tumor in a subject not treated with the composition of the invention. Each possibility represents a separate embodiment of the present invention.

According to some embodiments, treating is reducing occurrence of metastases in a subject. According to some embodiments, treating is reducing occurrence of metastases in lymph nodes of a subject. According to some embodiments, treating is reducing occurrence of metastases in sentinel lymph nodes of a subject. As used herein, the term "sentinel lymph nodes" refers to lymph nodes draining a cancer tumor. According to some embodiments, treating is reducing the number of metastases in a subject. According to some embodiments, treating is reducing the size of metastases in a subject. According to some embodiments, metastases are metastases in lymph nodes, preferably metastases in sentinel lymph nodes. According to some embodiments, treating is inhibiting growth of metastases. According to some embodiments, treating is inhibiting or suppressing the spreading of metastases. Each possibility represents a separate embodiment of the present invention. According to some embodiments, treating is inhibiting or suppressing the spreading of metastases to lymph nodes, preferably to sentinel lymph nodes. Each possibility represents a separate embodiment of the present invention. Without wishing to be bound by any theory or mechanism, the ability of the Sema3C variants of the invention to inhibit or suppress lymphangiogenesis may contribute to their ability to suppress or inhibit the spreading of metastases to sentinel lymph nodes of a tumor.

According to some embodiments, treating is inhibiting lymphangiogenesis. According to some embodiments, treating is suppressing lymphangiogenesis. According to some embodiments, treating is inhibiting or suppressing lymphangiogenesis in a tumor. Each possibility represents a separate embodiment of the present invention. According to some embodiments, treating is inducing contraction of lymphatic endothelial cells. According to some embodiments, treating is reducing the density of lymph nodes in a tumor. According to some embodiments, treating is suppressing growth of lymph nodes in a tumor. According to some embodiments, treating is reducing the density of tumor associated lymph vessels. According to some embodiments, treating is suppressing growth of tumor associated lymph vessels. According to some embodiments, treating is reducing lymphatic drainage of a tumor.

According to some embodiments, "tumor" as used herein refers to an abnormal mass of tissue resulting from cancer. According to some embodiments, cancer according to the present invention is selected from the group consisting of: lymphoma, breast cancer, head and neck cancer, squamous carcinomas of the head and neck (HNSCC), lung cancer, rectal cancer, bile duct cancer, bladder cancer, bone cancer, colon cancer, brain cancer, cervical cancer, ocular melanoma, Kaposi's sarcoma, leukemia, melanoma, myeloma, ovarian cancer, vaginal cancer, prostate cancer, testicular cancer, endometrial cancer, thyroid cancer and thymus cancer. Each possibility represents a separate embodiment of the present invention. According to some embodiments, the cancer is breast cancer. According to some embodiments, the cancer is lymphoma. According to some embodiments, the cancer is a cancer which induces tumors that send metastases into lymph nodes. According to some embodiments, the cancer is a cancer which spreads through lymph nodes. According to some embodiments, the cancer is a cancer which spreads through lymph nodes such as, but not limited to, breast cancer, malignant melanoma, lymphoma and head and neck cancer. According to some embodiments, the cancer is a cancer which induces tumors that secrete factors which induce angiogenesis. According to some embodiments, the cancer is a cancer which induces tumors that secrete factors which induce lymphangiogenesis. According to some embodiments, the cancer is a cancer which induces tumors that secrete at least one type of furin-like pro-protein convertase (FPPC). According to some embodiments, the cancer is a cancer which induces tumors that secrete at least one type of furin-like pro-protein convertase (FPPC) known to cleave Sema3C at site 2. According to some embodiments, the cancer is a cancer which induces tumors that secrete at least one type of furin-like pro-protein convertase (FPPC) known to cleave Sema3C at site 2 and/or site 3. Each possibility represents a separate embodiment of the present invention. Without wishing to be bound by any theory or mechanism, the Sema3C variants of the invention are suitable to treat a tumor that secretes at least one type of FPPC known to cleave Sema3C, since they are not susceptible to the effects of the FPPCs.

According to some embodiments, the present invention provides the composition of the invention for treating cancer in a subject. According to some embodiments, the present invention provides a pharmaceutical composition comprising as an active ingredient a therapeutically effective amount of wild-type Semaphorin 3C as set forth in SEQ ID NO: 1 for treating cancer in a subject.

According to another aspect, the present invention provides a method for inhibiting or suppressing lymphangiogensis in a subject, the method comprising administering to a subject a pharmaceutical composition comprising a therapeutically effective amount of at least one of the Sema3C variants of the invention. Each possibility represents a separate embodiment of the present invention. According to some embodiments, the present invention provides a method for inhibiting or suppressing lymphangiogensis in a subject, the method comprising administering to a subject a pharmaceutical composition comprising as an active ingredient a therapeutically effective amount of wild-type Semaphorin 3C as set forth in SEQ ID NO: 1.

According to some embodiments, the present invention provides a method of treatment of a disease or condition which is associated with excessive lymphangiogenesis or which may benefit from inhibition or suppression of lymphangiogenesis, the method comprising administering to a subject a pharmaceutical composition comprising a therapeutically effective amount of at least one of the Sema3C variants of the invention. Each possibility represents a separate embodiment of the present invention. According to some embodiments, the present invention provides a method of treatment of a disease or condition which is associated with excessive lymphangiogenesis or which may benefit from inhibition or suppression of lymphangiogenesis, the method comprising administering to a subject a pharmaceutical composition comprising as an active ingredient a therapeutically effective amount of wild-type Semaphorin 3C as set forth in SEQ ID NO: 1. Each possibility represents a separate embodiment of the present invention. Non-limiting examples of conditions which may benefit from reduced lymphangiogenesis are lymphatic edema and lymphangiomatosis.

As used herein, the term "lymphangiogenesis" refers to formation and/or growth of lymphatic vessels de-novo or from existing lymphatic vessels. As exemplified herein below, aside from Sema3F previously shown as a repellent of lymphatic endothelial cells (LECs), Sema3C was unexpectedly found to be the only class 3 Semaphorin to induce LEC collapse.

According to some embodiments, the present invention provides a method for inhibiting lymphangiogensis in a subject, the method comprising administering to a subject a pharmaceutical composition comprising a therapeutically effective amount of at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site. Each possibility represents a separate embodiment of the present invention. According to some embodiments, a therapeutically effective amount is an amount sufficient for inhibiting lymphangiogenesis in a subject.

According to some embodiments, administration of the pharmaceutical composition of the invention to a subject results in inhibition or suppression of lymphangiogenesis. Each possibility represents a separate embodiment of the present invention. According to some embodiments, administering the composition of the invention to a subject afflicted with cancer results in inhibiting or suppressing lymphangiogenesis in a tumor. Each possibility represents a separate embodiment of the present invention. According to some embodiments, administering the composition of the invention to a subject afflicted with cancer results in inhibiting or suppressing lymphangiogenesis of tumor associated lymph vessels. Each possibility represents a separate embodiment of the present invention. According to some embodiments, inhibition or suppression of lymphangiogenesis refers to inhibition or suppression of at least 50%, possibly at least 70%, alternatively at least 90% of lymphangiogenesis in a subject non-treated with the composition of the invention or a composition comprising wild type Sema3C as set forth in SEQ ID NO: 1. Each possibility represents a separate embodiment of the present invention. According to some embodiments, inhibition or suppression of lymphangiogenesis is local. According to some embodiments, administering the composition of the invention to a subject afflicted with cancer results in reduction in the density of tumor associated lymph vessels. According to some embodiments, administering the composition of the invention to a subject afflicted with cancer results in suppression of tumor associated lymph vessel growth. According to some embodiments, administering the composition of the invention to a subject afflicted with cancer results in reduction of lymphatic drainage of a tumor.

Without wishing to be bound by any theory or mechanism, the ability of the Sema3C variants of the invention to reduce the density of tumor associated lymph vessels, may contribute to their ability to suppress tumor growth and/or suppress the spreading of metastases to sentinel lymph nodes.

According to some embodiments, the variant of the invention is capable of suppressing or inhibiting lymphangiogenesis. Each possibility represents a separate embodiment of the present invention. According to some embodiments, the variant of the invention is capable of suppressing or inhibiting spread of metastases. Each possibility represents a separate embodiment of the present invention. According to some embodiments, the variant of the invention is capable of suppressing or inhibiting spread of metastases to lymph nodes, preferably sentinel lymph nodes. Each possibility represents a separate embodiment of the present invention.

According to some embodiments, the present invention provides the composition of the invention for inhibiting or suppressing lymphangiogenesis. Each possibility represents a separate embodiment of the present invention. According to some embodiments, the present invention provides a pharmaceutical composition comprising as an active ingredient a therapeutically effective amount of wild-type Semaphorin 3C as set forth in SEQ ID NO: 1 for inhibiting or suppressing lymphangiogenesis. Each possibility represents a separate embodiment of the present invention.

According to another aspect, the present invention provides a method for inhibiting or suppressing angiogensis in a subject, the method comprising administering to a subject a pharmaceutical composition comprising a therapeutically effective amount of at least one of the Sema3C variants of the invention. Each possibility represents a separate embodiment of the present invention. According to another aspect, the present invention provides a method for inhibiting or suppressing angiogenesis in a subject, the method comprising administering to a subject a pharmaceutical composition comprising as an active ingredient a therapeutically effective amount of wild-type Semaphorin 3C as set forth in SEQ ID NO: 1.

According to some embodiments, inhibition or suppression of angiogenesis refers to inhibition or suppression of at least 50%, preferably at least 70%, most preferably at least 90% of angiogenesis in a subject non-treated with the composition of the invention. Each possibility represents a separate embodiment of the present invention.

According to some embodiments, the present invention provides a method for inhibiting angiogensis in a subject, the method comprising administering to a subject a pharmaceutical composition comprising a therapeutically effective amount of at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site. Each possibility represents a separate embodiment of the present invention. According to some embodiments, a therapeutically effective amount is an amount sufficient for inhibiting lymphangiogenesis in a subject.

As used herein, the term "angiogenesis" refers to formation of blood-vessels de-novo or from existing blood vessels. According to some embodiments, administration of the composition of the invention results in collapse of blood-vessel endothelial cells. According to some embodiments, administration of the composition of the invention to a subject afflicted with cancer results in inhibition or suppression of angiogenesis of blood cells supplying blood to a tumor and/or metastases. Each possibility represents a separate embodiment of the present invention. Without wishing to be bound by any theory or mechanism, the ability of wild-type Sema3C and the Sema3C variants of the invention to inhibit both angiogenesis and lymphangiogenesis contributes to their ability to suppress the growth of a tumor and/or reduce occurrence of metastases, mostly metastases in lymph nodes. According to some embodiments, the variant of the invention is capable of suppressing or inhibiting angiogenesis. Each possibility represents a separate embodiment of the present invention.

According to some embodiments, the present invention provides the composition of the invention for suppression or inhibition of angiogenesis. Each possibility represents a separate embodiment of the present invention. According to some embodiments, the present invention provides a pharmaceutical composition comprising as an active ingredient a therapeutically effective amount of wild-type Semaphorin 3C as set forth in SEQ ID NO: 1 for suppression or inhibition of angiogenesis. Each possibility represents a separate embodiment of the present invention.

According to some embodiments, as used herein, the terms "subject" or "a subject in need thereof" are used interchangeably and refer to a subject afflicted with a pathology selected from the group consisting of: cancer, a pathology which would benefit from inhibition of lymphangiogenesis, a pathology which would benefit from inhibition of angiogenesis and a combination thereof. Each possibility represents a separate embodiment of the present invention. According to some embodiments, a subject is a subject afflicted with cancer. According to some embodiments, a subject is a subject afflicted with a pathology which would benefit from inhibition of lymphangiogenesis. According to some embodiments, a subject is a subject afflicted with a pathology which would benefit from inhibition of angiogenesis.

Any suitable route of administration to a subject may be used for the composition of the present invention, including but not limited to, topical and systemic routes. According to some embodiments, administering is administering systematically. According to some embodiments, the composition is formulated for systemic administration.

According to another embodiment, administration systemically is through a parenteral route. According to some embodiments, preparations of the composition of the invention for parenteral administration include sterile aqueous or non-aqueous solutions, suspensions, or emulsions, each representing a separate embodiment of the present invention. Non-limiting examples of non-aqueous solvents or vehicles are propylene glycol, polyethylene glycol, vegetable oils such as olive oil and corn oil, gelatin, and injectable organic esters such as ethyl oleate.

According to some embodiments, parenteral administration is administration intravenously, intra-arterially, intramuscularly, intraperitoneally, intradermally, transdermally, intravitreally, or subcutaneously. Each of the abovementioned administration routes represents a separate embodiment of the present invention. According to another embodiment, parenteral administration is performed by bolus injection. According to another embodiment, parenteral administration is performed by continuous infusion.

According to another embodiment, parenteral administration is transmucosal administration. According to another embodiment, transmucosal administration is transnasal administration. For transmucosal administration, penetrants appropriate to the barrier to be permeated are used in the formulation. Such penetrants are generally known in the art. The preferred mode of administration will depend upon the particular indication being treated and will be apparent to one of skill in the art.

It is shown herein in Example 12 that FR-Sema3C, a full length point mutated sema3C resistant to cleavage by FPPC inhibits VEGF as well as PDGF-BB and to some extent also bFGF, induced signal transduction in cultured endothelial cells as well as laser photocoagulation induced CNV in a mouse AMD model. FR-sema3C has been used rather than wild type sema3C, even though both function as effective inhibitors of angiogenesis Currently 23-30% of exudative AMD patients either do not benefit from treatment with VEGF inhibitors or further loose vision as assessed in the ANCHOR and CATT clinical trials. Furthermore, more than 50% of patients treated with anti-VEGF medications demonstrate persistent sub-macular fluid on OCT, an indicator of active disease. Inefficacy of anti-VEGF therapy may result from the treatment's inability to target established vascular lesions or since these treatments cannot prevent the emergence of new lesions driven by VEGF-independent angiogenesis pathways such as ECM-induced, neuropilin-1 dependent angiogenesis In the laser-induced CNV mouse model FR-Sema3C inhibited CNV as effectively as aflibercept at a concentration that was 50 fold lower than the effective aflibercept concentration. Importantly, FR-sema3C did not compromise retinal structure as assessed by histological and immunochemical examination nor did it affect retinal function as assessed by functional OKR and ERG tests. However, it is possible that the histological and functional assays performed may not be able to detect subtle defects resulting from treatment with FR-sema3C, and in addition it is likely that the human responses to FR-sema3C may differ from the responses of mice. Thus, FR-sema3C may perhaps be of benefit for those patients that do not respond well to current treatments with VEGF inhibitors. In mice FR-sema3C seems safe as it did not compromise retinal function.

Abnormal lymphangiogenesis is a complicating factor in additional diseases. Abnormal angiogenesis and lymphangiogenesis represents a complication of inflammatory several eye diseases in which new blood vessels and new lymph vessels invade the normally transparent cornea. This can be induced by irritants, limbal insufficiency, or complications of surgical procedures such cornea grafting and cause loss of vision. These observations suggest that inhibitors of lymphangiogenesis could be useful as drugs for the treatment of such eye diseases as well as of additional diseases involving inflammatory lymphangiogenesis such as inflammatory bowel disease or various complications of diabetes. Indeed, some inhibitors targeting the VEGFR-3 receptor which acts as the receptor for the lymphangiogenic factors VEGF-C and VEGF-D are currently in clinical trials. Accordingly, it is intended to determine if injection of FR-sema3C or application of eye drops containing FR-sema3C can be used to treat such eye diseases in pre-clinical animal models.

Inflammation, neo-lymphangiogenesis and neo-angiogenesis will be induced in the corneas of eyes of c57 black mice or rat eyes using alkali burn or suture placement as described. FR-sema3C/Fc will be applied as drops or by injection in order to determine if it inhibits neo-angiogenesis and neo-lymphangiogenesis. Vehicle alone will be used as a control, and results will be compared to the effects of the VEGF inhibitor Avastin. A positive result will be a significant inhibition of lymphangiogenesis and angiogenesis to the cornea.

The results in Example 12 clearly show that CNV induced by laser photocoagulation in a mouse model is inhibited by intra-vitreal injection of FR-sema3C. It is shown that the inhibition is as potent as the inhibition produced by injection of aflibercept but at a concentration that is 50 fold lower than the aflibercept concentration required to produce a similar effect. Further, it is shown that injection of FR-sema3C into untreated mouse eyes is not accompanied by the loss of visual acuity or persistent sub/intraretinal fluid as determined by OKR and ERG. The semaphorin 3C or the variant thereof of the invention for prevention or treatment of an ocular disease or condition are typically administered by ocular, intraocular, and/or intravitreal injection.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitreal injections are usually repeated at intervals which depend on the patient's condition, and the properties and half-life of the drug delivered.

The efficacy of the treatment of AMD or CNV, can be measured by various endpoints commonly used in evaluating intraocular diseases.

In some embodiments of the invention, there is provided a method for reducing corneal lymphangiogenesis in a subject in need thereof, comprising the steps of: (a) identifying a subject with corneal lymphangiogenesis; and (b) locally administering to the cornea of said subject a composition comprising an effective amount of a variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3, thereby inhibiting the ability of lymphatic vessels to expand within or invade corneal tissue and reducing corneal lymphangiogenesis.

In some embodiments of the invention, there is provided a method for minimizing or preventing corneal lymphangiogenesis in a subject in need thereof, comprising the steps of: (a) identifying said subject at risk of developing lymphangiogenesis onset; and (b) locally administering to the cornea of said subject a composition comprising an effective amount of a variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3 prior to said development, thereby inhibiting the ability of lymphatic vessels to form or expand within, or to invade corneal tissue.

In some embodiments of the invention, there is provided a method for reducing corneal lymphangiogenesis in a subject in need thereof, comprising the steps of: (a) identifying a subject with corneal lymphangiogenesis; and (b) administering to the subject a composition comprising an effective amount of a variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3, thereby inhibiting the ability of lymphatic vessels to expand within or invade corneal tissue and reducing corneal lymphangiogenesis.

In some embodiments of the invention, there is provided a method for minimizing or preventing corneal lymphangiogenesis in a subject in risk thereof, comprising the steps of: (a) identifying said subject at risk of developing lymphangiogenesis onset; and (b) administering to the subject a composition comprising an effective amount of a variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3 prior to said development, thereby inhibiting the ability of lymphatic vessels to form or expand within, or to invade corneal tissue.

According to some embodiments, reduction or prevention of corneal lymphangiogenesis refers to inhibition or suppression of at least 50%, preferably at least 70%, most preferably at least 90% of angiogenesis in a subject non-treated with the composition of the invention. Each possibility represents a separate embodiment of the present invention.

In some embodiments of the invention, there is provided a method for treating diabetes or IBD comprising the steps of administering to a subject in need a composition comprising an effective amount of a variant of Semaphorin 3C which has at least 80%, 90%, 95%, 99% or 100% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and/or wherein said variant has at least one modification in furin-like pro-protein convertase cleavage site 3 consisting of amino acid residues 742-745; and wherein said modification renders said variant resistant to cleavage at said cleavage site 3.

In some embodiments of the invention, there is provided a Semaphorin 3C variant according to the embodiments of the invention for use for reducing corneal lymphangiogenesis in a subject in need thereof.

In some embodiments of the invention, there is provided a Semaphorin 3C variant according to the embodiments of the invention for use for preventing or minimizing corneal lymphangiogenesis in a subject in risk thereof.

According to another embodiment, systemic administration of the composition is through injection. For administration through injection, the composition may be formulated in an aqueous solution, for example in a physiologically compatible buffer including but not limited to Hank's solution, Ringer's solution, or physiological salt buffer. Formulations for injection may be presented in unit dosage forms, for example, in ampoules, or in multi-dose containers with, optionally, an added preservative.

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

According to another embodiment, compositions formulated for injection may be in the form of solutions, suspensions, dispersions or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate or triglycerides.

According to another embodiment, the composition is administered intravenously, and is thus formulated in a form suitable for intravenous administration. According to another embodiment, the composition is administered intra-arterially, and is thus formulated in a form suitable for intra-arterial administration. According to another embodiment, the composition is administered intramuscularly, and is thus formulated in a form suitable for intramuscular administration.

According to some embodiments, the composition is administered through direct injection into a tumor. According to some embodiments, the composition is administered through injection to a tumor's environment. According to some embodiments, the composition is administered by injection to a blood vessel in the tumor's environment. According to some embodiments, the composition is administered by injection into a blood vessel supplying blood to a tumor.

According to certain embodiments, administration systemically is through an enteral route. According to another embodiment, administration through an enteral route is oral administration. According to some embodiments, the composition is formulated for oral administration.

According to some embodiments, oral administration is in the form of hard or soft gelatin capsules, pills, capsules, tablets, including coated tablets, dragees, elixirs, suspensions, liquids, gels, slurries, syrups or inhalations and controlled release forms thereof.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin, for use in a dispenser may be formulated containing a powder mix of the composition of the invention and a suitable powder base, such as lactose or starch.

Solid dosage forms for oral administration include capsules, tablets, pill, powders, and granules. In such solid dosage forms, the composition of the invention is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration may further contain adjuvants, such as wetting agents, emulsifying and suspending agents, and sweetening, flavoring and perfuming agents. According to some embodiments, enteral coating of the composition is further used for oral or buccal administration. The term "enteral coating", as used herein, refers to a coating which controls the location of composition absorption within the digestive system. Non-limiting examples for materials used for enteral coating are fatty acids, waxes, plant fibers or plastics.

According to some embodiments, administering is administering topically. According to some embodiments, the composition is formulated for topical administration.

According to some embodiments, administration of the composition of the invention to a subject in need thereof is by a route selected from the group consisting of: intravenous, intraarterial, transdermal, subcutaneous, via direct injection into a tissue and via direct injection into a tumor. Each possibility represents a separate embodiment of the present invention. According to certain embodiments, administration may be orally.

According to some embodiments, the present invention provides the pharmaceutical composition of the invention for use in treating cancer in a subject. According to some embodiments, the present invention provides the pharmaceutical composition of the invention for use in inhibiting lymphangiogenesis. According to some embodiments, the present invention provides the pharmaceutical composition of the invention for use in inhibiting angiogenesis.

According to some embodiments, the present invention provides a pharmaceutical composition comprising at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site, for use in treating cancer in a subject.

According to some embodiments, the present invention provides a pharmaceutical composition comprising at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site, for use in inhibiting lymphangiogenesis in a subject.

According to some embodiments, the present invention provides a pharmaceutical composition comprising at least one variant of Semaphorin 3C as set forth in SEQ ID NO: 1, wherein the variant comprises at least one modification in furin-like pro-protein convertase (FPPC) cleavage site 2 consisting of amino acid residues 549-552; and wherein the modification renders said variant resistant to cleavage at said cleavage site, for use in inhibiting angiogenesis in a subject.

In some embodiments, the invention further envisages inclusion of a complex of Semaphorin 3C which has at least 80%, 90%, 95%, 99% or 100% sequence identity with the amino acid set forth in SEQ ID NO: 1 or a variant thereof according to the embodiments of the invention where it is attached to proteinaceous (e.g., heterologous amino acid sequence) or non-proteinaceous moieties (e.g., PEG), each of which being capable of prolonging the half-life of the composition while in circulation.

Such a molecule is highly stable (resistant to in-vivo proteaolytic activity, probably due to steric hindrance conferred by the non-proteinaceous moiety) and may be produced using common solid phase synthesis. Further recombinant techniques may still be used, whereby the recombinant peptide product is subjected to in-vitro modification (e.g., PEGylation as further described hereinbelow).

The phrase "non-proteinaceous moiety" as used herein refers to a molecule not including peptide bonded amino acids that is attached to the above-described Semaphorin 3C which has at least 80%, 90%, 95%, 99% or 100% sequence identity with the amino acid set forth in SEQ ID NO: 1 or a variant thereof according to the embodiments of the invention. According to some embodiments the non-proteinaceous moiety may be a polymer or a co-polymer (synthetic or natural). Non-limiting examples of the non-proteinaceous moiety of the present invention include polyethylene glycol (PEG) or derivative thereof, Polyvinyl pyrrolidone (PVP), divinyl ether and maleic anhydride copolymer (DIVEMA); polysialic acid (PSA) and/or poly (styrene comaleic anhydride) (SMA). Additionally, complexes which can protect Semaphorin 3C which has at least 80%, 90%, 95%, 99% or 100% sequence identity with the amino acid set forth in SEQ ID NO: 1 or a variant thereof according to the embodiments of the invention from the environment and thus keep its stability may be used, including, for example, liposomes or micelles. According to some embodiments of the invention, the Semaphorin 3C which has at least 80%, 90%, 95%, 99% or 100% sequence identity with the amino acid set forth in SEQ ID NO: 1 or a variant thereof according to the embodiments of the invention thereof are attached to a non-proteinaceous moiety, which may act as a sustained-release enhancing agent. Exemplary sustained-release enhancing agents include, but are not limited to hyaluronic acid (HA), alginic acid (AA), polyhydroxyethyl methacrylate (Poly-HEMA), glyme and polyisopropylacrylamide Attaching the amino acid sequence component Semaphorin 3C which has at least 80%, 90%, 95%, 99% or 100% sequence identity with the amino acid set forth in SEQ ID NO: 1 or a variant thereof according to the embodiments of the invention to other non-amino acid agents may be by covalent linking or by non-covalent complexion, for example, by complexion to a hydrophobic polymer, which can be degraded or cleaved producing a compound capable of sustained release; by entrapping the amino acid part of Semaphorin 3C which has at least 80%, 90%, 95%, 99% or 100% sequence identity with the amino acid set forth in SEQ ID NO: 1 or a variant thereof according to the embodiments of the invention comprising thereof in liposomes or micelles to produce a complex comprising Semaphorin 3C which has at least 80%, 90%, 95%, 99% or 100% sequence identity with the amino acid set forth in SEQ ID NO: 1 or a variant thereof according to the embodiments of the invention. The association may be by the entrapment of the amino acid sequence within the other component (liposome, micelle) or the impregnation of the amino acid sequence within a polymer to produce the final peptide of the invention.

In some embodiments, the PEG derivative is N-hydroxysuccinimide (NHS) esters of PEG carboxylic acids, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. PEG-maleimide, PEG-vinylsulfone (VS), PEG-acrylate (AC) or PEG-orthopyridyl disulfide may be also used.

Serum albumin can also be engaged in half-life extension through modules with the capacity to non-covalently interact with albumin. In these approaches, an albumin-binding moiety is either conjugated or genetically fused to the therapeutic protein with albumin-binding activity are known from certain bacteria. For example, streptococcal protein G contains several small albumin-binding domains (ABD) composed of roughly 50 amino acid residues (6 kDa). Fusion of an ABD to a protein results in a strongly extended half-life (see Roland E Kontermann, trategies for extended serum half-life of protein therapeutics, Current Opinion in Biotechnology 2011, 22:868-876.

In some embodiments of the invention, the variant of the invention and IgG and/or any other protein that may be used for extending the half-life of the variant of the invention in the serum are linked by a linker. In Some embodiments of the invention, the linker is a sequence of between 2-20 amino acids.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

EXAMPLES

Example 1: Generation of Sema3C Cleavage-Resistant Variants

A polynucleotide construct encoding an un-cleavable variant of Sema 3C was generated in two steps:
1. Site directed mutagenesis was performed on a polynucleotide construct comprising the cDNA of Sema 3C as set forth in SEQ ID NO: 15 in order to generate a construct comprising cDNA encoding for a Sema 3C variant mutated at FPPC cleavage site 2.
2. The 3' of the cDNA encoding the resulting variant was truncated from nucleotide 2215, such that the resulting polynucleotide construct comprised a cDNA encoding for a Sema 3C variant which is mutated at site 2 and has a deletion of site 3 and the ADAMTS1 site.

Site Directed Mutagenesis:

Site directed mutagenesis was performed using the PfuUltraII DNA polymerase (Stratagene), according to the manufacturer's manual. In order to perform site directed mutagenesis each PCR tube contained: 10 ng DNA template (human Sema3C-wt cDNA, as set forth in SEQ ID NO: 15, in a pGEM-T easy plasmid), 1.25 ng of each primer as described below, 5 µl of 10× PfuUltraII DNA polymerase reaction buffer, 2.5 mM dNTPs, 1 µl PfuUltraII DNA polymerase and H$_2$O to a final volume of 50 µl. The PCR program used was: 95° C., 5 minutes, 95° C., 30 seconds, 48° C., 1.5 minute, 72° C., 10 minutes—back to step 2, ×25, 72° C., 5 minutes.

In order to digest the methylated template DNA, 1 µl of the DpnI restriction enzyme was added to each tube following the PCR reaction. Following the restriction digestion, the resulting DNA was transformed into XL-1 Blue competent cells. In order to generate a DNA construct comprising cDNA encoding for a Semaphorin 3C variant having site 2 mutated from RSRR (as set forth in SEQ ID NO: 3) to KSKK (as set forth in SEQ ID NO: 13), three additive rounds of mutagenesis were performed as follows:
1. Step1—mutating FPPC site 2 having the amino acid sequence RSRR (as set forth in SEQ ID NO: 3) to a site having the amino acid sequence RSKR (as set forth in SEQ ID NO: 11), using the following primers and human Sema3C-wt cDNA as template:

```
5'-primer   GGGAAACGGAGGAGCAAAAGACAAGATGTGAGACATGG
                                              (SEQ ID NO: 24)

3'-primer   CCATGTCTCACATCTTGTCTTTTGCTCCTCCGTTTCCC
                                              (SEQ ID NO: 25)
```

2. Step2—mutating the site having the amino acid sequence RSKR (as set forth in SEQ ID NO: 11) to a site having the amino acid sequence KSKR (as set forth in SEQ ID NO: 12), using the following primers and the construct generated in step 1 as template:

```
5'-primer
                                              (SEQ ID NO: 26)
TACCCAACTGGGAAACGGAAGAGCAAAAGACAAGATGTGAGACA
TGG 3'-primer
                                              (SEQ ID NO: 27)
CCATGTCTCACATCTTGTCTTTTGCTCTTCCGTTTCCCAGTTGGGTA
```

3. Step3—mutating the site having the amino acid sequence KSKR (as set forth in SEQ ID NO: 12) to a site having the amino acid sequence KSKK (as set forth in SEQ ID NO: 13), using the following primers and the construct generated in step 2 as template:

5'-primer
(SEQ ID NO: 28)
GGGAAACGGAAGAGCAAAAAACAAGATGTGAGACATGGAAACCC

3'-primer
(SEQ ID NO: 29)
GGGTTTCCATGTCTCACATCTTGTTTTTTGCTCTTCCGTTTCCC

The resulting DNA construct comprised cDNA encoding a Sema 3C variant mutated in site 2, as set forth in SEQ ID NO: 10.

Truncation of the 3' End of Sema3C cDNA (as Set Forth in SEQ ID NO: 32) from Base 2215:

The DNA construct generated in step 3 above was further subjected to a PCR reaction using the following primers:

(SEQ ID NO: 30)
1. 5'-primer CGGGATCCACCATGGCATCGGACAATTTG.
The BamHI restriction site is underlined.

(SEQ ID NO: 31)
2. 3'-primer CGCTCGAGACTATTGATGAGGGCCTTTAACTT.
The XhoI restriction site is underlined.

The resulting PCR product was purified from agarose gel and ligated into a pGEM-T easy plasmid. The product was cut from the pGEM-T easy plasmid using the BamHI and XhoI restriction enzymes and ligated into either an NSPI-myc-6His plasmid or an NSPI-Fc plasmid. The resulting plasmids encoded, respectively:

1. UNCL-Sema3C/myc-6His—a variant of Sema 3C uncleavable in site 2, having a C-terminal deletion comprising site 3 and the ADAMTS1 site and having a C-terminal myc-6His tag. The sequence of the resulting variant is as set forth in SEQ ID NO: 9. The cDNA encoding the resulting variant is as set forth in SEQ ID NO: 23.
2. UNCL-Sema3C/FC—a variant of Sema 3C un-cleavable in site 2, having a C-terminal deletion comprising site 3 and the ADAMTS1 site and having a C-terminal FC tag. The sequence of the resulting variant is as set forth in SEQ ID NO: 8. The cDNA encoding the resulting variant is as set forth in SEQ ID NO: 22.

FIG. 1A depicts wild-type Sema3C (indicated "Sema3C"), having all three FPPC cleavage sites and the basic domain (BD) intact. FIG. 1A further depicts UNCL-Sema3C/FC prepared as described herein above, having site 2 mutated from RSRR to KSKK, having a C-terminal truncation deleting site 3 and the ADAMTS1 site and having a C-terminal FC tag. As can be seen in FIG. 1A, site 1 in UNCL-Sema3C/FC is intact. FIG. 1B shows a western blot staining of conditioned media from HEK293 cells transfected with either an empty expression vector (NC), a construct encoding FC-tagged wild type Sema3C (Sema3C wt) or a construct encoding UNCL-Sema3C/FC (UNCL-Sema3C). As can be seen in FIG. 1B, a western blot using anti-FC antibodies showed that wild type Sema3C is cleaved to a 55 kDa form while UNCL-Sema3C/FC is not.

Example 2: Comparison of the Effect of Truncated Vs. Wild-Type Sema3C on In-Vitro Vessel Formation by Vascular Endothelial Cells In order to examine the effect of uncleavable Semaphorin 3C on angiogenesis, human umbilical vein-derived endothelial cells (HUVECs) were seeded in a liquid laminin/collagen gel (Matrigel). HUVECs seeded in a Matrigel are known to mimic human angiogenesis and to develop vessels within the Matrigel.

The cells were either left un-treated, treated with the N-terminal part of a Sema3C variant cleaved at site 2 and FC-tagged (termed Sema3C-p65-FC, as set forth in SEQ ID NO: 7) or treated with wild-type Sema3C (termed Sema 3C-WT). As can be seen in FIG. 2, the untreated cells and cells treated with Sema3C-p65-FC formed a network of tubes following incubation (FIG. 2B,C,E,F). In contrast, as can be seen in FIG. 2H-I, cells treated with wild-type Sema3C were contracted and failed to form tubes.

Example 3: Semaphorin 3C Induces Contraction of Lymphatic Endothelial Cells

In order to examine the effect of class 3 Semaphorins on lymphangiogenesis the LEC (Lymphatic Endothelial Cells) collapse assay was employed, monitoring the ability of semaphorins to induce LEC collapse. LECs were plated on gelatin coated cover slips (diameter 13 mm, thickness 1 mm), one day before the experiment, so that they would be 50-70% confluent at the day of experiment.

The experiment was initiated by a 25 min incubation of LECs at 37° C. with purified sema3E (1 μg/ml) or conditioned medium of HEK293 cells transfected with an empty vector or a construct encoding wild-type forms of either sema3A, sema3B, sema3C, sema3D, sema3F, sema3G or sema6A. The conditioned media were collected from $6\times10^6$ HEK293 cells 48 hours post-seeding. To verify that the semaphorins used are active, they were tested using a collapse assay on HUVEC (Human Vein Endothelial Cells) or human primary glioblastoma cells (U87, ATCC).

Following incubation, LECs were washed once in PBS and permeabilized in 0.5% Triton-X-100 diluted in 4% PFA for 2 minutes in room temperature. The cells were then fixed by incubation in 4% PFA at room temperature for 25 minutes and then washed 5 times in PBS. The cells were labeled with anti-vinculin antibody and diluted in PBS (1:100) at room temperature for 1 hour (20 μl of diluted antibody for each cover slip). The cells were then washed 3 times in PBS for 5 minutes and labeled with the mixture of anti-mouse Cy3

(secondary antibody for vinculin staining) (1:300) and Alexa Flour 488 Phalloidin (1:100, 2 units/ml) (to visualize actin filaments), diluted in PBS, for 45 minutes at room temperature in the dark (for sema3B, sema3D, sema3G, sema3E, sema6A). Or with Cy2 (1:300) and Phalloidin 570 (1:100, 2 units/ml), for sema3C, sema3F, sema3A, and the empty-vector control. The cells were then mounted using Mowiol mounting media (Calbiochem) on glass slides and photographed 24 hours after mounting using an inverted fluorescent microscope (LSM 700) at a 40× magnification.

As can be seen in FIG. 3, other than Sema 3F (FIG. 3C), previously suggested to inhibit lymphangiogenesis, only Sema 3C conditioned medium induced collapse of the cytoskeleton of Lymphatic Endothelial cells incubated with (FIG. 3B) as opposed to all other tested class 3 Semaphorins or medium conditioned by HEK293 cells transfected by an empty expression vector (FIG. 3A). The results suggest that Sema3C is able to inhibit lymphangiogenesis.

Example 4: Comparison of the Effect of Truncated Vs. Wild-Type Sema3C on Lymphatic Endothelial Cell (LEC) Contraction LECs were plated on gelatin coated cover slips (diameter 13 mm, thickness 1 mm) within 6-well plates, one day before the experiment, so that they would be 50-70% confluent at the day of experiment.

LECs were incubated for 25 min at 37° C. with conditioned medium of HEK293 cells transfected with an empty vector or a construct encoding either FC-tagged wild-type sema3C (termed Sema3C-WT) or FC-tagged Sema3C-p65 variant (Sema3C truncated at site 2, termed Sema3C-p65). The cells were photographed at the time the various conditioned media were added (time zero) and after 1 hour of incubation (1 hour). As can be seen in FIG. 4F, incubation with Sema3C-p65 did not induce LEC contraction, similarly to the control sample (FIG. 4B). Wild-type Sema3C, however, was able to induce LEC contraction (FIG. 4D).

Example 5: Uncleavable Semaphorin 3C Prevents the Formation of Metastasis in Sentinel Lymph Nodes of Tumors Induced in Nude Mice In order to follow cancer cells within mice, LM2-4 cells (derived from highly metastatic MDA-MB-231 breast cancer cells) were infected with lentiviruses directing expression of Tomato-red fluorescent protein. Cells were then infected with empty lenti viruses (control cells) or with lenti viruses directing expression of UNCL-sema3C/Myc, as described in Example 1 (UNCL-Sema3C cells).

Control cells and UNCL-Sema3C cells from exponential cultures were dissociated with trypsin/EDTA, washed with PBS and brought to a concentration of $4 \times 10^7$ cells/ml. Each cell suspension ($2 \times 10^6/0.05$ ml) was inoculated in the right mammary fat pad of a 5-weeks old female NOD mice (n=7). After 31 days, mice were sacrificed and xenografts were resected, weighted and fixed in formalin. Sentinel lymph nodes (mesenteric) and axially lymph nodes were removed and photographed using an Olympus SZX9 fluorescent stereomicroscope to detect tomato red expressing cells that metastasized to the lymph node. All animal experiments were approved by the Animal Care Committee of the Technion, Haifa, Israel.

Tumors that developed from UNCL-Sema3C/Myc-expressing cells were about 40% smaller than tumors that developed from control cells. As can be seen in FIG. 5M, the weight of a tumor induced by UNCL-Sema3C cells (marked "Sema3C") was significantly lower (*=p<0.05) than a tumor induced by control cells (marked "control").

As can be seen in the fluorescent microscope images depicted in FIG. 5, a sentinel lymph node taken from an animal having UNCL-Sema3C/Myc-expressing tumors contained no Tomato-red fluorescent protein expressing cells as opposed to sentinel lymph nodes taken from control animals (FIGS. 5K-L and FIGS. 5E-H, respectively). FIGS. 5A-D and 5I-J depict phase contrast pictures of the sentinel lymph nodes depicted in FIGS. 5E-H and 5K-L, respectively.

Example 6: Uncleavable Semaphorin 3C Reduces the Density of Tumor Associated Lymph Vessels Tumors formed using LM2-4 cells expressing either UNCL-sema3C/Myc or a control construct were formed in mice, as described in Example 5 (six mice in each group). The tumors were extracted as described in Example 5 and embedded in paraffin. In order to visualize the lymph nodes within the tumors, 5 micron thick sections covering the entire cross section of the tumors were stained for the lymph marker Lymphatic Vessel Endothelial Receptor 1 (LYVE-1) using an anti-LYVE-1 polyclonal antibody (Abcam Inc, Cambridge, Mass.) and the peroxidase-based EnVision™ kit (Daco). The area stained in microscopic fields of equal area covering the entire cross sections were determined using the ImagePro morphometric software. As can be seen in FIG. 6, the lymph node area in sections taken from tumors induced by UNCL-Sema3C/Myc expressing cells (marked "UNCL-Sema3C") was significantly lower (**=p<0.01) than the area in section taken from tumors induced by control cells (marked "Control").

Example 7: Uncleavable Semaphorin 3C Reduces Tumor Weight Formed by VEGF-C-Expressing MDA-MB-231 Breast Cancer Cells MDA-MB-231 breast cancer cells were infected with lentivirus expressing human VEGF-C (Vascular Endothelial Growth Factor C) protein. Following selection, a clone expressing high levels of VEGFC was infected with lentiviruses carrying either control or UNCL-sema3C/myc constructs, as described in Example 5. Cells expressing VEGF-C and either a control construct or UNCL-sema3C/myc were dissociated using trypsin/EDTA, washed with PBS and brought to a concentration of $1 \times 10^7$ cells/ml. Each cell suspension ($1 \times 10^6/0.1$ ml) was inoculated subcutaneously at the right flank of a 5-weeks old female Athymic nude mouse (n=6). After 41 days, mice were sacrificed and xenografts were resected, weighted and fixed in formalin. All animal experiments were approved by the Animal Care Committee of the Technion, Haifa, Israel. As can be seen in FIG. 7, the weight of tumors resulting from MDA-MB-231 cells expressing VEGF-C and UNCL-Sema3C/Myc (marked "VEGF-C+Sema3C") was significantly lower (*=p<0.05) than the weight of tumors resulting from cells expressing VEGF-C and the control construct (marked "VEGF-C+Control").

Example 8: Expression of Class-3 Semaphorin Receptors in Cultured Lymphatic Endothelial Cells (LEC) and Cultured Human Umbilical Vein-Derived Endothelial Cells (HUVEC)

In order to assay expression of Class-3 Semaphorin receptors, a real-time PCR analysis was conducted. First, cDNAs from LEC and HUVEC were analyzed by AB StepOne Real-Time PCR system (Applied Biosystems) using a TaqMan Gene Expression Assay Mix (Applied Biosystems) specific for PlexinA1, PlexinA2, PlexinA3, PlexinA4, Plexin D1, NP1 and NP2 (hPlexinA1 HS00413698, hPlexinA2 HS00300697, hPlexinA3 HS00250178, hPlexinA4 HS00297356, hPlexinD1 HS00892410, hNP1 HS00826128, hNP2 HS00187290).

The TaqMan PCR reactions for each gene target were performed in duplicates on cDNA samples. For each 10 μl TaqMan reaction, 2.5 μl (25 ng) cDNA was mixed with 2 μl PCR-grade water, 5 μl 2× TaqMan Universal PCR Master Mix (Applied Biosystems) and 0.5 μl primer mix. The PCR parameters used were: 50° C. for 2 min, 95° C. for 10 min, 40 cycles of 95° C. for 15 s and 60° C. for 1 min. The reference gene human RPLPO (hRPLPO HS99999902), a standard endogenous control from ABI's Taqman gene expression assays, was multiplexed with the target gene for every cDNA template as a quality control measure. The resulting data was analyzed by the RQ Manager Software to obtain a relative quantification based on the arithmetical equation $2^{-\Delta Ct}$, in which $\Delta Ct$ is the normalized signal level in a sample relative to the RPLPO signal.

As can be seen in FIG. 8, LEC express NP2 but not NP1 or Plexin-A4. FIG. 8 further shows that LEC express very high levels of Plexin-A2 as compared to HUVEC (marked "HUE" in FIG. 8).

Example 9: UNCL-Sema3C-Fc Induces Collapse of the Cytoskeleton of Lymphatic Endothelial Cells (LECs)

In order to examine whether the ability of wild-type Sema 3C to induce contraction of LECs is maintained in the cleavage resistant form of Sema3C, LECs were plated on cover slips within 12-well plates. Following 24 hours of incubation, the cells were incubated for 40 minutes at 37° C. with either purified UNCL-Sema3C-FC (SEQ ID NO: 8), purified Sema3C-p65-FC (SEQ ID NO: 7), purified Semaphorin 3E or elution buffer. The cells were then washed, fixed and stained with Phalloidin and an anti-Vinculin antibody, as described in Example 3. The cells were visualized using an inverted fluorescent microscope (LSM 700) at a 400× magnification.

As can be seen in FIG. 9, UNCL-Sema3C-FC was able to induce cytoskeleton collapse in LECs (B), while cells incubated with elution buffer (A), Semaphorin 3E-FC (B) or Sema3C-p65-FC (D) were not able to induce cytoskeleton collapse. This result suggests that the ability of wild-type Semaphorin 3C to induce LEC collapse is derived from the activity of the uncleaved form of Sema 3C.

Figure 10A:
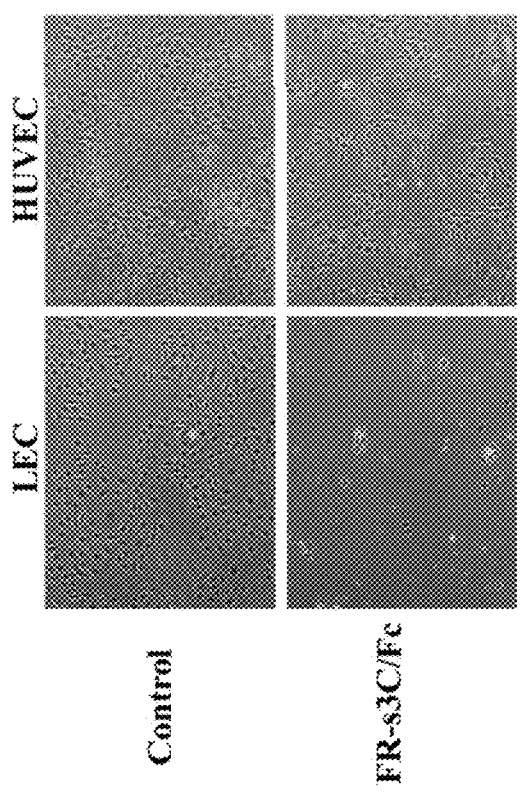
Figure 10B:
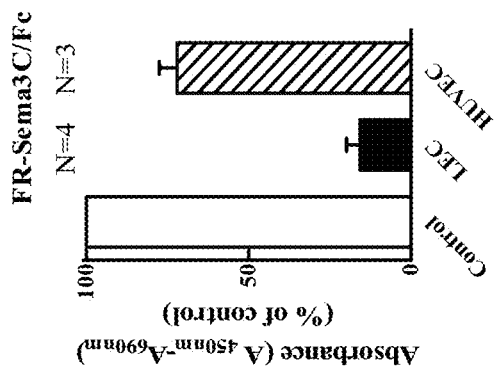

Example 10: FR-sema3C/Fc (Also Termed Herein UNCL-Sema3C/Fc-) Strongly Inhibits the Proliferation of LEC and VEGF-C-Induced Signal Transduction To better characterize FR-sema3C, the effect of purified FR-sema3C/Fc on the proliferation of HUVEC and LEC was assessed. HUVEC ($2 \times 10^4$ cells/well) or LEC ($4 \times 10^4$ cells/well) were seeded in LEC medium in the presence or absence of semaphorins (2 μg/ml). Cells were photographed after 72 h. FR-sema3C/Fc inhibited strongly the proliferation of LEC, and the cells eventually died. In contrast, although FR-sema3C/Fc inhibited the proliferation of HUVEC, the inhibition did not result in cell death and was much less potent than the inhibition of LEC proliferation (FIG. 10A). These results were confirmed by WST-1 proliferation kit. LEC and HUVEC were seeded in fibronectin-coated 96 well dishes and the effect of FR-sema3C/Fc (2 μg/ml) on their proliferation was measured according to the instructions of the vendor. Shown is the average of N independent experiments (FIG. 10B).

Figure 10C:
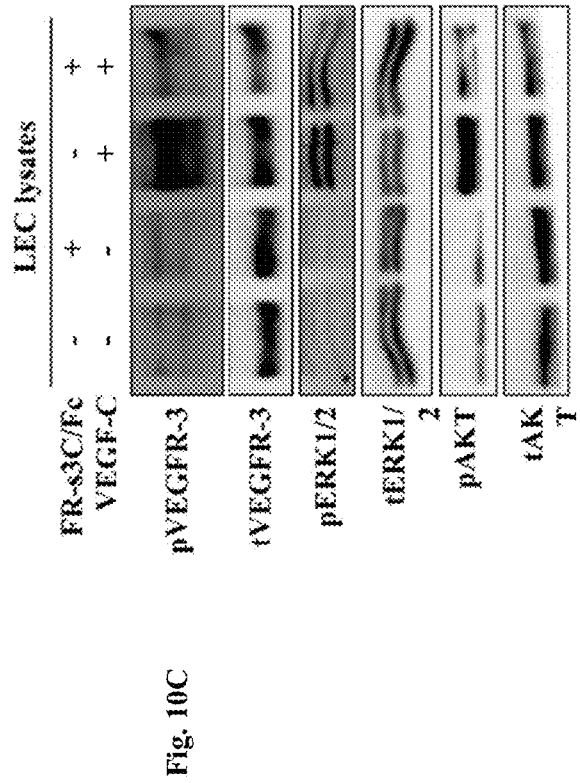

VEGF-C promotes the proliferation of LEC and is a potent lymphangiogenic factor. Accordingly, the effect of FR-sema3C/Fc on VEGF-C-induced signaling in LEC was assessed. LEC were grown to 90% confluence in growth medium and then shifted to LEC medium lacking growth factors and containing 0.5% FCS for 16 h. The cells were then incubated with vehicle or FR-sema3C/Fc (1 μg/ml) for 15 minutes followed by a 10 min stimulation with VEGF-C (200 ng/ml). VEGFR-3, ERK1/2 and AKT phosphorylation levels were determined essentially as previously described for ERK1/2 phosphorylation. Stimulation by FR-sema3C/Fc inhibited VEGF-C-induced phosphorylation of the VEGFR-3 receptor of LEC (Tyr-1230/1231), and also inhibited VEGF-C-induced phosphorylation of ERK1/2 and Akt (FIG. 10C). These results suggest that FR-sema3C may inhibit the proliferation of LEC by inhibition of VEGF-C signaling and that FR-sema3C may compete with VEGF-C for binding to the VEGF-C co-receptor neuropilin-2 to inhibit the phosphorylation of VEGFR-3.

Figure 10E:
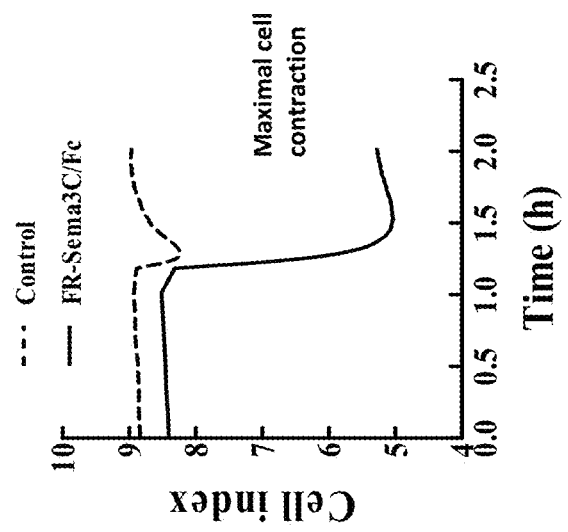
Figure 10D:
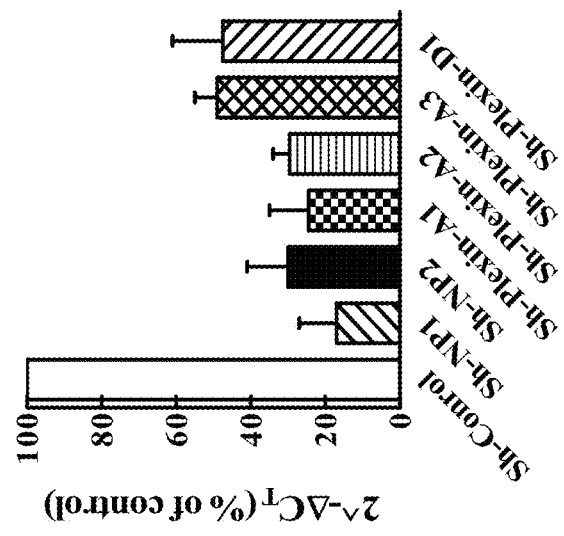

To determine the relative contribution of the different neuropilins and plexins of LEC to FR-sema3C signal transduction, the expression of these receptors in LEC was silenced (FIG. 10D), and the effects on FR-sema3C/Fc-induced cell contraction were quantified using the xCELLigence dual plate (RTCA) machine as shown in FIG. 10E. The inhibition of plexin expression with shRNA expressing lentiviruses was done by MISSION shRNA plasmids directing expression of various shRNAs that were purchased from Sigma Aldrich. The production of the lentiviruses in HEK293FT cells was performed as previously described (Varshaysky et al., 2008). LEC were seeded in 35 mm dishes, infected with the different silencing lentiviruses for 16 hours. 72 hours after infection the cells were used for contraction experiments and RNA silencing was detected by qRT-PCR. The plasmids purchased were: PlexinA1—TRCN0000078734, PlexinA2—TRCN0000061499, PlexinA3—TRCN0000047678, PlexinA4—TRCN00000-78683, PlexinD1—TRCN0000061548, NP1—TRCN0000-063526, NP2—TRCN0000063312 (Sigma Aldrich).

Figure 10F:
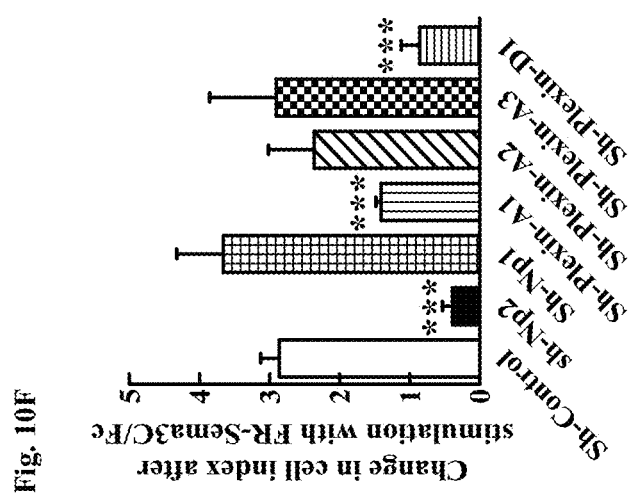

FR-sema3C/Fc-induced contraction of the actin cytoskeleton of the LEC was strongly and significantly inhibited in LEC silenced for the expression of either neuropilin-2 ($P<0.001$), or plexin-D1 ($P<0.001$). FR-sema3C/Fc-induced contraction was also inhibited by plexin-A1 silencing although somewhat less potently ($P<0.001$) while the silencing of neuropilin-1, and of the other plexins had no effect (FIG. 10F).

Figure 11A:
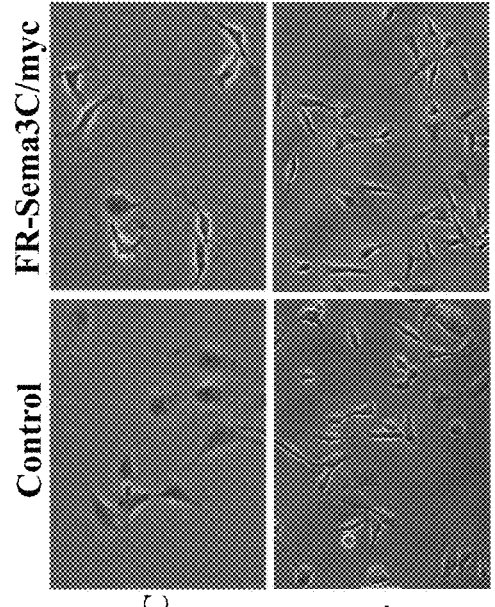
Figure 11B:
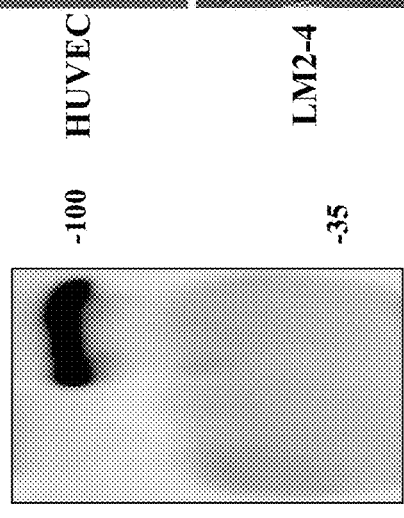
Figure 11C:
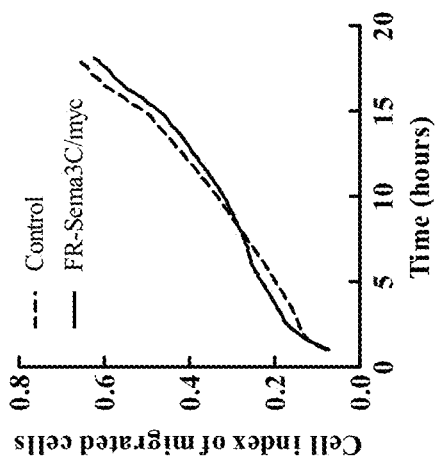
Figure 11D:
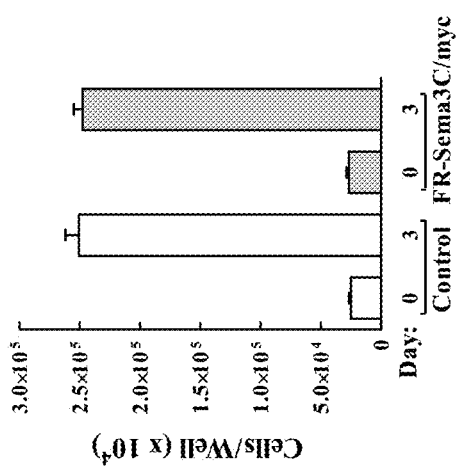

Example 11: FR-sema3C (Also Termed Here UNCL-Sema3C) does not Affect the Proliferation or Migration of LM2-4 Breast Cancer Cells but Strongly Inhibits the Progression of Tumors Derived from these Cells LM2-4 breast cancer cells were derived from triple negative MDA-MB-231 breast cancer cells by repeated isolation of metastasized cells from lungs. Recombinant tomato red RFP was expressed in them and in addition either empty expression vector (control) or FR-sema3C/myc. Conditioned medium from FR-sema3C/myc expressing LM2-4 cells contained almost exclusively full-length FR-sema3C/ myc (FIG. 11A). FR-sema3C/myc was biologically active and induced the contraction of HUVEC (FIG. 11B). However, FR-sema3C/myc failed to induce contraction of LM2-4 cells (FIG. 11B) nor expression of FR-sema3C/myc in the cells inhibit their proliferation or migration (FIGS. 11C & 11D). LM2-4 cells express neuropilin-1 and plexin-D1 but express very little neuropilin-2 which may perhaps explain why they do not respond to FR-sema3C/Fc (FIG. 11E). It is noted that FR-sema3C/myc is identical to FR-sema3 C/myc 6 His.

Nevertheless, even though the expression of FR-sema3C/myc in LM2-4 cells did not change their behaviour in-vitro, expression of FR-sema3C/myc inhibited significantly (P=0.009) the development of tumors from these cells following their implantation in the mammary fat pads of scid/nod mice (FIG. 12A). Tomato red RFP expressing LM2-4 cells infected with empty lentiviral vector (control) or with lentiviruses directing expression of FR-sema3C/myc were washed, suspended in 50 µl of PBS and injected into the mammary fat pads of 6-7 week-old female scid/nod mice ($2\times10^6$ cells/mouse). Tumor size was monitored once a week. After 30 days, tumors and lymph nodes were excised and weighted. All the animal experiments were approved by the Technion ethics committee.

Figure 12F:
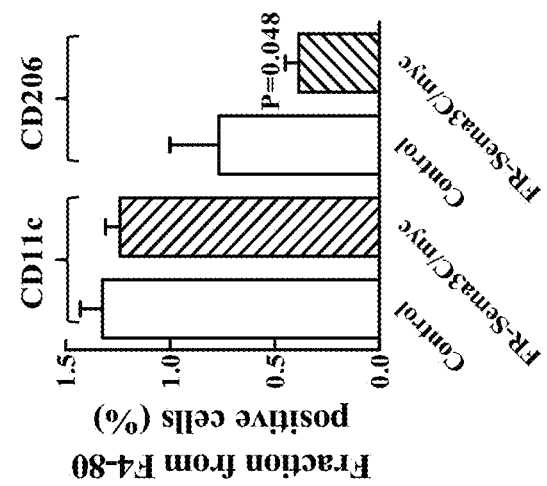
Figure 12G:
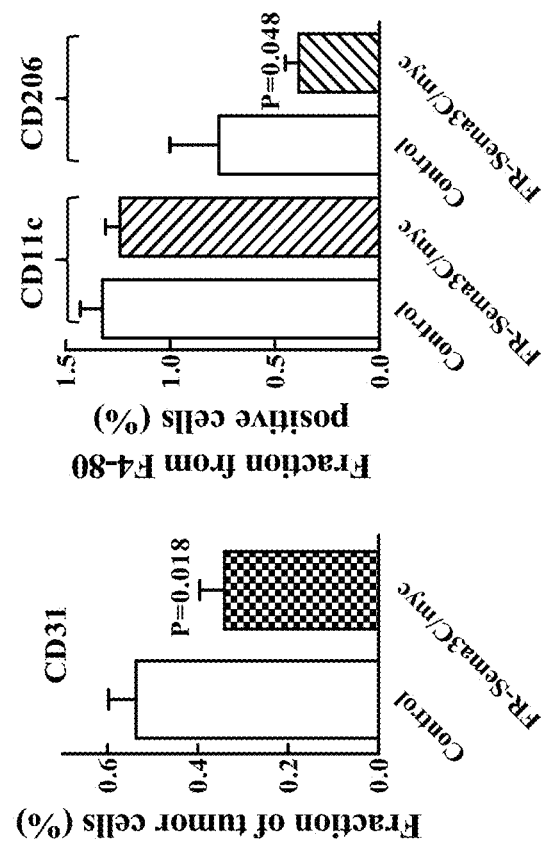

The density of lymph vessels in the primary tumors that developed from FR-sema3C/myc expressing cells was significantly lower (about ~50% lower, P=0.05) as compared to the density of lymph vessels in tumors that developed from control cells (FIGS. 12B & 12C), indicating that FR-sema3C/myc inhibits tumor lymphangiogenesis. In addition, tumors derived from FR-sema3C/myc-expressing LM2-4 cells also contained about half the density of blood vessels (P=0.05) as revealed by the staining of tumor sections with antibodies directed against CD31 (FIGS. 12D & 12E) and by FACS analysis (P=0.0018) (FIG. 12F) suggesting that FR-sema3C also functions as an inhibitor of tumor angiogenesis, which may explain why these tumors were smaller. Notably, the density of blood vessels in control tumors was about 10-fold higher than the density of lymph vessels. The lymph vessels in the control tumors and in the tumors that developed from FR-sema3C/myc expressing cells were not present in necrotic regions but were present in all the other areas of the tumors. The concentration of tumor-associated M1 and M2 macrophages using FACS analysis of single cell suspensions prepared from excised tumors was also determined. These experiments indicate that the concentration of the F4-80+/CD206+ positive M2 macrophage subpopulation is significantly reduced by about 50% in the FR-sema3C/myc expressing tumors (P=0.048), while the concentration of F4-80+/CD11-C+M1 subpopulation was not altered (FIG. 12G).

The proper axillary, lumbar aortic, and subiliac lymph nodes from mice harbouring tumors derived from control and FR-sema3C/myc expressing LM2-4 cells were excised. Metastases in excised lymph nodes were detected using the IVIS-200 imaging system (FIG. 13A). The presence of metastases in lymph nodes was also verified by staining lymph node sections with antibodies directed against human class-1 HLA (FIG. 13B). While all the mice harbouring tumors derived from control cells developed metastases in their lymph nodes, only 26% of the mice harbouring tumors derived from FR-sema3C/myc expressing cells had lymph nodes that contained detectable metastases (FIG. 13C). Only 19% of the lymph nodes excised from mice harbouring FR-sema3C/myc expressing tumors contained detectable metastases while 70% of the lymph nodes excised from mice harbouring control tumors contained metastases. Furthermore, the average size of metastases found in lymph nodes of mice harbouring FR-sema3C/myc expressing tumors was only 15% of the average size of metastases found in lymph nodes derived from mice harbouring control tumors (P<0.001) (FIG. 13D). These results were obtained from three independent experiments. Taken together, these results suggest that FR-sema3C inhibits metastasis to lymph nodes.

Example 12: Use of FR-sema3C (Also Termed Here UNCL-Sema3C) in Eye Diseases

Experimental Procedures:
Methods and Materials

Recombinant $VEGF_{165}$ and bFGF were produced and purified as previously described [see Tessler S, Neufeld G (1990) Basic fibroblast growth factor accumulates in the nuclei of various bFGF-producing cell types. J Cell Physiol 145: 310-317, and Cohen T, Gitay-Goren H, Neufeld G, Levi B-Z (1992) High levels of biologically active vascular endothelial growth factor (VEGF) are produced by the baculovirus expression system. Growth Factors 7: 131-138]. Recombinant PDGF-BB, recombinant HGF and recombinant EGF were purchased (Recombinant human PDGF-BB, recombinant human HGF and recombinant human EGF, PeproTech, Rocky Hill, N.J., USA). Human FR-sema3C was produced as previously described [see Mumblat Y, Kessler O, Ilan N, Neufeld G (2015) Full length semaphorin-3C functions as an inhibitor of tumor lymphangiogenesis and tumor metastasis. Cancer Res 75: 2177-2186]. The elution buffer (100 mM glycine, 24 mM Tris, pH-7.2) was injected as vehicle in in-vivo experiments. Recombinant human Sema-3C was purchased from R&D systems, Minneapolis, Minn., USA. Aflibercept (Eylea™) was purchased from Regeneron Pharmaceuticals, Inc., Tarrytown, N.Y., USA. Anti-phospho-ERK1/2 (sc-7383), anti-sema3C (sc-27796), anti-total ERK1/2 (sc-153), anti-Akt (sc-5298), anti-pFAK$^{125}$ (Tyr397) (sc-11765) and anti-FAK$^{125}$ antibodies (sc-932) were from Santa Cruz Biotechnology, Dallas, Tex. U.S.A. Anti-Phospho-p38 MAP Kinase (Th180/Tyr182) (#9211), antibodies to p38-MAPK (#9212), and antibodies to phospho AKT (Ser473) were from Cell Signaling Technology, Danvers, Mass., USA. FITC-dextran (Fluorescein isothiocyanate-dextran, $2\times10^6$ kDa) and Anti-Protein Kinase-Cα (PKCα) were from Sigma-Aldrich, St. Louis, USA. Isolectin IB4-594 was from Alexa Fluor, Molecular probes, Eugene, USA. The antibody to Glial Fibrillary Acidic Protein (GFAP) was from Millipore, Billerica, Mass., USA. Alexa Fluor® 594 Donkey Anti-Mouse IgG (H+L) was from Life Technologies-Molecular Probes, Carlsbad, Calif., USA. Cy3-Affinipure Goat Anti-Rabbit IgG (H+L) was from Jackson ImmunoResearch Laboratories, Inc., West Grove, Pa., USA. The in situ cell death detection kit, TUNEL, was from Roche Diagnostics, Mannheim, Germany Phosphorylation Assays Human umbilical vein derived endothelial cells (HUVEC) were isolated, and cultured as previously described [see Neufeld G, Gospodarowicz D (1988) Identification of the fibroblast growth factor receptor in human vascular endothelial cells. J Cell Physiol 136: 537-542] and grown to 90% confluence. The cells were incubated overnight in growth medium containing 2% FCS. FR-Sema3C/Fc (2 µg/ml) or vehicle was then added and after ten minutes at room temperature, VEGF (30 ng/ml), bFGF (5 ng/ml), PDGF-BB (50 ng/ml), HGF (50 ng/ml), or EGF (50 ng/ml) were added, and after ten more minutes, the cells were lysed. ERK1/2, p38 MAPK, FAK$^{125}$ and AKT phosphorylation levels were then determined essentially as previously described using western blot analysis followed by quantification of the intensity of stained bands using an Imagequant Las 4000 machine [see Guttmann-Raviv N, Shraga-Heled N, Varshaysky A, Guimaraes-Sternberg C, Kessler O, Neufeld, G (2007) Semaphorin-3A and Semaphorin-3F Work Together to Repel Endothelial Cells and to Inhibit Their Survival by Induction of Apoptosis. J Biol Chem 282: 26294-26305].

Animals

C57 black mice were obtained from the Jackson Laboratory, USA.

Induction and Quantification of CNV and Administration of Therapeutics

C57 black mice at ages between 6-10 weeks were anesthetized by intramuscular ketamine hydrochloride injection at 80 mg/kg and xylazine at 16 mg/kg. For all procedures, 1% tropicamide and 2.5% phenylephrine hydrochloride were administered. After receiving anaesthesia and undergoing pupillary dilation, the animals were positioned before a slit lamp. The fundus was visualized using a microscope slide coverslip coated with 2.5% hypromellose ophthalmic demulcent solution which was held on the mouse cornea and served to subtract the optics of the cornea and lens for optimal view of the retina and spots of the laser lesions. Four laser burns were performed at equal distances around the optic discs of both eyes of C57 black mice using a Novus Spectra ophthalmic laser (Lumenis, Inc., Santa Clara, Calif., USA) to induce CNV. Burns were performed for 0.05 seconds at 250 mW. The burns were observed to produce an acute vapour bubble, indicating rupture of Bruch's membrane. FR-Sema3C/Fc (50 ng or 100 ng), aflibercept (5 µg) or vehicle alone were administered in a volume of 2 µl by intravitreal injection immediately after laser photocoagulation. The eyes of the mice were decompressed by inserting a 30G needle through the conjunctiva and sclera 1 mm behind the limbus. A UMP3 Micro injector equipped with a Nanofil syringe of 10 µL and 33G blunt needle (Word precision instruments, Sarasota, Fla., USA) was used for injection. The posterior segment was evaluated immediately after injection to confirm placement of the drug into the vitreous cavity and for ocular perfusion. After a week the animals were anesthetised. The mouse right atrium was cut and the vascular system perfused for three min with 0.5 ml/min of PBS through the left ventricle with assistance of a perfusion pump, followed by injection of 1.5 mL PBS containing 50 mg/mL fluorescein-labeled dextran. The eyes were removed, eye balls were enucleated carefully and the enucleated eyes fixed overnight in 4% para-formaldehyde (PFA) at 4° C. After rinsing in PBS, the cornea, iris and lens were excised, the eye cup was unfolded, and the neural retina peeled away from the underlying retinal pigment epithelium (RPE). The RPE/choroid/sclera complex was flat-mounted onto a slide with the RPE side facing up. A laser spot with green vessels was scored as CNV-positive, and a laser spot lacking green vessels was scored CNV-negative. Stained vessels were then visualized using a Zeiss Axio Imager M2 system equipped with Apotome, and attached to AxioCam and AxioVision cameras. Each laser lesion site was individually evaluated and photographed at 10× magnification. The area of stained blood vessels that invaded laser burns was then measured using the free hand selection tool of the Axiovision 4.8 microscopy software and expressed in square micrometers ($\mu m^2$). The mean area of invading blood vessels per laser burn was determined from eight separate laser burns that were performed in both eyes. The means obtained from individual mice within an experimental group were then compared.

For Isolectin-$IB_4$ staining animals were euthanized, eyes balls were enucleated and fixed overnight in 4% paraformaldehyde. Retinas were collected and the underlying retinal pigment epithelium (RPE) was exposed as described above. The retinas and the eye cups were incubated in PBS containing 0.5% triton for 5 h at room temperature. Eyecups and retinas were then incubated with alexa fluor 594 conjugated Isolectin-IB4 (10 µg/ml) essentially as described [see Brown D M, Michels M, Kaiser P K, Heier J S, Sy J P, Ianchulev T (2009) Ranibizumab versus verteporfin photodynamic therapy for neovascular age-related macular degeneration: Two-year results of the ANCHOR study. Ophthalmology 116: 57-65]. The eyecups and retinas were flat-mounted onto a slide and stained vessels visualized using a Nikon Eclipse E-600 fluorescent microscope and photographed. The area of stained blood vessels that invaded laser burns was then determined as described above.

Optokinetic Reflex (OKR) Measurements

Visual function was assessed using a non-invasive Opto-Motry optokinetic testing system (Cerebral Mechanics, Lethbridge, AB, Canada, USA), following the procedures described and validated previously [see Prusky G T, Alam N M, Beekman S, Douglas R M (2004) Rapid quantification of adult and developing mouse spatial vision using a virtual optomotor system. Invest Ophthalmol Vis Sci 45: 4611-4616]. Briefly, mice standing unrestrained on a central platform tracked a rotating grating with reflexive head movement behavior. Testing was initiated by projecting a grating of low spatial frequency (0.042 cycles/degree (c/d)), rotating clockwise for left eye measurement or counter clockwise for right eye measurement at 12 degrees/second at maximum 100% contrast. The threshold of maximum spatial frequency that the mouse could track was then determined for each eye.

Electroretinogram (ERG) Measurements

ERG measurements were conducted essentially as previously described [see Scalabrino M L, Boye S L, Fransen K M, Noel J M, Dyka F M, Min S H, et al (2015) Intravitreal delivery of a novel AAV vector targets ON bipolar cells and restores visual function in a mouse model of complete congenital stationary night blindness. Hum Mol Genet 24: 6229-6239]. After overnight dark adaptation, mice were anesthetized using ketamine (80 mg/kg) and xylazine (16 mg/kg). Eye drops (1% tropicamide and 2.5% phenylephrine HCl, and 1% proparacaine HCl) were used to dilate the pupils and to anesthetize the corneal surface. A pair of gold-wire contact lens electrodes was used to record ERGs from each corneal surface. These active leads were referenced to a needle electrode placed subcutaneously between the eyes. A second needle electrode placed in the tail served as the ground lead. ERGs were recorded using an LKC (Gaithersburg, Md., USA) UTAS E-3000 signal averaging system. Responses evoked by ganzfeld strobe flash stimuli were band-pass filtered (0.03-1000 Hz), amplified, averaged and stored. In each recording session, we began with scotopic ERG responses to low-luminance stimuli and increased flash luminance as the session proceeded. Stimuli were presented in order of increasing luminance and ranged in flash luminance from −3.3 to 1.1 log cd s/$m^2$. After the recordings of scotopic ERG responses were complete, cone ERGs were isolated for measuring photopic ERG responses by superimposing stimuli upon a steady adapting field (20 cd/$m^2$). Flash luminance ranged from −0.8 to 1.2 log cd s/$m^2$. All procedures were performed under dim red light, and the mice were kept on a heating pad to maintain a constant body temperature during the ERG recording. The a-wave amplitude was measured from baseline to the trough of the a-wave, whereas the b-wave was measured from the trough of the a-wave to the peak of the b-wave

TUNEL

TUNEL was performed essentially as previously described [see Feit-Leichman R A, Kinouchi R, Takeda M, Fan Z, Mohr S, Kern T S, et al (2005) Vascular damage in a mouse model of diabetic retinopathy: relation to neuronal and glial changes. Invest Ophthalmol Vis Sci 46: 4281-4287]. Retinas treated with DNase were used as a positive control.

Histology and Immunocytochemistry

Eyes were dissected from euthanized mice, fixed in 4% paraformaldehyde (PFA) overnight at 4° C., embedded in paraffin and sectioned into 7 μm sections. haematoxylin and eosin (H&E) staining was performed as previously described [see Lu H, Lu Q, Gaddipati S, Kasetti R B, Wang W, Pasparakis M, et al (2014) IKK2 inhibition attenuates laser-induced choroidal neovascularization. PLoS ONE 9: e87530]. For immunohistochemistry eye cups were fixed in 4% PFA at 4° C. for one hour followed by consecutive one hour incubations in 5%, 10% and 15% sucrose followed by overnight incubation in 20% sucrose at 4° C. The eyecup were then embedded in OCT and sectioned into 15-μm thick sections along the vertical meridian using a cryostat. Sections were washed three times for five minutes in PBS pH 7.4, and incubated in non-immune serum (4% Goat serum, 0.01% Tween 20, PBS 0.1 M). Sections were then incubated overnight at 4° C. with anti-Glial Fibrillary Acidic Protein (GFAP) antibodies at a 1:100 dilution, or with anti-PKCα at a 1:100, rinsed three times in PBS and incubated respectively for 2 h with a donkey anti mouse Alexafluor 594 labeled antibody or with Cy3 conjugated goat anti-rabbit antibody followed by two washes with PBS. Slides were counterstained with DAPI, mounted, and photographed using a Nikon Eclipse E-600 fluorescent microscope.

Statistical Analysis

The one tailed Mann-Whitney test was used to assess the effects of FR-sema3C on growth factor-induced ERK1/2 phosphorylation. To assess the effects of FR-sema3C on CNV-induced by laser photocoagulation, the mean area of invading blood vessels per laser burn was determined from eight separate laser burns that were performed in both eyes. The means obtained from individual mice within an experimental group were then compared and evaluated for statistical significance using one way ANOVA followed by Bonferroni's multiple comparison post test. The statistical significance of the OKR and ERG test results was assessed using student's t-test. The following designations were used in the figures: *: $p<0.05$, **: $p<0.01$ and non-specific: ns.

Adherence to ARVO Regulations

This study adhered to ARVO Statement for the use of Animals in ophthalmic and vision research and was approved by the committee for animal experiments at the Faculty of Medicine of the Technion and by the institutional animal care and use committee, the animal care committee at the University of Louisville.

Experimental Results:

FR-Sema3C Inhibits VEGF and PDGF-BB Signal Transduction in Endothelial Cells

Figure 14B:
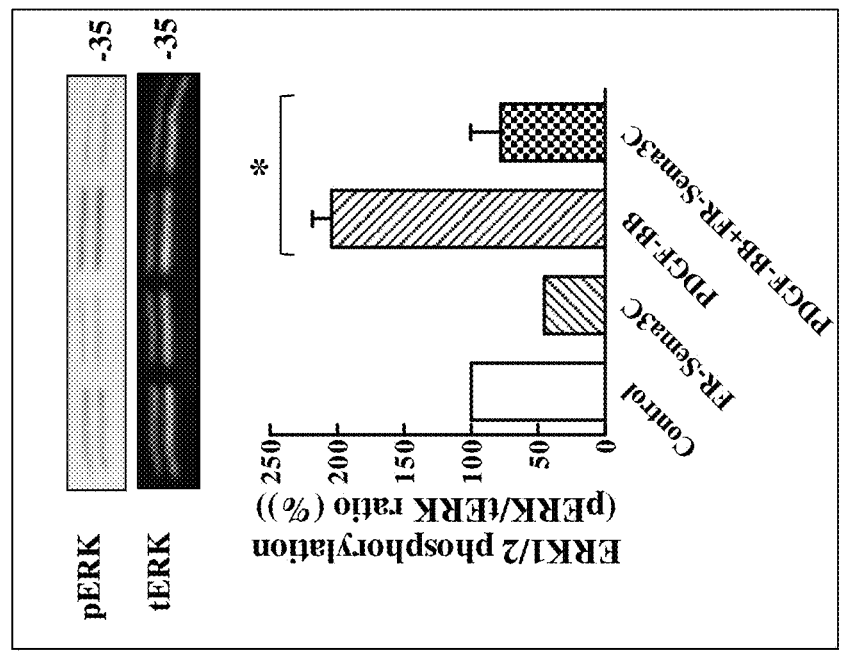
Figure 14A:
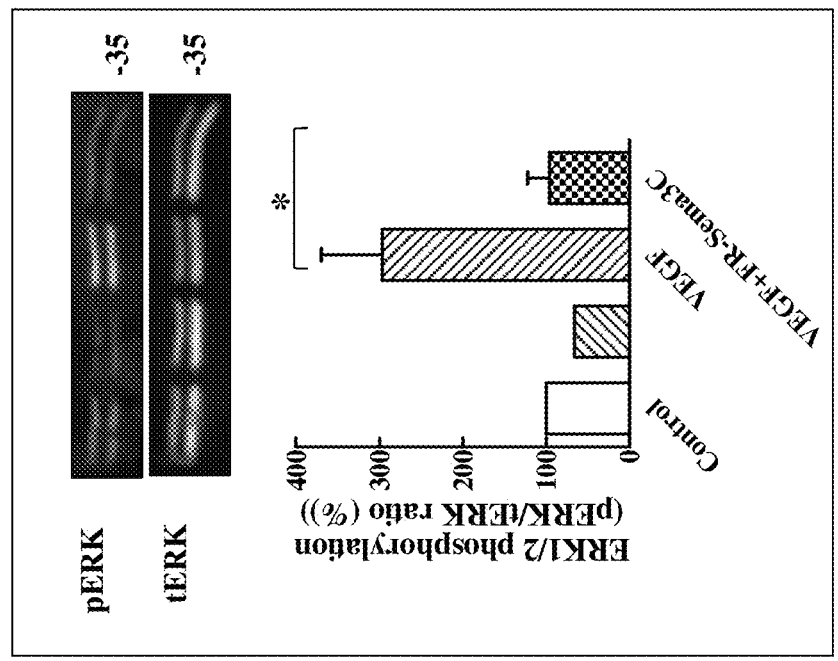
Figure 14C:
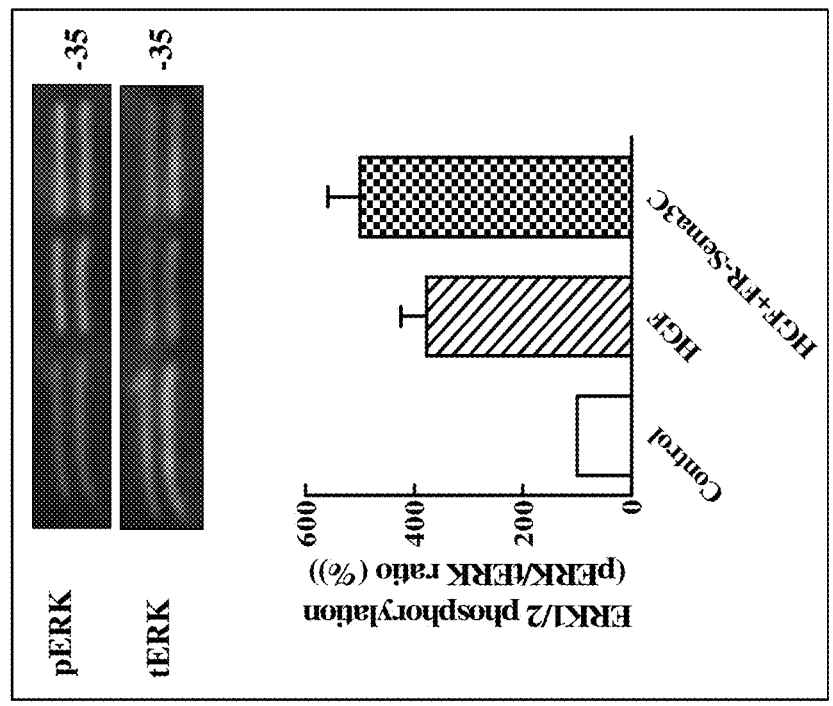
Figure 14D:
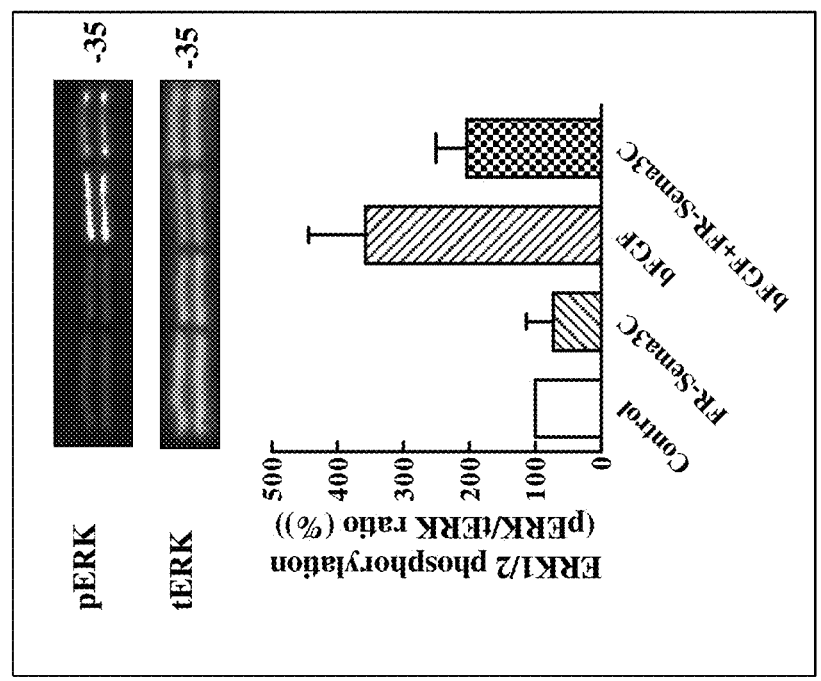
Figure 14E:
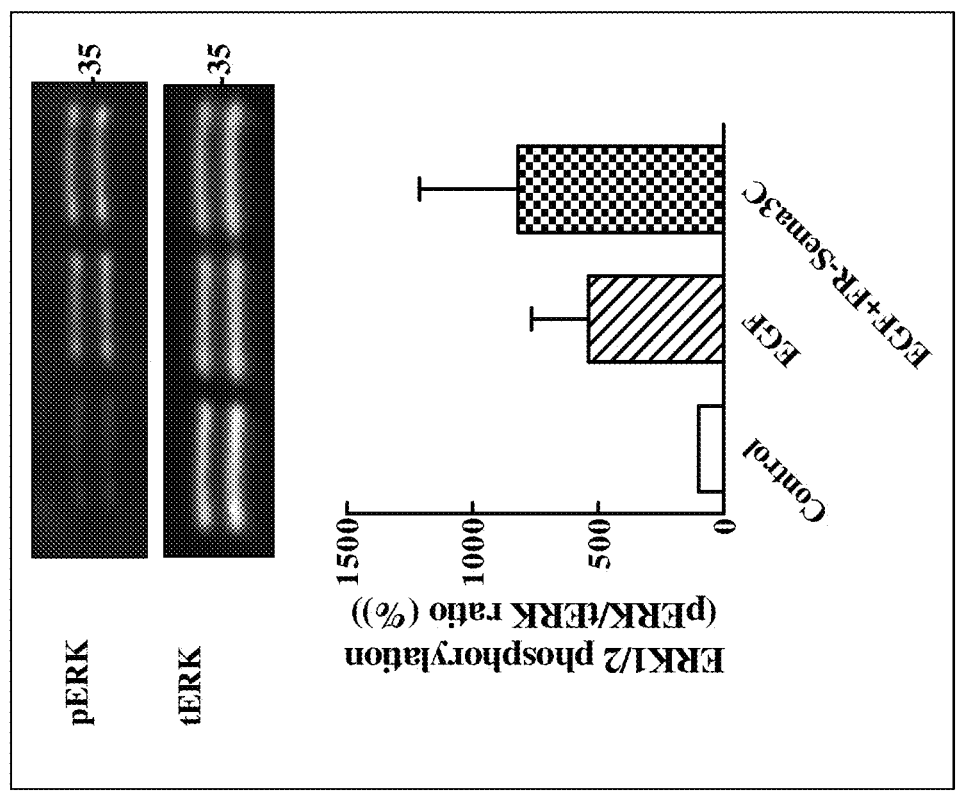
Figure 18B:
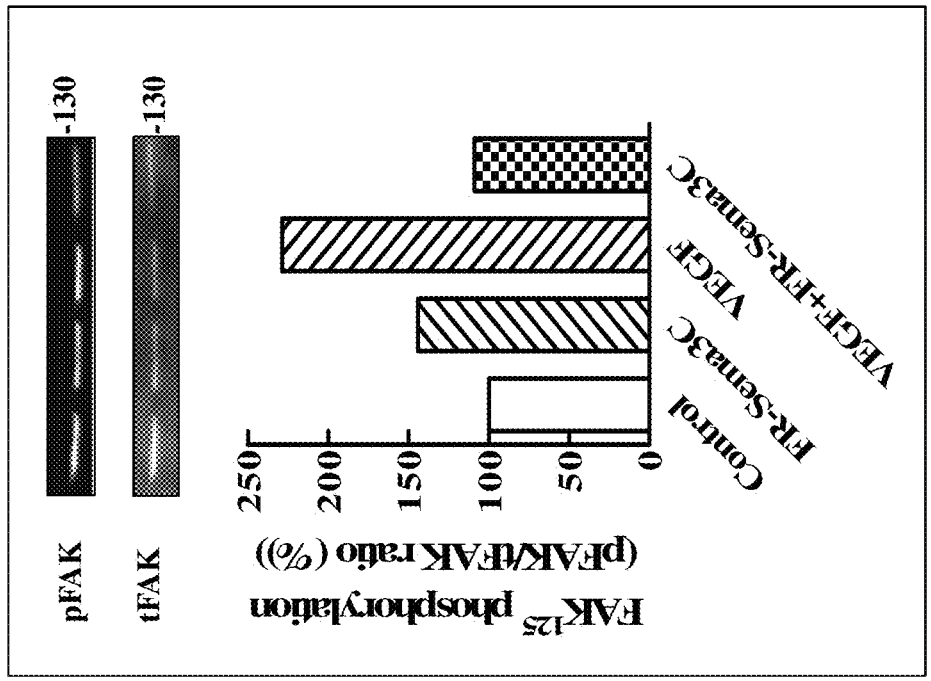
Figure 18A:
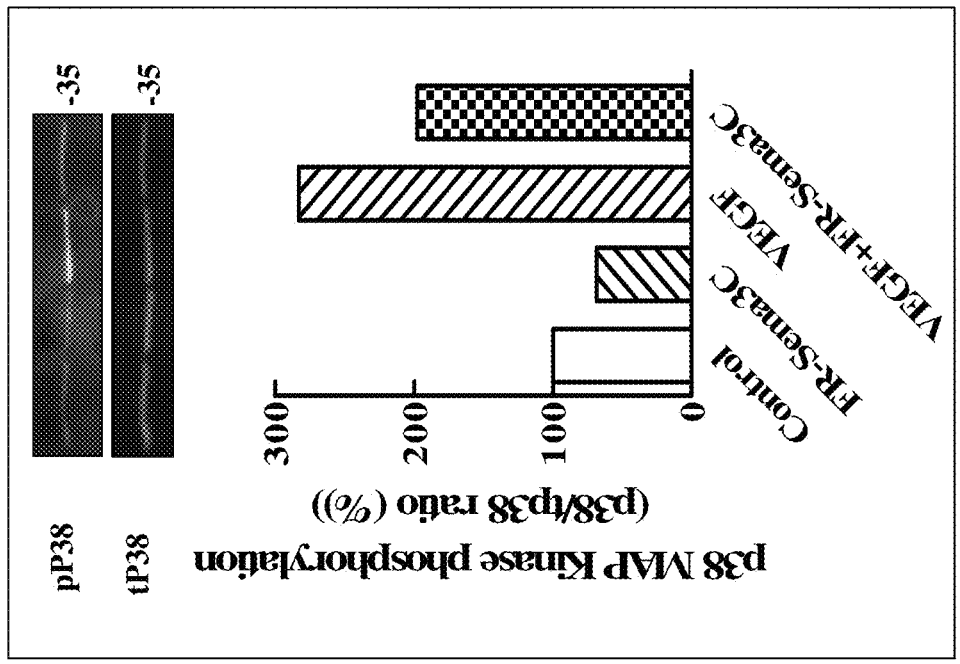
Figure 18D:
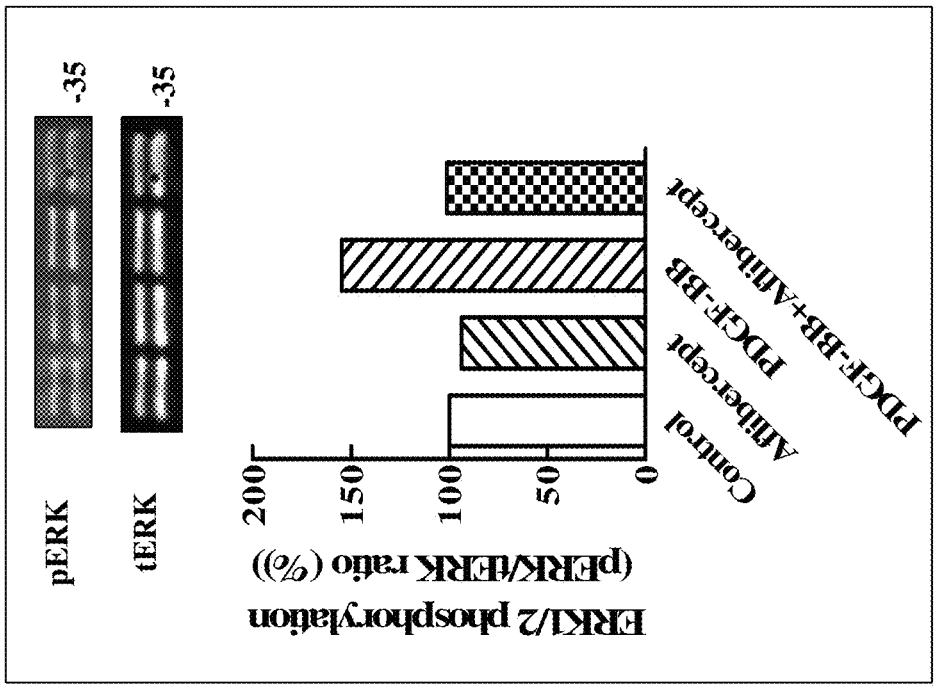
Figure 18C:
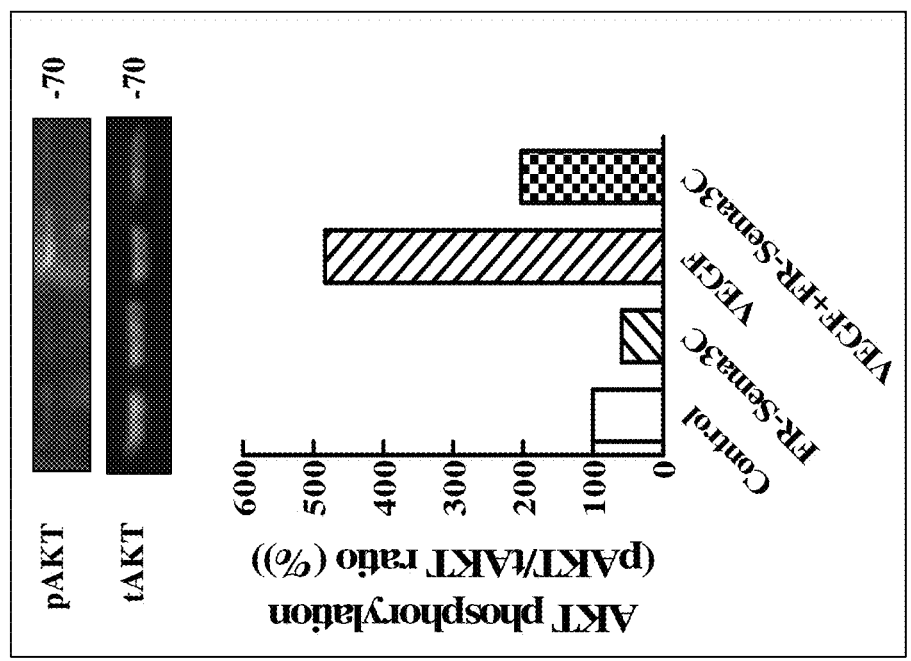
Figure 18E:
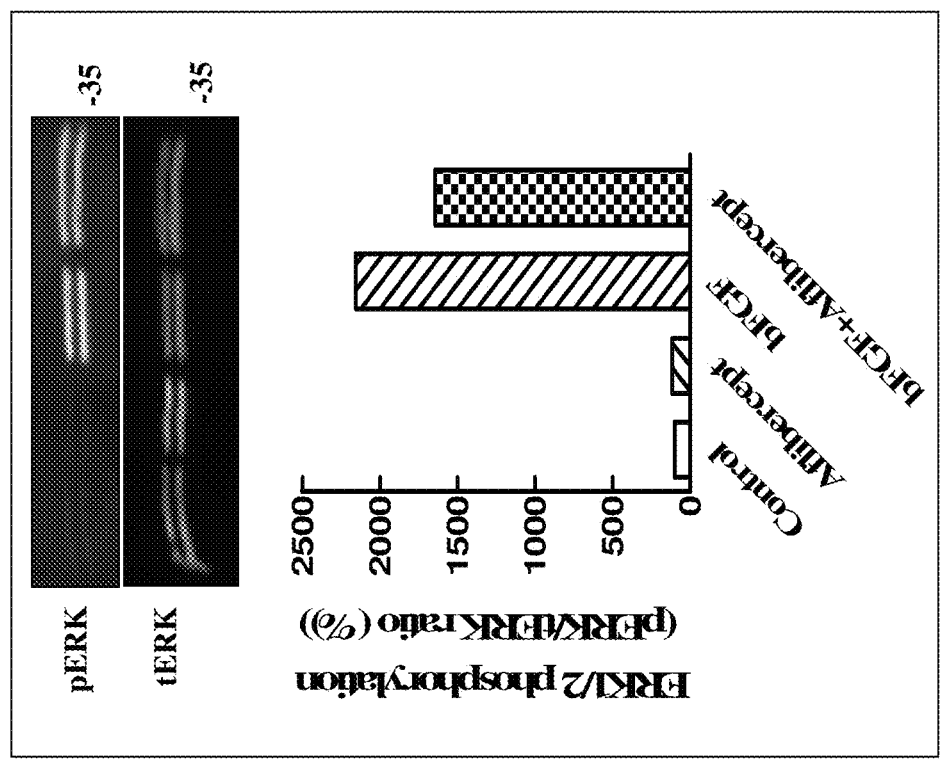

It has previously been determined that FR-sema3C inhibits signal transduction by the angiogenic and lymphangiogenic factor VEGF-C and that it inhibits tumor angiogenesis [see Mumblat Y, Kessler O, Ilan N, Neufeld G (2015) Full length semaphorin-3C functions as an inhibitor of tumor lymphangiogenesis and tumor metastasis. Cancer Res 75: 2177-2186, and Tammela T, Enholm B, Alitalo K, Paavonen K (2005) The biology of vascular endothelial growth factors. Cardiovasc Res 65: 550-563]. Sema3C binds to the neuropilin-1 and neuropilin-2 receptors which also function as essential co-receptors for several VEGF family members and is thus expected to inhibit VEGF signal transduction [see Gitler A D, Lu M M, Epstein J A (2004) PlexinD1 and Semaphorin Signaling Are Required in Endothelial Cells for Cardiovascular Development. Dev Cell 7: 107-116 and Lampropoulou A, Ruhrberg C (2014) Neuropilin regulation of angiogenesis. Biochem Soc Trans 42: 1623-1628]. However, several additional angiogenic factors such as platelet derived growth factor (PDGF), hepatocyte growth factor (HGF), epidermal growth factor (EGF) and basic fibroblast growth factor (bFGF) have also been reported to play possible roles in AMD [see Frank R N, Amin R H, Eliott D, Puklin J E, Abrams G W (1996) Basic fibroblast growth factor and vascular endothelial growth factor are present in epiretinal and choroidal neovascular membranes. Am J Ophthalmol 122: 393-403, de OD, Jr., Rodrigues E B, Maia M, Magalhaes O, Jr., Penha F M, Farah M E (2011) Cytokines in neovascular age-related macular degeneration: fundamentals of targeted combination therapy. Br J Ophthalmol 95: 1631-1637, Lu Q, Zhang L, Shen X, Zhu Y, Zhang Q, Zhou, Q, et al (2012) A novel and effective human hepatocyte growth factor kringle 1 domain inhibits ocular neovascularization. Exp Eye Res 105: 15-20, Campochiaro P A (2013) Ocular neovascularization. J Mol Med (Berl) 91: 311-321, and Jonas J B, Tao Y, Neumaier M, Findeisen P (2012) Cytokine concentration in aqueous humour of eyes with exudative age-related macular degeneration. Acta Ophthalmol 90: e381-e388]. Interestingly, signal transduction by these factors was also found to be affected by neuropilins, either because neuropilins serve as binding receptors to these factors or because their receptors form complexes with neuropilins [see Pellet-Many C, Frankel P, Evans I M, Herzog B, Junemann-Ramirez M, Zachary, I. C (2011) Neuropilin-1 mediates PDGF stimulation of vascular smooth muscle cell migration and signalling via p130Cas. Biochem J 435: 609-618, Sulpice E, Plouet J, Berge M, Allanic D, Tobelem G, Merkulova-Rainon, T (2007) Neuropilin-1 and neuropilin-2 act as coreceptors, potentiating proangiogenic activity. Blood 111: 2036-2045, West D C, Chris R G, Duchesne L, Patey S J, Terry C J, Turnbull J E, et al (2005) Interactions of multiple heparin-binding growth factors with neuropilin-1 and potentiation of the activity of fibroblast growth factor-2. J Biol Chem 280: 13457-13464 and Rizzolio S, Rabinoviz N, Rainero E, Lanzetti L, Serini G, Norman J C, et al (2012) Neuropilin-1 dependent regulation of EGF-Receptor signaling. Cancer Res 72: 5801-5811]. Activation of plexins by class-3 semaphorins also activates inhibitory signalling cascades that can inhibit signal transduction induced by angiogenic factors even when the semaphorins do not compete with these factors for binding to neuropilins [see Guttmann-Raviv N, Shraga-Heled N, Varshaysky A, Guimaraes-Sternberg C, Kessler O, Neufeld, G (2007) Semaphorin-3A and Semaphorin-3F Work Together to Repel Endothelial Cells and to Inhibit Their Survival by Induction of Apoptosis. J Biol Chem 282: 26294-26305]. Since these angiogenic factors all activate the ras signalling cascade, it was determined whether FR-sema3C can inhibit in cultured human umbilical vein derived endothelial cells (HUVEC) ERK1/2 phosphorylation induced by these factors as a proof of concept in order to determine if FR-sema3C has the potential to inhibit their activity in AMD. To this end, purified FR-sema3C that was epitope tagged at the C-terminal with an Fc tag (FR-sema3C/Fc) was used, as previously described [see Mumblat Y, Kessler O, Ilan N, Neufeld G (2015) Full length semaphorin-3C functions as an inhibitor of tumor lymphangiogenesis and tumor metastasis. Cancer Res 75: 2177-2186]. FR-sema3C/Fc inhibited VEGF-induced signal transduction as manifested by its ability to inhibit VEGF-induced phosphorylation of ERK1/2 (FIG. 14A), P38 Map Kinase, AKT and FAK[125] (FIGS. 18A-C). FR-sema3C also inhibited PDGF-BB-induced activation of ERK1/2 in endothelial cells (FIG. 14B) and also partially inhibited bFGF-induced activation of ERK1/2 in three independent experiments although the inhibition did not reach statistical significance (FIG. 14C). However, FR-sema3C failed to inhibit ERK1/2 phosphorylation induced by hepatocyte growth factor (HGF) and epidermal growth factor (EGF) although HGF is known to transduce signals using the sema3C receptor neuropilin-1 (FIGS. 14D and 14E) [Sulpice E, Plouet J, Berge M, Allanic D, Tobelem G, Merkulova-Rainon, T (2007) Neuropilin-1 and neuropilin-2 act as coreceptors, potentiating proangiogenic activity. Blood 111: 2036-2045]. These observations suggest that FR-Sema3C may have a wider range of anti-angiogenic activity compared to currently used drugs, such as bevacizumab or ranibizumab, which selectively target VEGF. However, aflibercept was also able to inhibit PDGF-BB-induced phosphorylation of ERK1/2 but not bFGF-induced phosphorylation of ERK1/2 (FIGS. 18D and 18E).

FR-sema3C Inhibits Laser-Induced CNV as Efficiently as Aflibercept

Figure 15A:
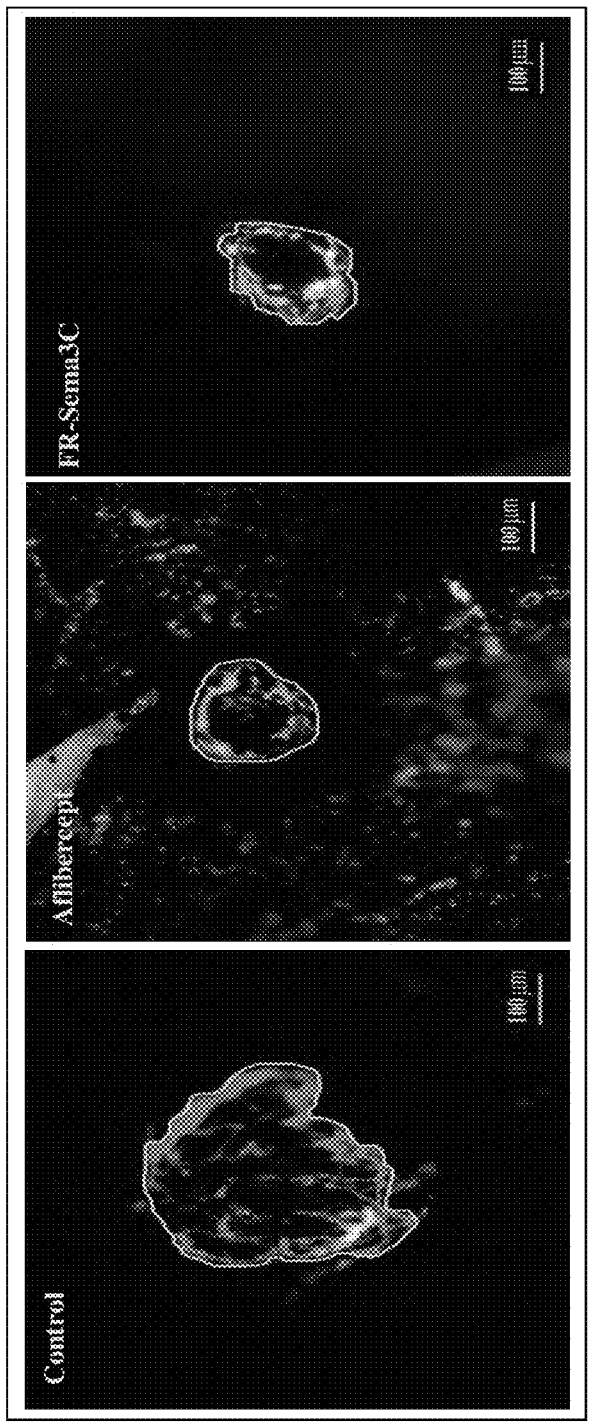
Figure 15C:
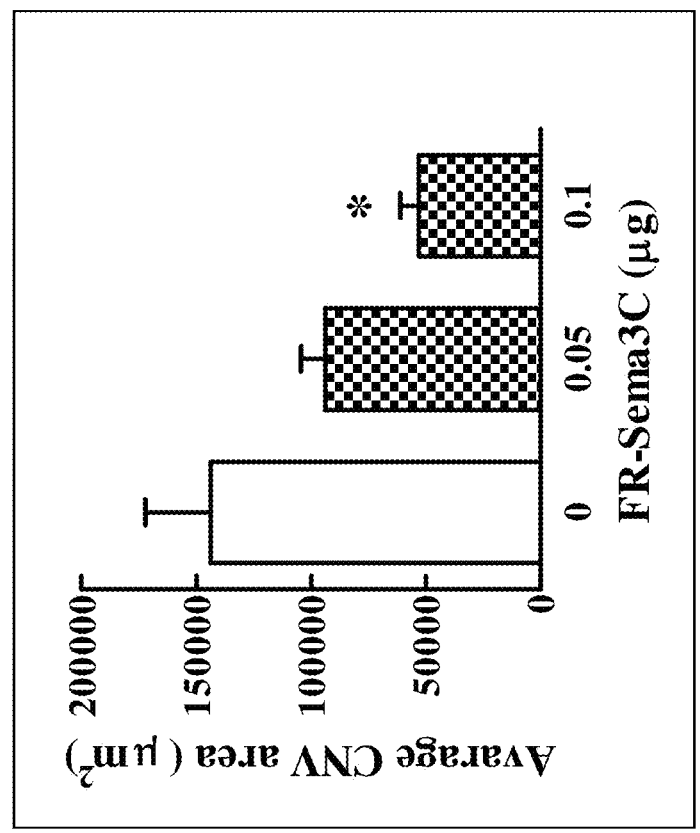
Figure 15B:
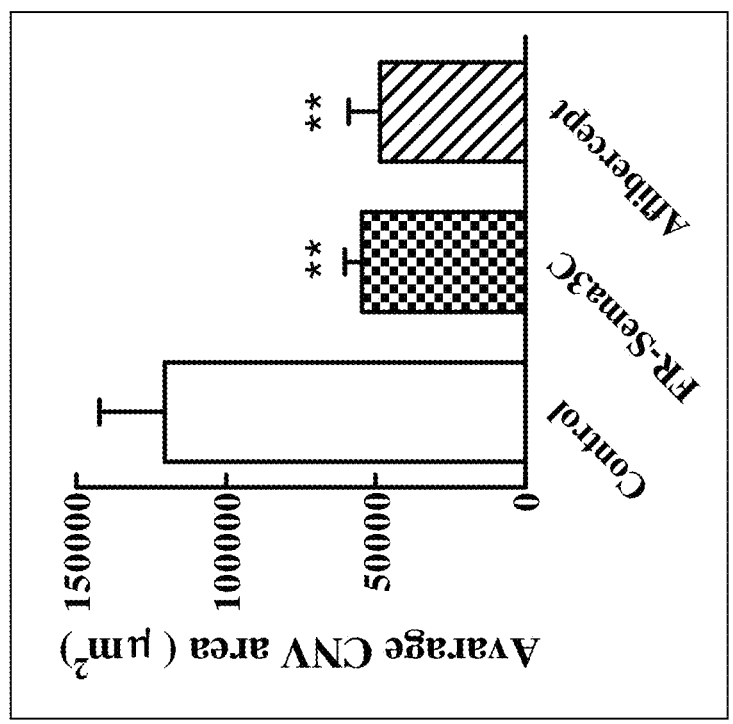

In order to find out if FR-Sema3C does indeed possess potential as a possible candidate drug for the treatment of exudative AMD, it was determined whether injection of FR-Sema3C/Fc into the vitreal chamber of C57 black mouse eyes can inhibit CNV induced by laser photocoagulation [see Pennesi M E, Neuringer M, Courtney R J (2012) Animal models of age related macular degeneration. Mol Aspects Med 33: 487-509]. A single bolus intravitreal injection of 100 ng FR-Sema3C/Fc [Mumblat Y, Kessler O, Ilan N, Neufeld G (2015) Full length semaphorin-3C functions as an inhibitor of tumor lymphangiogenesis and tumor metastasis. Cancer Res 75: 2177-2186] was performed immediately after laser photocoagulation. FR-sema3C inhibited CNV significantly as determined by the comparison of the mean areas of invading blood vessels per laser burn in individual vehicle treated mice (120604+/−21727 $\mu m^2$), with the mean areas of invading blood vessels per laser burn in individual FR-Sema3C/Fc treated mice (54518+/−5858 $\mu m^2$) ($p<0.01$) a week after induction of CNV (FIGS. 15A and 15B). The inhibition produced by FR-sema3C/Fc was comparable to the inhibition produced by a single bolus injection of 5 µg aflibercept [see Balaratnasingam C, Dhrami-Gavazi E, McCann J T, Ghadiali Q, Feund K B (2015) Aflibercept: a review of its use in the treatment of choroidal neovascularization due to age-related macular degeneration. Clin Ophthalmol 9: 2355-2371], which is probably the most effective drug currently used to treat exudative AMD (FIGS. 15A and 15B). Mice were also treated with lower concentrations of FR-sema3C, but although 50 ng of FR-sema3C consistently inhibited CNV, the inhibition failed to reach statistical significance (FIG. 15C). The effects of FR-sema3C/Fc on laser photocoagulation-induced CNV in the mouse model were also compared with those of sema3C/Fc. Both FR-sema3C/Fc and the commercial sema3C/Fc had a similar molecular mass of about 130 kDa, and there were no visible proteolytic fragments (FIG. 19A). Both FR-sema3C and sema3C inhibited CNV similarly and although sema3C seemed a bit less active, the difference was not statistically significant (FIG. 19B). It was also determined whether purified p65-Sema3C/myc FIG. 19A) [see Mumblat Y, Kessler O, Ilan N, Neufeld G (2015) Full length semaphorin-3C functions as an inhibitor of tumor lymphangiogenesis and tumor metastasis. Cancer Res 75: 2177-2186] affects laser photocoagulation-induced CNV. However, as expected, p65-Sema3C did not inhibit laser photocoagulation-induced CNV (FIG. 19C).

FR-sema3C does not Impair the Function of the Retina

Figure 16C:
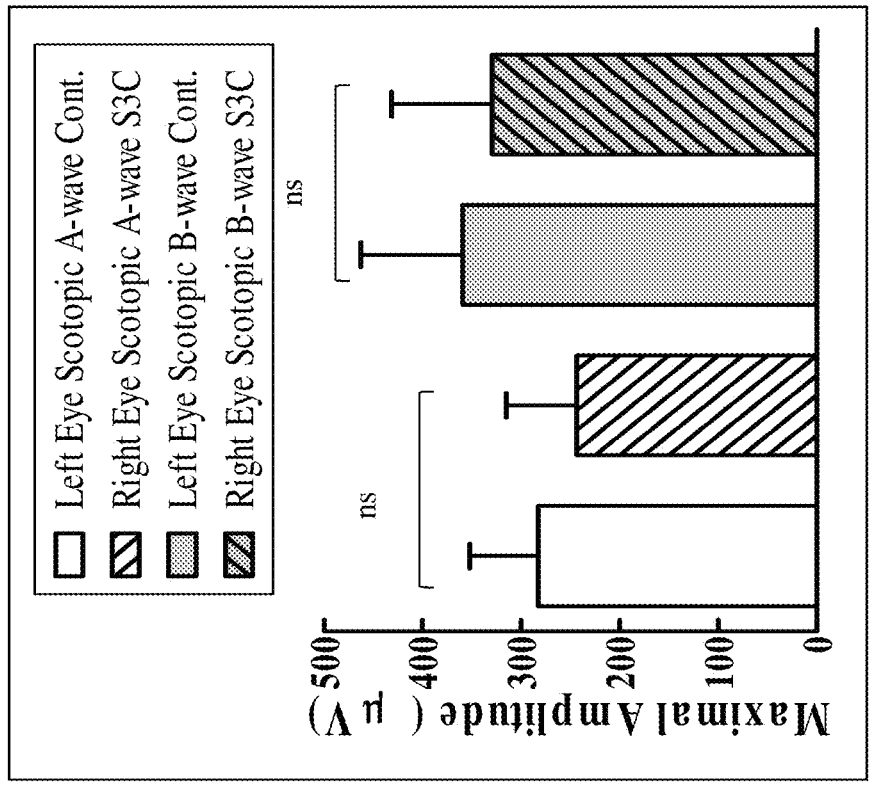
Figure 16A:
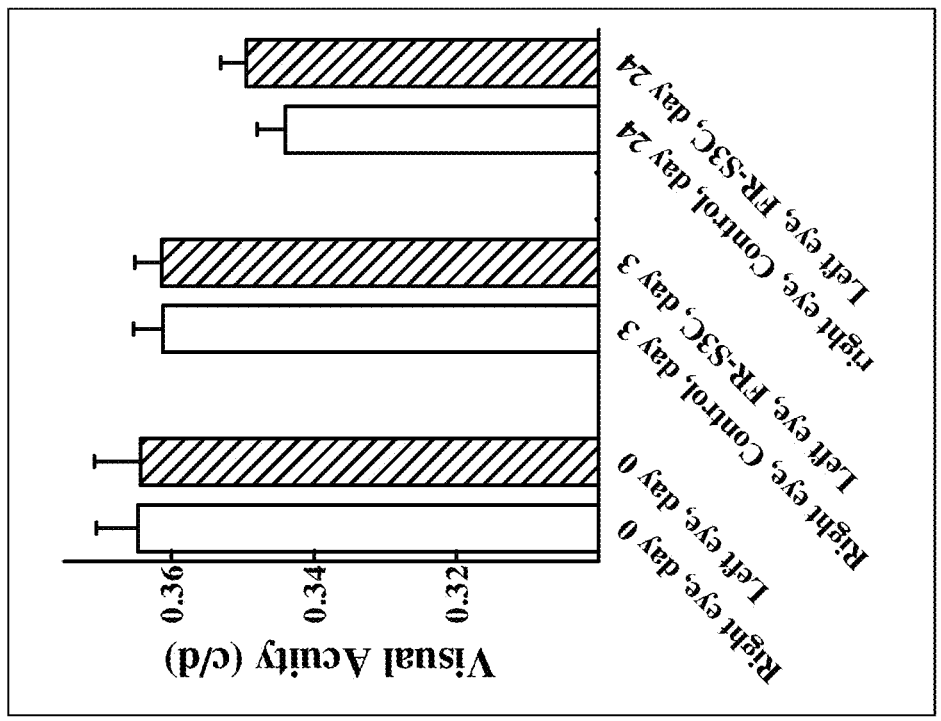

In order to determine if FR-sema3C/Fc has any detrimental effects on vision by itself, a single bolus of 100 ng FR-sema3C/Fc was injected into the vitreous of left eyes of mice and a similar volume of vehicle into their right eyes. The effects of the injections on visual acuity were determined prior to the injections as well as three days and twenty four days after injection using the OKR test [see Prusky G T, Alam N M, Beekman S, Douglas R M (2004) Rapid quantification of adult and developing mouse spatial vision using a virtual optomotor system. Invest Ophthalmol Vis Sci 45: 4611-4616]. After three days there was no difference between control eyes and eyes injected with FR-sema3C/Fc nor was there loss of visual acuity as compared with the measurements done in both groups of mice prior to injection (FIG. 16A). After 24 days there was still no difference in visual acuity between control eyes and eyes injected with FR-sema3C/Fc although there was some minor deterioration of visual acuity in both control and FR-sema3C/Fc treated eyes which was probably due to non-specific effects of the injection procedure (FIG. 16A). These results suggest that FR-sema3C/Fc does not hamper visual acuity on its own (FIG. 16A).

Figure 16B:
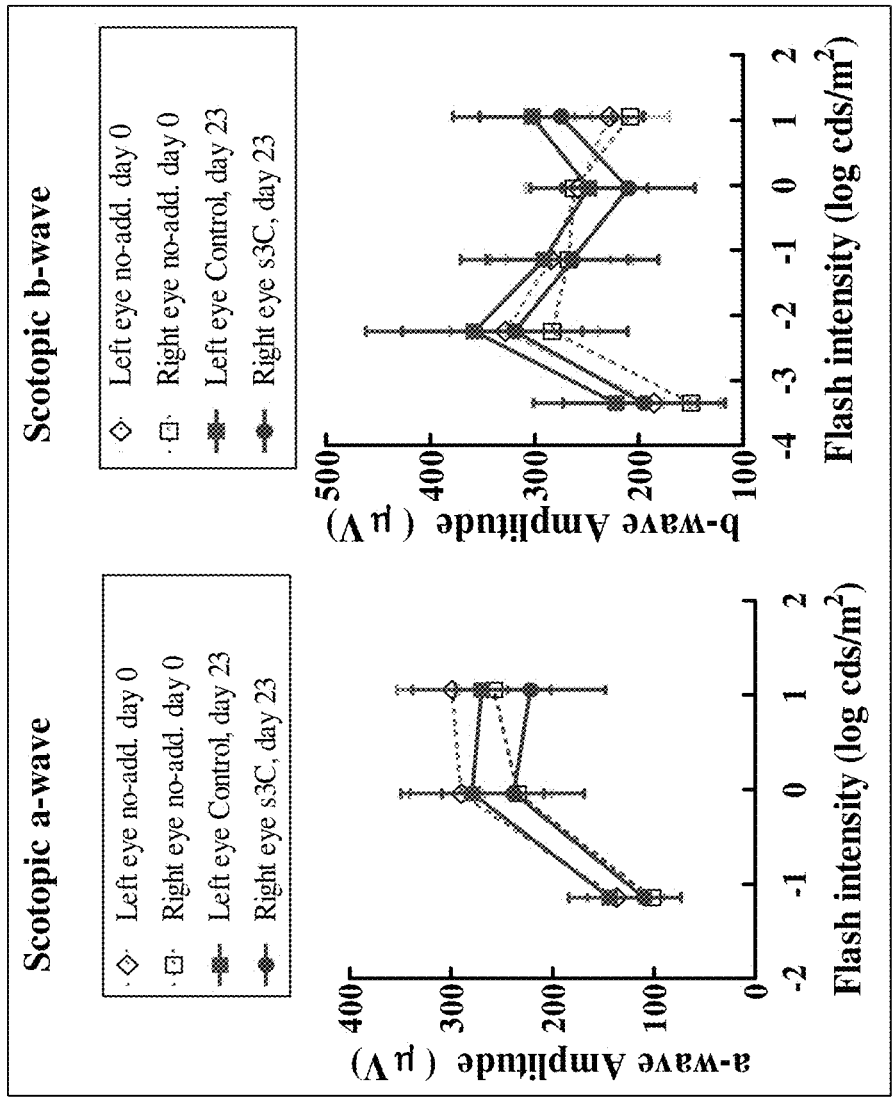
Figure 16D:
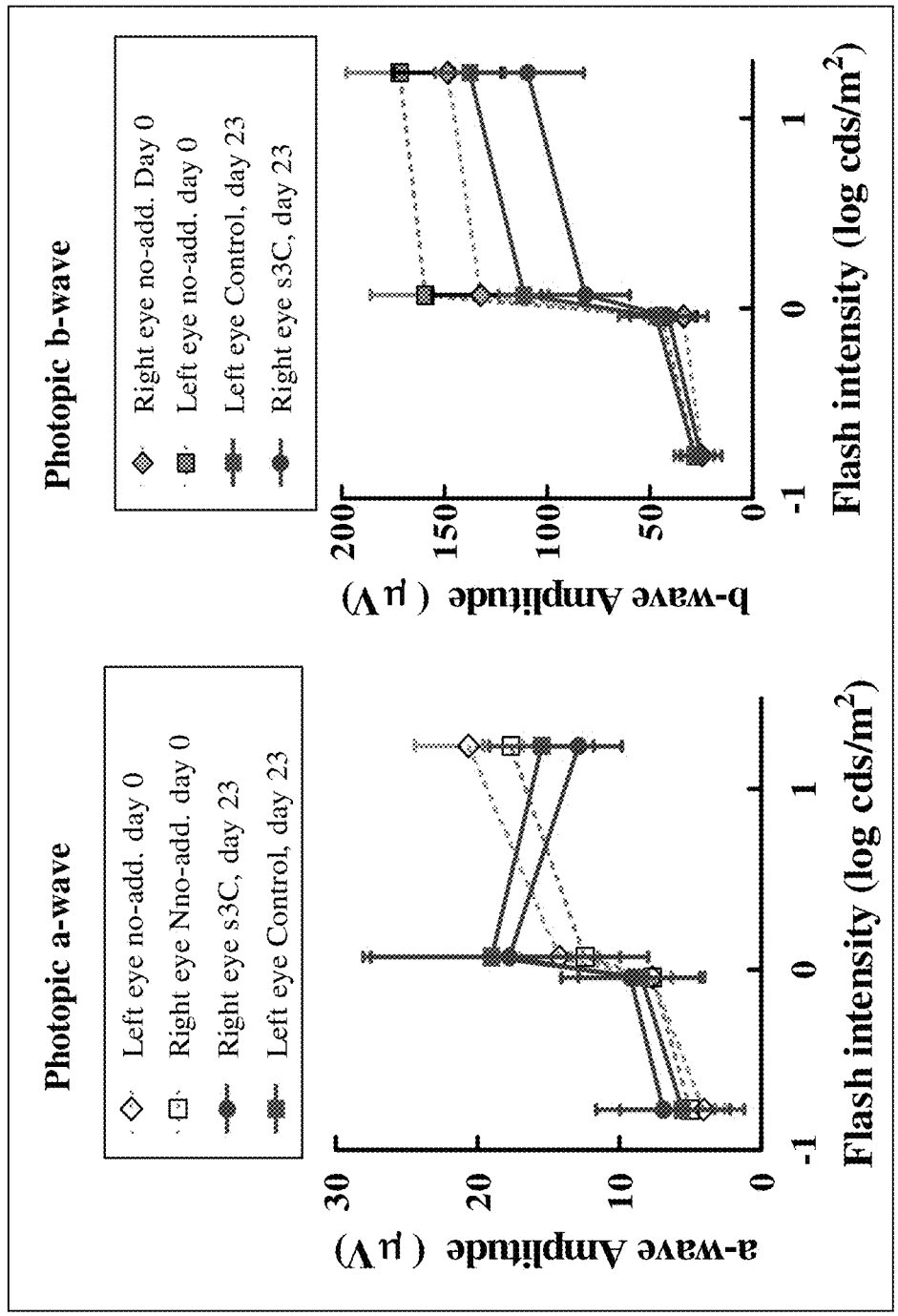
Figure 16E:
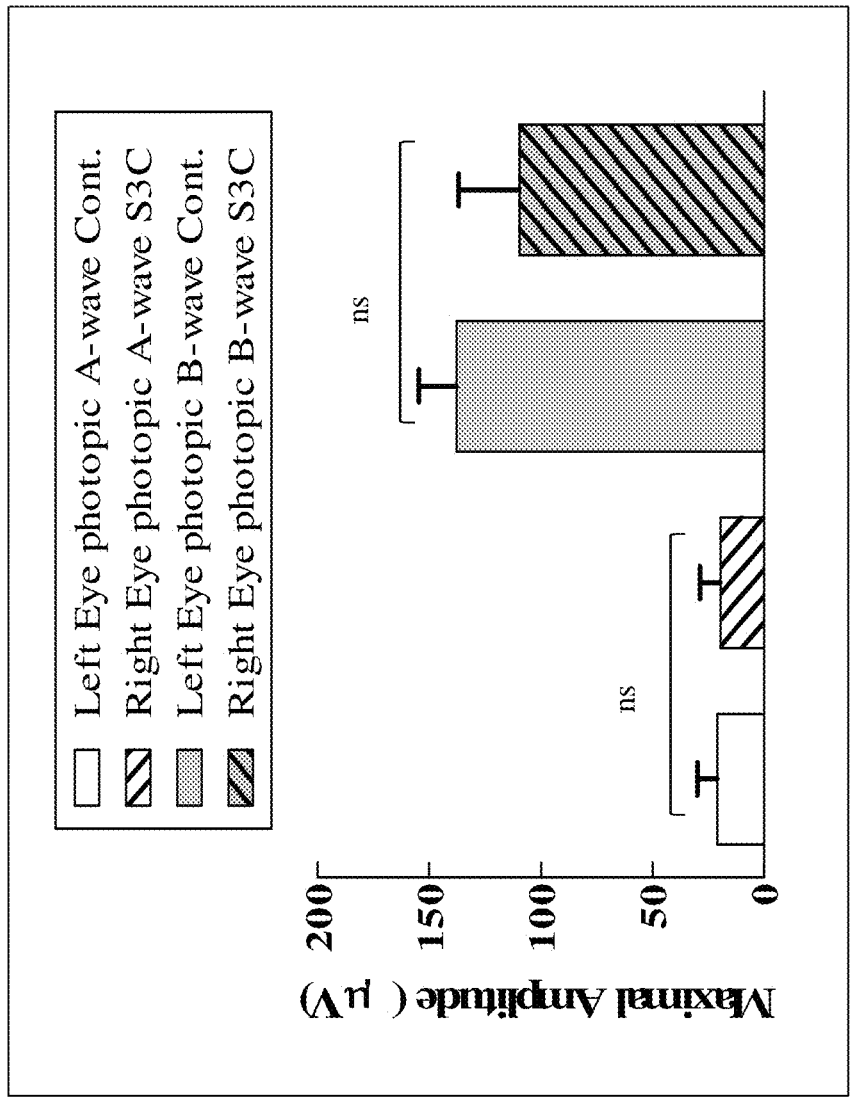

In order to determine if FR-sema3C/Fc exerts detrimental effects on the response of the retina to light stimuli, ERG tests were performed before injection and 23 days after injection of a single 100 ng bolus of FR-sema3C/Fc into the vitreous of the right eyes of healthy mice and compared the responses with the responses of the left eyes which were injected with an equal volume of vehicle (FIGS. 16B and 16D). In this test too, a significant difference between scotopic and photopic ERG responses of eyes that received vehicle alone or FR-sema3C/Fc after 23 days were not observed (FIGS. 16B and 16D). There was also no statistically significant difference between the average maximal EGR response amplitudes of scotopic and photopic a and b-waves of eyes treated with FR-sema3C/Fc and the average maximal EGR response amplitudes of scotopic and photopic a and b-waves of eyes treated with vehicle alone after 23 days (FIGS. 16C and 16E).

Figure 17A:
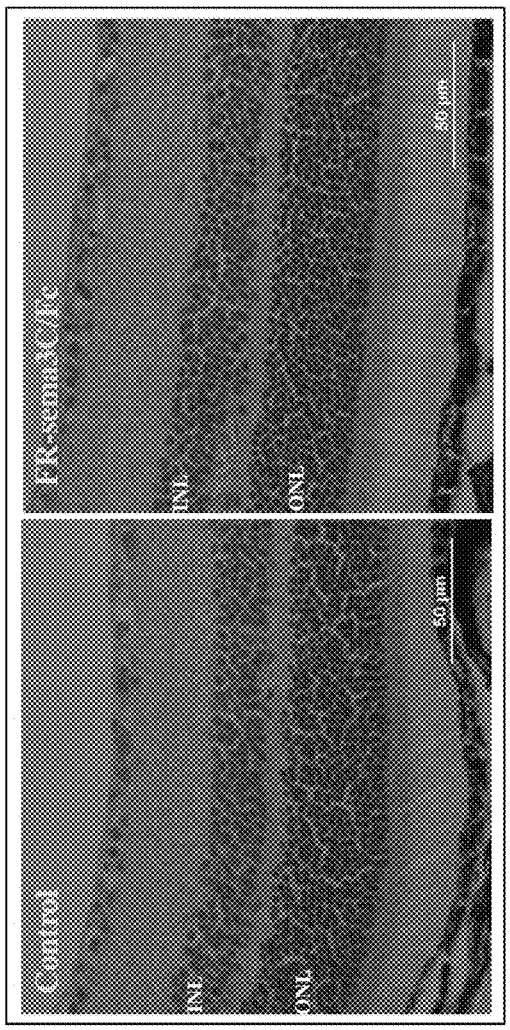
Figure 17B:
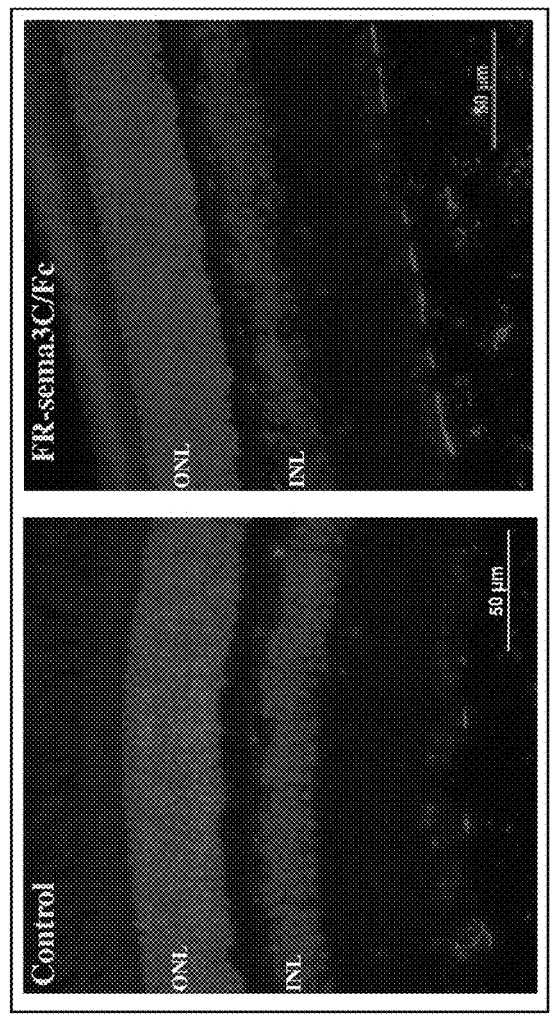

Haematoxylin-eosin stained histological sections of retinas derived from six vehicle and six FR-sema3C/Fc treated eyes after 23 days were also compared. However, in none of the FR-sema3C/Fc treated retinas could any significant differences be detected when compared to retinas injected with vehicle alone (FIG. 17A). The expression pattern of GFAP in vehicle and FR-sema3C/Fc treated retinas after 23 days were also compared. Following retinal insults causing functional and structural damage, GFAP is frequently expressed in retinal Müller cells [54,55]. However, no GFAP expression in retinal Müller cells in any of the six FR-sema3C/Fc treated retinas or in any of the vehicle injected eyes were detected, indicating that FR-sema3C/Fc injection is not harmful to the retina (FIG. 17B).

Figure 17C:
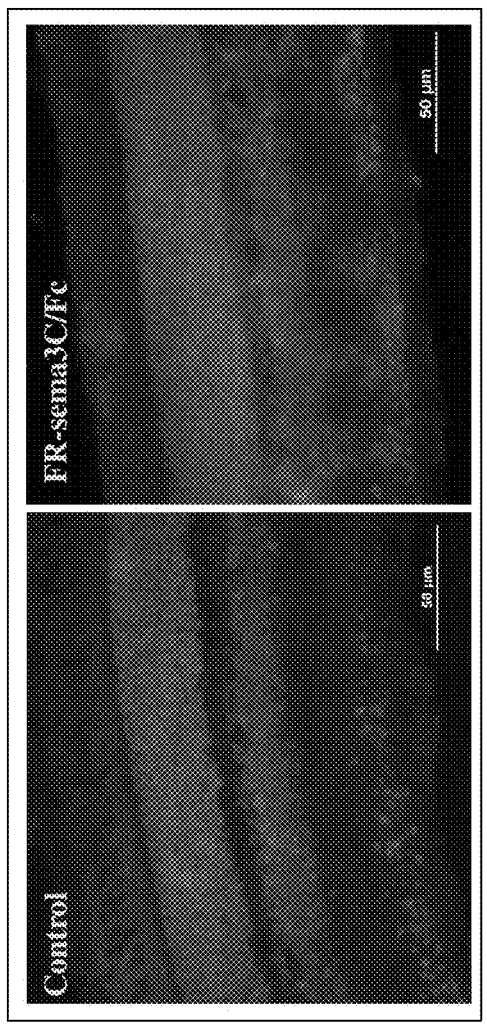
Figure 17D:
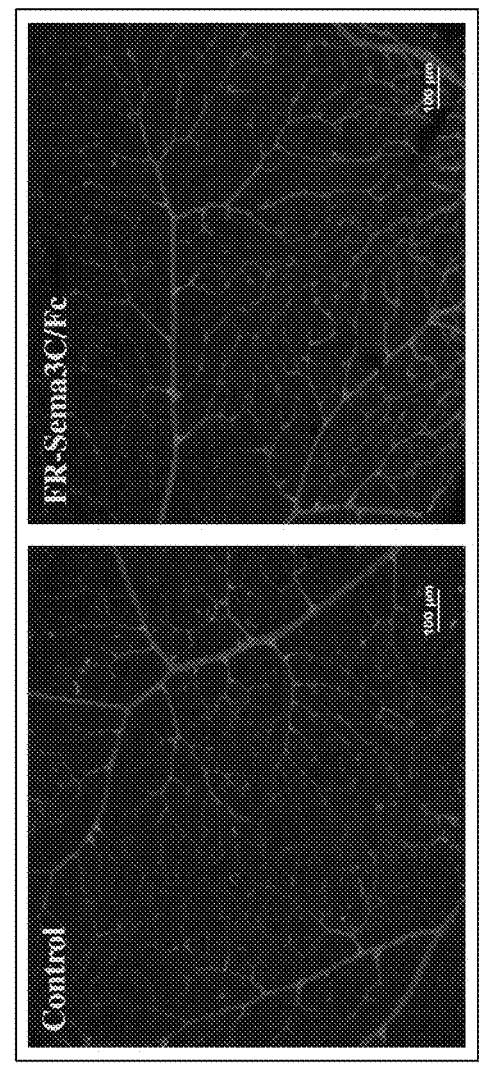

PKC immunoreactivity is used to identify rod bipolar cells in the vertebrate retina [see Casini G, Grassi A, Trasarti L, Bagnoli P (1996) Developmental expression of protein kinase C immunoreactivity in rod bipolar cells of the rabbit retina. Vis Neurosci 13: 817-831]. Retinal staining for PKC immunoreactivity of retinas from eyes treated with FR-sema3C/Fc 23 days post injection did not reveal any differences between FR-sema3C treated and control eyes (FIG. 17C). Furthermore, there was no discernible difference between the morphology of retinal blood vessels of eyes injected with FR-sema3C and eyes that were treated with vehicle only (FIG. 17D). Likewise, injection of wild type sema3C also had no effect on the morphology of mature retinal blood vessels (FIG. 20B) as previously reported [see Yang W J, Hu J, Uemura A, Tetzlaff F, Augustin H G, Fischer A (2015) Semaphorin-3C signals through Neuropilin-1 and PlexinD1 receptors to inhibit pathological angiogenesis. EMBO Mol Med 20, 1267-1284]. Injection of FR-sema3C also failed to induce apoptosis in the retina as determined using the TUNEL assay (FIG. 20A) nor did the treatment affect the integrity of the retinal pigment epithelial cells layer (FIG. 20C).

Sequence table

| SEQ ID # | Sequence Identity | Sequence |
|---|---|---|
| SEQ ID NO: 1 | Human wild-type Semaphorin 3C | MAFRTICVLVGVFICSICVKGSSQPQARVYLT FDELRETKTSEYFSLSHHPLDYRILLMDEDQD RIYVGSKDHILSLNINNISQEALSVFWPASTI KVEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKWT TFLKARLVCSVTDEDGPETHFDELEDVFLLE TDNPRTTLVYGIFTTSSSVFKGSAVCVYHLSD IQTVFNGPFAHKEGPNHQLISYQGRIPYPRPG TCPGGAFTPNMRTTKEFPDDVVTFIRNHPLM YNSIYPIHKRPLIVRIGTDYKYTKIAVDRVNA ADGRYHVLFLGTDRGTVQKVVVLPTNNSVS GELILEELEVFKNHAPITTMKISSKKQQLYVS SNEGVSQVSLHRCHIYGTACADCCLARDPYC AWDGHSCSRFYPTGKRRSRRQDVRHGNPLT QCRGFNLKAYRNAAEIVQYGVKNNTTFLEC APKSPQASIKWLLQKDKDRRKEVKLNERIIA TSQGLLIRSVQGSDQGLYHCIATENSFKQTIA KINFKVLDSEMVAVVTDKWSPWTWASSVR ALPFHPKDIMGAFSHSEMQMINQYCKDTRQ QHQQGDESQKMRGDYGKLKALINSRKSRNR RNQLPES |
| SEQ ID NO: 2 | Furin-like pro-protein convertase cleavage site 1. Amino acids 144-147 of SEQ ID NO: 1. | RGRR |
| SEQ ID NO: 3 | Furin-like pro-protein convertase cleavage site 2. Amino acids 549-552 of SEQ ID NO: 1. | RSRR |
| SEQ ID NO: 4 | Furin-like pro-protein convertase cleavage site 3. Amino acids 742-745 of SEQ ID NO: 1. | RNRR |
| SEQ ID NO: 5 | The basic domain of Sema 3C. Amino acids 724-745 of SEQ ID NO: 1. | KMRGDYGKLKALINSRKSRNRR |
| SEQ ID NO: 6 | Sema 3C cleaved at site 2 (Sema 3C-p65) | MAFRTICVLVGVFICSICVKGSSQPQARVYLT FDELRETKTSEYFSLSHHPLDYRILLMDEDQD RIYVGSKDHILSLNINNISQEALSVFWPASTI KVEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKWT TFLKARLVCSVTDEDGPETHFDELEDVFLLE TDNPRTTLVYGIFTTSSSVFKGSAVCVYHLSD IQTVFNGPFAHKEGPNHQLISYQGRIPYPRPG TCPGGAFTPNMRTTKEFPDDVVTFIRNHPLM YNSIYPIHKRPLIVRIGTDYKYTKIAVDRVNA ADGRYHVLFLGTDRGTVQKVVVLPTNNSVS GELILEELEVFKNHAPITTMKISSKKQQLYVS SNEGVSQVSLHRCHIYGTACADCCLARDPYC AWDGHSCSRFYPTGKR |
| SEQ ID NO: 7 | FC-tagged Sema 3C cleaved at site 2 (Sema 3C-p65-FC) | MAFRTICVLVGVFICSICVKGSSQPQARVYLT FDELRETKTSEYFSLSHHPLDYRILLMDEDQD RIYVGSKDHILSLNINNISQEALSVFWPASTI KVEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKWT TFLKARLVCSVTDEDGPETHFDELEDVFLLE TDNPRTTLVYGIFTTSSSVFKGSAVCVYHLSD IQTVFNGPFAHKEGPNHQLISYQGRIPYPRPG TCPGGAFTPNMRTTKEFPDDVVTFIRNHPLM YNSIYPIHKRPLIVRIGTDYKYTKIAVDRVNA ADGRYHVLFLGTDRGTVQKVVVLPTNNSVS GELILEELEVFKNHAPITTMKISSKKQQLYVS SNEGVSQVSLHRCHIYGTACADCCLARDPYC AWDGHSCSRFYPTGKRLEDKTHTCPPCPAPE LLGGPSVFLFPPKPKDTLMISRTPEVTCVVVD VSHEDPEVKFNWYVDGVEVHNAKTKPREEQ YNSTYRVVSVLTVLHQDWLNGKEYKCKVS NKALPAPIEKTISKAKGQPREPQVYTLPPSRE EMTKNQVSLTCLVKGFYPSDIAVEWESNGQP ENNYKTTPPVLDSDGSFFLYSKLTVDKSRWQ QGNVFSCSVMHEALHNHYTQKSLSLSPGK |
| SEQ ID NO: 8 | UNCL-Sema3C-Fc (as described in Example 1) | MAFRTICVLVGVFICSICVKGSSQPQARVYLT FDELRETKTSEYFSLSHHPLDYRILLMDEDQD RIYVGSKDHILSLNINNISQEALSVFWPASTI KVEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS |

| SEQ ID # | Sequence Identity | Sequence |
|---|---|---|
| | | EPMFVDAHVIPDGTDPNDAKVYFFFKEKLTD NNRSTKQIHSMIARICPNDTGGLRSLVNKW TTFLKARLVCSVTDEDGPETHFDELEDVFLL ETDNPRTTLVYGIFTTSSSVFKGSAVCVYHLS DIQTVFNGPPFAHKEGPNHQLISYQGRIPYPRP GTCPGGAFTPNMRTTKEFPDDVVTFIRNHPL MYNSIYPIHKRPLIVRIGTDYKYTKIAVDRVN AADGRYHVLFLGTDRGTVQKVVVLPTNNSV SGELILEELEVFKNHAPITTMKISSKKQQLYV SSNEGVSQVSLHRCHIYGTACADCCLARDPY CAWDGHSCSRFYPTGKRKSKKQDVRHGNP LTQCRGFNLKAYRNAAEIVQYGVKNNTTFL ECAPKSPQASIKWLLQKDKDRRKEVKLNERI IATSQGLLIRSVQGSDQGLYHCIATENSFKQT IAKINFKVLDSEMVAVVTDKWSPWTWASSV RALPFHPKDIMGAFSHSEMQMINQYCKDTR QQHQQGDESQKMRGDYGKLKALINSLEDKT HTCPPCPAPELLGGPSVFLFPPKPKDTLMISR TPEVTCVVVDVSHEDPEVKFNWYVDGVEVH NAKTKPREEQYNSTYRVVSVLTVLHQDWLN GKEYKCKVSNKALPAPIEKTISKAKGQPREP QVYTLPPSREEMTKNQVSLTCLVKGFYPSDI AVEWESNGQPENNYKTTPPVLDSDGSFFLYS KLTVDKSRWQQG NVFSCSVMHEALHNHYTQKSLSLSPGK |
| SEQ ID NO: 9 | UNCL-Sema3C-myc-6His (as described in Example 1) | MAFRTICVLVGVFICSICVKGSSQPQARVYLT FDELRETKTSEYFSLSHHPLDYRILLMDEDQD RIYVGSKDHILSLNINNISQEALSVFWPASTI KVEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKW TTFLKARLVCSVTDEDGPETHFDELEDVFLL ETDNPRTTLVYGIFTTSSSVFKGSAVCVYHLS DIQTVFNGPPFAHKEGPNHQLISYQGRIPYPRP GTCPGGAFTPNMRTTKEFPDDVVTFIRNHPL MYNSIYPIHKRPLIVRIGTDYKYTKIAVDRVN AADGRYHVLFLGTDRGTVQKVVVLPTNNSV SGELILEELEVFKNHAPITTMKISSKKQQLYV SSNEGVSQVSLHRCHIYGTACADCCLARDPY CAWDGHSCSRFYPTGKRKSKKQDVRHGNPL TQCRGFNLKAYRNAAEIVQYGVKNNTTFLE CAPKSPQASIKWLLQKDKDRRKEVKLNERII ATSQGLLIRSVQGSDQGLYHCIATENSFKQTI AKINFKVLDSEMVAVVTDKWSPWTWASSV RALPFHPKDIMGAFSHSEMQMINQYCKDTR QQHQQGDESQKMRGDYGKLKALINSLESRG PFEQKLISEEDLNMHTGHHHHHH |
| SEQ ID NO: 10 | Sema3C having cleavage site 2 modified to KSKK, preventing it from being cleaved at site 2 (As described in Example 1). | MAFRTICVLVGVFICSICVKGSSQPQARVYLT FDELRETKTSEYFSLSHHPLDYRILLMDEDQD RIYVGSKDHILSLNINNISQEALSVFWPASTI KVEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKWT TFLKARLVCSVTDEDGPETHFDELEDVFLLE TDNPRTTLVYGIFTTSSSVFKGSAVCVYHLSD IQTVFNGPFAHKEGPNHQLISYQGRIPYPRPG TCPGGAFTPNMRTTKEFPDDVVTFIRNHPLM YNSIYPIHKRPLIVRIGTDYKYTKIAVDRVNA ADGRYHVLFLGTDRGTVQKVVVLPTNNSVS GELILEELEVFKNHAPITTMKISSKKQQLYVS SNEGVSQVSLHRCHIYGTACADCCLARDPYC AWDGHSCSRFYPTGKRKSKKQDVRHGNPLT QCRGFNLKAYRNAAEIVQYGVKNNTTFLEC APKSPQASIKWLLQKDKDRRKEVKLNERIIA TSQGLLIRSVQGSDQGLYHCIATENSFKQTIA KINFKVLDSEMVAVVTDKWSPWTWASSVR ALPFHPKDIMGAFSHSEMQMINQYCKDTRQ QHQQGDESQKMRGDYGKLKALINSRKSRNR RNQLPES |
| SEQ ID NO: 11 | Site 2 after step 1 of mutagenesis, as described in Example 1 | RSKR |
| SEQ ID NO: 12 | Site 2 after steps 1 + 2 of mutagenesis, as described in Example 1 | KSKR |
| SEQ ID NO: 13 | Mutated uncleavable site 2 after steps 1-3 of mutagenesis, as described in Example 1 | KSKK |
| SEQ ID NO: 14 | FC-tagged Human wild-type Semaphorin 3C | MAFRTICVLVGVFICSICVKGSSQPQARVYLT FDELRETKTSEYFSLSHHPLDYRILLMDEDQD RIYVGSKDHILSLNINNISQEALSVFWPASTI KVEECKMAGKDPTHGCGNFVRVIQTFNRTHL YVCGSGAFSPVCTYLNRGRRSEDQVFMIDSK CESGKGRCSFNPNVNTVSVMINEELFSGMYI DFMGTDAAIFRSLTKRNAVRTDQHNSKWLS EPMFVDAHVIPDGTDPNDAKVYFFFKEKLTD NNRSTKQIHSMIARICPNDTGGLRSLVNKWT TFLKARLVCSVTDEDGPETHFDELEDVFLLE TDNPRTTLVYGIFTTSSSVFKGSAVCVYHLSD IQTVFNGPFAHKEGPNHQLISYQGRIPYPRPG TCPGGAFTPNMRTTKEFPDDVVTFIRNHPLM YNSIYPIHKRPLIVRIGTDYKYTKIAVDRVNA ADGRYHVLFLGTDRGTVQKVVVLPTNNSVS GELILEELEVFKNHAPITTMKISSKKQQLYVS SNEGVSQVSLHRCHIYGTACADCCLARDPYC AWDGHSCSRFYPTGKRRSRRQDVRHGNPLT QCRGFNLKAYRNAAEIVQYGVKNNTTFLEC APKSPQASIKWLLQKDKDRRKEVKLNERIIA TSQGLLIRSVQGSDQGLYHCIATENSFKQTIA KINFKVLDSEMVAVVTDKWSPWTWASSVR ALPFHPKDIMGAFSHSEMQMINQYCKDTRQ QHQQGDESQKMRGDYGKLKALINSRKSRNR RNQLPESLEDKTHTCPPCPAPELLGGPSVFLF PPKPKDTLMISRTPEVTCVVVDVSHEDPEVK FNWYVDGVEVHNAKTKPREEQYNSTYRVVS VLTVLHQDWLNGKEYKCKVSNKALPAPIEK TISKAKGQPREPQVYTLPPSREEMTKNQVSL TCLVKGFYPSDIAVEWESNGQPENNYKTTPP VLDSDGSFFLYSKLTVDKSRWQQGNVFSCSV MHEALHNHYTQKSLSLSPGK |
| SEQ ID NO: 15 | cDNA corresponding to human wild-type | ATGGCATTCCGGACAATTTGCGTTGGTT GGAGTATTTATTTGTTCTATCTGTGTGAAA GGATCTTCCCAGCCCCAAGCAAGAGTTTAT TTAACATTTGATGAACTTCGAGAAACCAAG |

Sequence table

| SEQ ID # | Sequence Identity | Sequence |
|---|---|---|
| | Semaphorin 3C (SEQ ID NO: 1) | ACCTCTGAATACTTCAGCCTTTCCCACCAT CCTTTAGACTACAGGATTTTATTAATGGAT GAAGATCAGGACCGGATATATGTGGGAAG CAAAGATCACATTCTTTCCCTGAATATTAA CAATATAAGTCAAGAAGCTTTGAGTGTTTT CTGGCCAGCATCTACAATCAAAGTTGAAG AATGCAAAATGGCTGGCAAAGATCCCACA CACGGCTGTGGGAACTTTGTCCGTGTAATT CAGACTTTCAATCGCACACATTTGTATGTC TGTGGGAGTGGCGCTTTCAGTCCTGTCTGT ACTTACTTGAACAGAGGGAGGAGATCAGA GGACCAAGTTTTCATGATTGACTCCAAGTG TGAATCTGGAAAAGGACGCTGCTCTTTCAA CCCCAACGTGAACACGGTGTCTGTTATGAT CAATGAGGAGCTTTTCTCTGGAATGTATAT AGATTTCATGGGACAGATGCTGCTATTTT TCGAAGTTTAACCAAGAGGAATGCGGTCA GAACTGATCAACATAATTCCAAATGGCTAA GTGAACCTATGTTTGTAGATGCACATGTCA TCCCAGATGGTACTGATCCAAATGATGCTA AGGTGTACTTCTTCTTCAAAGAAAAACTGA CTGACAATAACAGGAGCACGAAACAGATT CATTCCATGATTGCTGAAATATGTCCTAAT GACACTGGTGGACTGCGTAGCCTTGTCAAC AAGTGGACCACTTTCTTAAAGGCGAGGCTG GTGTGCTCGGTAACAGATGAAGACGGCCC AGAAACACACTTTGATGAATTAGAGGATG TGTTTCTGCTGGAAACTGATAACCCGAGGA CAACACTAGTGTATGGCATTTTTACAACAT CAAGCTCAGTTTTCAAAGGATCAGCCGTGT GTGTGTATCATTTATCTGATATACAGACTG TGTTTAATGGGCCTTTTGCCCACAAAGAAG GGCCCAATCATCAGCTGATTTCCTATCAGG GCAGAATTCCATATCCTCGCCCTGGAACTT GTCCAGGAGGAGCATTTACACCCAATATGC GAACCACCAAGGAGTTCCCAGATGATGTT GTCACTTTTATTCGGAACCATCCTCTCATGT ACAATTCCATCTACCCAATCCACAAAAGGC CTTTGATTGTTCGTATTGGCACTGACTACA AGTATACAAAGATAGCTGTGGATCGAGTG AACGCTGCTGATGGGAGATACCATGTCCTG TTTCTCGGAACAGATCGGGGTACTGTGCAA AAAGTGGTTGTTCTTCCTACTAACAACTCT GTCAGTGGCGAGCTCATTCTGGAGGAGCTG GAAGTCTTTAAGAATCATGCTCCTATAACA ACAATGAAAATTTCATCTAAAAAGCAACA GTTGTATGTGAGTTCCAATGAAGGGGTTTC CCAGGTATCTCTGCACCGCTGCCACATCTA TGGTACAGCCTGTGCTGACTGCTGCCTGGC GCGGGACCCTTATTGCGCCTGGGATGGCCA TTCCTGTTCCAGATTCTACCCAACTGGGAA ACGGAGGAGCCGAAGACAAGATGTGAGAC ATGGAAACCCACTGACTCAATGCAGAGGA TTTAATCTAAAAGCATACAGAAATGCAGCT GAAATTGTGCAGTATGAGTAAAAAATAA CACCACTTTTCTGGAGTGTGCCCCCAAGTC TCCGCAGGCATCTATCAAGTGGCTGTTACA GAAAGACAAAGACAGGAGGAAAGAGGTT AAGCTGAATGAACGAATAATAGCCACTTC ACAGGGACTCCTGATCCGCTCTGTTCAGGG TTCTGACCAAGGACTTTATCACTGCATTGC TACAGAAATAGTTTCAAGCAGACCATAG CCAAGATCAACTTCAAAGTTTTAGATTCAG AAATGGTGGCTGTTGTGACGGACAAATGG TCCCCATGGACCTGGGCCAGCTCTGTGAGG GCTTTACCCTTCCACCCGAAGGACATCATG GGGGCATTCAGCCACTCAGAAATGCAGAT GATTAACCAATATTGCAAAGACACTCGGC AGCAACATCAGCAGGGAGATGAATCACAG AAAATGAGAGGGGACTATGGCAAGTTAAA GGCCCTCATCAATAGTCGGAAAAGTAGAA ACAGGAGGAATCAGTTGCCAGAGTCATAA |
| SEQ ID NO: 16 | Polynucleotide sequence corresponding to site 1 of Sema3C. Bases 430-441 of SEQ ID NO: 15. | AGAGGGAGGAGA |
| SEQ ID NO: 17 | Polynucleotide sequence corresponding to site 2 of Sema3C. Bases 1645-1656 of SEQ ID NO: 15. | AGGAGCCGAAGA |
| SEQ ID NO: 18 | Polynucleotide sequence corresponding to site 3 of Sema3C. Bases 2224-2235 of SEQ ID NO: 15. | AGAAACAGGAGG |
| SEQ ID NO: 19 | Polynucleotide sequence corresponding to basic domain of Sema3C (SEQ ID NO: 5) | AAAATGAGAGGGGACTATGGCAAGTTAAA GGCCCTCATCAATAGTCGGAAAAGTAGAA ACAGGAGG |
| SEQ ID NO: 20 | cDNA sequence of Sema3C-p65 (SEQ ID NO: 6) | ATGGCATTCCGGACAATTTGCGTGTTGGTT GGAGTATTTATTGTTCTATCTGTGTGAAA GGATCTTCCCAGCCCCAAGCAAGAGTTTAT TTAACATTTGATGAACTTCGAGAAACCAAG ACCTCTGAATACTTCAGCCTTTCCCACCAT CCTTTAGACTACAGGATTTTATTAATGGAT GAAGATCAGGACCGGATATATGTGGGAAG CAAAGATCACATTCTTTCCCTGAATATTAA CAATATAAGTCAAGAAGCTTTGAGTGTTTT CTGGCCAGCATCTACAATCAAAGTTGAAG AATGCAAAATGGCTGGCAAAGATCCCACA CACGGCTGTGGGAACTTTGTCCGTGTAATT CAGACTTTCAATCGCACACATTTGTATGTC TGTGGGAGTGGCGCTTTCAGTCCTGTCTGT ACTTACTTGAACAGAGGGAGGAGATCAGA GGACCAAGTTTTCATGATTGACTCCAAGTG TGAATCTGGAAAAGGACGCTGCTCTTTCAA CCCCAACGTGAACACGGTGTCTGTTATGAT CAATGAGGAGCTTTTCTCTGGAATGTATAT AGATTTCATGGGACAGATGCTGCTATTTT TCGAAGTTTAACCAAGAGGAATGCGGTCA GAACTGATCAACATAATTCCAAATGGCTAA GTGAACCTATGTTTGTAGATGCACATGTCA TCCCAGATGGTACTGATCCAAATGATGCTA |

Sequence table

| SEQ ID # | Sequence Identity | Sequence |
|---|---|---|
| | | AGGTGTACTTCTTCTTCAAAGAAAAACTGA<br>CTGACAATAACAGGAGCACGAAACAGATT<br>CATTCCATGATTGCTCGAATATGTCCTAAT<br>GACACTGGTGGACTGCGTAGCCTTGTCAAC<br>AAGTGGACCACTTTCTTAAAGGCGAGGCTG<br>GTGTGCTCGGTAACAGATGAAGACGGCCC<br>AGAAACACACTTTGATGAATTAGAGGATG<br>TGTTTCTGCTGGAAACTGATAACCCGAGGA<br>CAACACTAGTGTATGGCATTTTTACAACAT<br>CAAGCTCAGTTTTCAAAGGATCAGCCGTGT<br>GTGTGTATCATTTATCTGATATACAGACTG<br>TGTTTAATGGGCCTTTTGCCCACAAAGAAG<br>GGCCCAATCATCAGCTGATTTCCTATCAGG<br>GCAGAATTCCATATCCTCGCCCTGGAACTT<br>GTCCAGGAGGAGCATTTACACCCAATATGC<br>GAACCACCAAGGAGTTCCCAGATGATGTT<br>GTCACTTTTATTCGGAACCATCCTCTCATGT<br>ACAATTCCATCTACCCAATCCACAAAAGGC<br>CTTTGATTGTTCGTATTGGCACTGACTACA<br>AGTATACAAAGATAGCTGTGGATCGAGTG<br>AACGCTGCTGATGGGAGATACCATGTCCTG<br>TTTCTCGGAACAGATCGGGGTACTGTGCAA<br>AAAGTGGTTGTTCTTCCTACTAACAACTCT<br>GTCAGTGGCGAGCTCATTCTGGAGGAGCTG<br>GAAGTCTTTAAGAATCATGCTCCTATAACA<br>ACAATGAAAATTTCATCTAAAAAGCAACA<br>GTTGTATGTGAGTTCCAATGAAGGGGTTTC<br>CCAGGTATCTCTGCACCGCTGCCACATCTA<br>TGGTACAGCCTGTGCTGACTGCTGCCTGGC<br>GCGGGACCCTTATTGCGCCTGGGATGGCCA<br>TTCCTGTTCCAGATTCTACCCAACTGGGAA<br>ACGG |
| SEQ ID NO: 21 | cDNA sequence of Sema3C-p65-FC (SEQ ID NO: 7) | ATGGCATTCCGGACAATTTGCGTGTTGGTT<br>GGAGTATTTATTTGTTCTATCTGTGTGAAA<br>GGATCTTCCCAGCCCCAAGCAAGAGTTTAT<br>TTAACATTTGATGAACTTCGAGAAACCAAG<br>ACCTCTGAATACTTCAGCCTTTCCCACCAT<br>CCTTTTAGACTACAGGATTTTATTAATGGAT<br>GAAGATCAGGACCGGATATATGTGGGAAG<br>CAAAGATCACATTCTTTCCCTGAATATTAA<br>CAATATAAGTCAAGAAGCTTTGAGTGTTTT<br>CTGGCCAGCATCTACAATCAAAGTTGAAG<br>AATGCAAAATGGCTGGCAAAGATCCCACA<br>CACGGCTGTGGGAACTTTGTCCGTGTAATT<br>CAGACTTTCAATCGCACACATTTGTATGTC<br>TGTGGGAGTGGCGCTTTCAGTCCTGTCTGT<br>ACTTACTTGAACAGAGGGAGGAGATCAGA<br>GGACCAAGTTTTCATGATTGACTCCAAGTG<br>TGAATCTGGAAAAGGACGCTGCTCTTTCAA<br>CCCCAACGTGAACACGGTGTCTGTTATGAT<br>CAATGAGGAGCTTTTCTCTGGAATGTATAT<br>AGATTTCATGGGGACAGATGCTGCTATTTT<br>TCGAAGTTTAACCAAGAGGAATGCGGTCA<br>GAACTGATCAACATAATTCCAAATGGCTAA<br>GTGAACCTATGTTTGTAGATGCACATGTCA<br>TCCCAGATGGTACTGATCCAAATGATGCTA<br>AGGTGTACTTCTTCTTCAAAGAAAAACTGA<br>CTGACAATAACAGGAGCACGAAACAGATT<br>CATTCCATGATTGCTCGAATATGTCCTAAT<br>GACACTGGTGGACTGCGTAGCCTTGTCAAC<br>AAGTGGACCACTTTCTTAAAGGCGAGGCTG<br>GTGTGCTCGGTAACAGATGAAGACGGCCC<br>AGAAACACACTTTGATGAATTAGAGGATG<br>TGTTTCTGCTGGAAACTGATAACCCGAGGA<br>CAACACTAGTGTATGGCATTTTTACAACAT<br>CAAGCTCAGTTTTCAAAGGATCAGCCGTGT<br>GTGTGTATCATTTATCTGATATACAGACTG<br>TGTTTAATGGGCCTTTTGCCCACAAAGAAG<br>GGCCCAATCATCAGCTGATTTCCTATCAGG<br>GCAGAATTCCATATCCTCGCCCTGGAACTT<br>GTCCAGGAGGAGCATTTACACCCAATATGC<br>GAACCACCAAGGAGTTCCCAGATGATGTT<br>GTCACTTTTATTCGGAACCATCCTCTCATGT<br>ACAATTCCATCTACCCAATCCACAAAAGGC<br>CTTTGATTGTTCGTATTGGCACTGACTACA<br>AGTATACAAAGATAGCTGTGGATCGAGTG<br>AACGCTGCTGATGGGAGATACCATGTCCTG<br>TTTCTCGGAACAGATCGGGGTACTGTGCAA<br>AAAGTGGTTGTTCTTCCTACTAACAACTCT<br>GTCAGTGGCGAGCTCATTCTGGAGGAGCTG<br>GAAGTCTTTAAGAATCATGCTCCTATAACA<br>ACAATGAAAATTTCATCTAAAAAGCAACA<br>GTTGTATGTGAGTTCCAATGAAGGGGTTTC<br>CCAGGTATCTCTGCACCGCTGCCACATCTA<br>TGGTACAGCCTGTGCTGACTGCTGCCTGGC<br>GCGGGACCCTTATTGCGCCTGGGATGGCCA<br>TTCCTGTTCCAGATTCTACCCAACTGGGAA<br>ACGGCTCGAGGACAAAACTCACACATGCC<br>CACCGTGCCCAGCACCTGAACTCCTGGGGG<br>GACCGTCAGTCTTCCTCTTCCCCCCAAAAC<br>CCAAGGACACCCTCATGATCTCCCGGACCC<br>CTGAGGTCACATGCGTGGTGGTGGACGTG<br>AGCCACGAAGACCCTGAGGTCAAGTTCAA<br>CTGGTACGTGGACGGCGTGGAGGTGCATA<br>ATGCCAAGACAAAGCCGCGGGAGGAGCAG<br>TACAACAGCACGTACCGTGTGGTCAGCGTC<br>CTCACCGTCCTGCACCAGGACTGGCTGAAT<br>GGCAAGGAGTACAAGTGCAAGGTCTCCAA<br>CAAAGCCCTCCCAGCCCCCATCGAGAAAA<br>CCATCTCCAAAGCCAAAGGGCAGCCCCGA<br>GAACCACAGGTGTACACCCTGCCCCCATCC<br>CGGGAGGAGATGACCAAGAACCAGGTCAG<br>CCTGACCTGCCTGGTCAAAGGCTTCTATCC<br>CAGCGACATCGCCGTGGAGTGGGAGAGCA<br>ATGGGCAGCCGGAGAACAACTACAAGACC<br>ACGCCTCCCGTGCTGGACTCCGACGGCTCC<br>TTCTTCCTCTATAGCAAGCTCACCGTGGAC<br>AAGAGCAGGTGGCAGCAGGGGAACGTCTT<br>CTCATGCTCCGTGATGCATGAGGCTCTGCA<br>CAACCACTACACGCAGAAGAGCCTCTCCCT<br>GTCCCCGGGTAAATGA |
| SEQ ID NO: 22 | cDNA sequence of UNCL-Sema3C-Fc (SEQ ID NO: 8) | ATGGCATTCCGGACAATTTGCGTGTTGGTT<br>GGAGTATTTATTTGTTCTATCTGTGTGAAA<br>GGATCTTCCCAGCCCCAAGCAAGAGTTTAT<br>TTAACATTTGATGAACTTCGAGAAACCAAG<br>ACCTCTGAATACTTCAGCCTTTCCCACCAT<br>CCTTTTAGACTACAGGATTTTATTAATGGAT<br>GAAGATCAGGACCGGATATATGTGGGAAG<br>CAAAGATCACATTCTTTCCCTGAATATTAA<br>CAATATAAGTCAAGAAGCTTTGAGTGTTTT<br>CTGGCCAGCATCTACAATCAAAGTTGAAG<br>AATGCAAAATGGCTGGCAAAGATCCCACA<br>CACGGCTGTGGGAACTTTGTCCGTGTAATT<br>CAGACTTTCAATCGCACACATTTGTATGTC<br>TGTGGGAGTGGCGCTTTCAGTCCTGTCTGT<br>ACTTACTTGAACAGAGGGAGGAGATCAGA<br>GGACCAAGTTTTCATGATTGACTCCAAGTG<br>TGAATCTGGAAAAGGACGCTGCTCTTTCAA<br>CCCCAACGTGAACACGGTGTCTGTTATGAT<br>CAATGAGGAGCTTTTCTCTGGAATGTATAT<br>AGATTTCATGGGGACAGATGCTGCTATTTT<br>TCGAAGTTTAACCAAGAGGAATGCGGTCA<br>GAACTGATCAACATAATTCCAAATGGCTAA<br>GTGAACCTATGTTTGTAGATGCACATGTCA<br>TCCCAGATGGTACTGATCCAAATGATGCTA<br>AGGTGTACTTCTTCTTCAAAGAAAAACTGA<br>CTGACAATAACAGGAGCACGAAACAGATT<br>CATTCCATGATTGCTCGAATATGTCCTAAT<br>GACACTGGTGGACTGCGTAGCCTTGTCAAC<br>AAGTGGACCACTTTCTTAAAGGCGAGGCTG<br>GTGTGCTCGGTAACAGATGAAGACGGCCC<br>AGAAACACACTTTGATGAATTAGAGGATG<br>TGTTTCTGCTGGAAACTGATAACCCGAGGA<br>CAACACTAGTGTATGGCATTTTTACAACAT |

Sequence table

| SEQ ID # | Sequence Identity | Sequence |
|---|---|---|
| | | CAAGCTCAGTTTTCAAAGGATCAGCCGTGT |
| | | GTGTGTATCATTTATCTGATATACAGACTG |
| | | TGTTTAATGGGCCTTTTGCCCACAAAGAAG |
| | | GGCCCAATCATCAGCTGATTTCCTATCAGG |
| | | GCAGAATTCCATATCCTCGCCCTGGAACTT |
| | | GTCCAGGAGGAGCATTTACACCCAATATGC |
| | | GAACCACCAAGGAGTTCCCAGATGATGTT |
| | | GTCACTTTTATTCGGAACCATCCTCTCATGT |
| | | ACAATTCCATCTACCCAATCCACAAAAGGC |
| | | CTTTGATTGTTCGTATTGGCACTGACTACA |
| | | AGTATACAAAGATAGCTGTGGATCGAGTG |
| | | AACGCTGCTGATGGGAGATACCATGTCCTG |
| | | TTTCTCGGAACAGATCGGGGTACTGTGCAA |
| | | AAAGTGGTTGTTCTTCCTACTAACAACTCT |
| | | GTCAGTGGCGAGCTCATTCTGGAGGAGCTG |
| | | GAAGTCTTTAAGAATCATGCTCCTATAACA |
| | | ACAATGAAATTTCATCTAAAAAGCAACA |
| | | GTTGTATGTGAGTTCCAATGAAGGGGTTTC |
| | | CCAGGTATCTCTGCACCGCTGCCACATCTA |
| | | TGGTACAGCCTGTGCTGACTGCTGCCTGGC |
| | | GCGGGACCCTTATTGCGCCTGGGATGGCCA |
| | | TTCCTGTTCCAGATTCTACCCAACTGGGAA |
| | | ACGGAAGAGCAAAAACAAGATGTGAGAC |
| | | ATGGAAACCCACTGACTCAATGCAGAGGA |
| | | TTTAATCTAAAAGCATACAGAAATGCAGCT |
| | | GAAATTGTGCAGTATGGAGTAAAAAATAA |
| | | CACCACTTTTCTGGAGTGTGCCCCCAAGTC |
| | | TCCGCAGGCATCTATCAAGTGGCTGTTACA |
| | | GAAAGACAAAGACAGGAGGAAAGAGGTT |
| | | AAGCTGAATGAACGAATAATAGCCACTTC |
| | | ACAGGGACTCCTGATCCGCTCTGTTCAGGG |
| | | TTCTGACCAAGGACTTTATCACTGCATTGC |
| | | TACAGAAAATAGTTTCAAGCAGACCATAG |
| | | CCAAGATCAACTTCAAAGTTTTAGATTCAG |
| | | AAAATGGTGGCTGTTGTGACGGACAAATGG |
| | | TCCCCATGGACCTGGGCCAGCTCTGTGAGG |
| | | GCTTTACCCTTCCACCCGAAGGACATCATG |
| | | GGGGCATTCAGCCACTCAGAAATGCAGAT |
| | | GATTAACCAATATTGCAAAGACACTCGGC |
| | | AGCAACATCAGCAGGGAGATGAATCACAG |
| | | AAAATGAGAGGGACTATGGCAAGTTAAA |
| | | GGCCCTCATCAATAGTCTCGAGGACAAAA |
| | | CTCACACATGCCCACCGTGCCCAGCACCTG |
| | | AACTCCTGGGGGACCGTCAGTCTTCCTCT |
| | | TCCCCCCAAAACCAAGGACACCCTCATGA |
| | | TCTCCCGGACCCCTGAGGTCACATGCGTGG |
| | | TGGTGGACGTGAGCCACGAAGACCCTGAG |
| | | GTCAAGTTCAACTGGTACGTGGACGGCGTG |
| | | GAGGTGCATAATGCCAAGACAAAGCCGCG |
| | | GGAGGAGCAGTACAACAGCACGTACCGTG |
| | | TGGTCAGCGTCCTCACCGTCCTGCACCAGG |
| | | ACTGGCTGAATGGCAAGGAGTACAAGTGC |
| | | AAGGTCTCCAACAAAGCCCTCCCAGCCCCC |
| | | ATCGAGAAAACCATCTCCAAAGCCAAAGG |
| | | GCAGCCCCGAGAACCACAGGTGTACACCC |
| | | TGCCCCCATCCCGGGAGGAGATGACCAAG |
| | | AACCAGGTCAGCCTGACCTGCCTGGTCAAA |
| | | GGCTTCTATCCCAGCGACATCGCCGTGGAG |
| | | TGGGAGAGCAATGGGCAGCCGGAGAACAA |
| | | CTACAAGACCACGCCTCCCGTGCTGGACTC |
| | | CGACGGCTCCTTCTTCCTCTATAGCAAGCT |
| | | CACCGTGGACAAGAGCAGGTGGCAGCAGG |
| | | GGAACGTCTTCTCATGCTCCGTGATGCATG |
| | | AGGCTCTGCACAACCACTACACGCAGAAG |
| | | AGCCTCTCCCTGTCCCGGGTAAATGA |
| SEQ ID NO: 23 | cDNA sequence of UNCL-Sema3C-myc-6His (SEQ ID NO: 9) | ATGGCATTCCGGACAATTTGCGTGTTGGTT GGAGTATTTATTTGTTCTATCTGTGTGAAA GGATCTTCCCAGCCCCAAGCAAGAGTTTAT TTACATTTGATGAACTTCGAGAAACCAAG ACCTCTGAATACTTCAGCCTTTCCCCACCAT CCTTTAGACTACAGGATTTATTAATGGAT GAAGATCAGGACCGGATATATGTGGGAAG |

| SEQ ID # | Sequence Identity | Sequence |
|---|---|---|
| | | CAAAGATCACATTCTTTCCCTGAATATTAA |
| | | CAATATAAGTCAAGAAGCTTTGAGTGTTTT |
| | | CTGGCCAGCATCTACAATCAAAGTTGAAG |
| | | AATGCAAAATGGCTGGCAAAGATCCCACA |
| | | CACGGCTGTGGGAACTTTGTCCGTGTAATT |
| | | CAGACTTTCAATCGCACACATTTGTATGTC |
| | | TGTGGGAGTGGCGCTTTCAGTCCTGTCTGT |
| | | ACTTACTTGAACAGAGGGAGGAGATCAGA |
| | | GGACCAAGTTTTCATGATTGACTCCAAGTG |
| | | TGAATCTGGAAAAGGACGCTGCTCTTTCAA |
| | | CCCCAACGTGAACACGGTGTCTGTTATGAT |
| | | CAATGAGGAGCTTTTCTCTGGAATGTATAT |
| | | AGATTTCATGGGGACAGATGCTGCTATTTT |
| | | TCGAAGTTTAACCAAGAGGAATGCGGTCA |
| | | GAACTGATCAACATAATTCCAAATGGCTAA |
| | | GTGAACCTATGTTTGTAGATGCACATGTCA |
| | | TCCCAGATGGTACTGATCCAAATGATGCTA |
| | | AGGTGTACTTCTTCTTCAAAGAAAAACTGA |
| | | CTGACAATAACAGGAGCACGAAACAGATT |
| | | CATTCCATGATTGCTCGAATATGTCCTAAT |
| | | GACACTGGTGGACTGCGTAGCCTTGTCAAC |
| | | AAGTGGACCACTTTCTTAAAGGCGAGGCTG |
| | | GTGTGCTCGGTAACAGATGAAGACGGCCC |
| | | AGAAACAACTTTTGATGAATTAGAGGATG |
| | | TGTTTCTGCTGGAAACTGATAACCCGAGGA |
| | | CAACACTAGTGTATGGCATTTTTACAACAT |
| | | CAAGCTCAGTTTTCAAAGGATCAGCCGTGT |
| | | GTGTGTATCATTTATCTGATATACAGACTG |
| | | TGTTTAATGGGCCTTTTGCCCACAAAGAAG |
| | | GGCCCAATCATCAGCTGATTTCCTATCAGG |
| | | GCAGAATTCCATATCCTCGCCCTGGAACTT |
| | | GTCCAGGAGGAGCATTTACACCCAATATGC |
| | | GAACCACCAAGGAGTTCCCAGATGATGTT |
| | | GTCACTTTTATTCGGAACCATCCTCTCATGT |
| | | ACAATTCCATCTACCCAATCCACAAAAGGC |
| | | CTTTGATTGTTCGTATTGGCACTGACTACA |
| | | AGTATACAAAGATAGCTGTGGATCGAGTG |
| | | AACGCTGCTGATGGGAGATACCATGTCCTG |
| | | TTTCTCGGAACAGATCGGGGTACTGTGCAA |
| | | AAAGTGGTTGTTCTTCCTACTAACAACTCT |
| | | GTCAGTGGCGAGCTCATTCTGGAGGAGCTG |
| | | GAAGTCTTTAAGAATCATGCTCCTATAACA |
| | | ACAATGAAATTTCATCTAAAAAGCAACA |
| | | GTTGTATGTGAGTTCCAATGAAGGGGTTTC |
| | | CCAGGTATCTCTGCACCGCTGCCACATCTA |
| | | TGGTACAGCCTGTGCTGACTGCTGCCTGGC |
| | | GCGGGACCCTTATTGCGCCTGGGATGGCCA |
| | | TTCCTGTTCCAGATTCTACCCAACTGGGAA |
| | | ACGGAAGAGCAAAAACAAGATGTGAGAC |
| | | ATGGAAACCCACTGACTCAATGCAGAGGA |
| | | TTTAATCTAAAAGCATACAGAAATGCAGCT |
| | | GAAATTGTGCAGTATGGAGTAAAAAATAA |
| | | CACCACTTTTCTGGAGTGTGCCCCCAAGTC |
| | | TCCGCAGGCATCTATCAAGTGGCTGTTACA |
| | | GAAAGACAAAGACAGGAGGAAAGAGGTT |
| | | AAGCTGAATGAACGAATAATAGCCACTTC |
| | | ACAGGGACTCCTGATCCGCTCTGTTCAGGG |
| | | TTCTGACCAAGGACTTTATCACTGCATTGC |
| | | TACAGAAAATAGTTTCAAGCAGACCATAG |
| | | CCAAGATCAACTTCAAAGTTTTAGATTCAG |
| | | AAAATGGTGGCTGTTGTGACGGACAAATGG |
| | | TCCCCATGGACCTGGGCCAGCTCTGTGAGG |
| | | GCTTTACCCTTCCACCCGAAGGACATCATG |
| | | GGGGCATTCAGCCACTCAGAAATGCAGAT |
| | | GATTAACCAATATTGCAAAGACACTCGGC |
| | | AGCAACATCAGCAGGGAGATGAATCACAG |
| | | AAAATGAGAGGGACTATGGCAAGTTAAA |
| | | GGCCCTCATCAATAGTCTCGAGTCTAGAGG |
| | | GCCCTTCGAACAAAAACTCATCTCAGAAG |
| | | AGGATCTGAATATGCATACCGGTCATCATC |
| | | ACCATCACCATTGA |

Sequence table

| SEQ ID # | Sequence Identity | Sequence |
|---|---|---|
| SEQ ID NO: 24 | 5'-primer according to step 1 of Example 1 | GGGAAACGGAGGAGCAAAAGACAAGATGTGAGACATGG |
| SEQ ID NO: 25 | 3'-primer according to step 1 of Example 1 | CCATGTCTCACATCTTGTCTTTTGCTCCTCCGTTTCCC |
| SEQ ID NO: 26 | 5'-primer according to step 2 of Example 1 | TACCCAACTGGGAAACGGAAGAGCAAAAGACAAGATGTGAGACA TGG |
| SEQ ID NO: 27 | 3'-primer according to step 2 of Example 1 | CCATGTCTCACATCTTGTCTTTTGCTCTTCCGTTTCCCAGTTGGGTA |
| SEQ ID NO: 28 | 5'-primer according to step 3 of Example 1 | GGGAAACGGAAGAGCAAAAACAAGATGTGAGACATGGAAACCC |
| SEQ ID NO: 29 | 3'-primer according to step 3 of Example 1 | GGGTTTCCATGTCTCACATCTTGTTTTTGCTCTTCCGTTTCCC |
| SEQ ID NO: 30 | 5'-primer for ligation to pGem T-easy according to Example 1 | CGGGATCCACCATGGCATCGGACAATTTG |
| SEQ ID NO: 31 | 3'-primer for ligation to pGem T-easy according to Example 1 | CGCTCGAGACTATTGATGAGGGCCTTTAACTT |
| SEQ ID NO: 32 | C-terminus of SEQ ID NO: 15 truncated in UNCL-Sema3C/FC | CGGAAAAGTAGAAACAGGAGGAATCAGTTGCCAGAGTCATAA |
| SEQ ID NO: 33 | Sema3C with a C-terminus truncation deleting FPPC cleavage site 3 | MAFRTICVLVGVFICSICVKGSSQPQARVYLTFDELRETKTSEYFSLSHHPLDYRILLMDEDQDRIYVGSKDHILSLNINNISQEALSVFWPASTIKVEECKMAGKDPTHGCGNFVRVIQTFNRTHLYVCGSGAFSPVCTYLNRGRRSEDQVFMIDSKCESGKGRCSFNPNVNTVSVMINEELFSGMYIDFMGTDAAIFRSLTKRNAVRTDQHNSKWLSEPMFVDAHVIPDGTDPNDAKVYFFFKEKLTDNNRSTKQIHSMIARICPNDTGGLRSLVNKWTTFLKARLVCSVTDEDGPETHFDELEDVFLLETDNPRTTLVYGIFTTSSSVFKGSAVCVYHLSDIQTVFNGPFAHKEGPNHQLISYQGRIPYPRPGTCPGGAFTPNMRTTKEFPDDVVTFIRNHPLMYNSIYPIHKRPLIVRIGTDYKYTKIAVDRVNAADGRYHVLFLGTDRGTVQKVVVLPTNNSVSGELILEELEVFKNHAPITTMKISSKKQQLYVSSNEGVSQVSLHRCHIYGTACADCCLARDPYCAWDGHSCSRFYPTGKRRSRRQDVRHGNPLTQCRGFNLKAYRNAAEIVQYGVKNNTTFLECAPKSPQASIKWLLQKDKDRRKEVKLNERIIATSQGLLIRSVQGSDQGLYHCIATENSFKQTIAKINFKVLDSEMVAVVTDKWSPWTWASSVRALPFHPKDIMGAFSHSEMQMINQYCKDTRQQHQQGDESQKMRGDYGKLKALINS |
| SEQ ID NO: 34 | C-terminus of SEQ ID NO: 1 truncated in UNCL-Sema3C/FC | RKSRNRRNQLPES |
| SEQ ID NO: 35 | Sema3C with a C-terminus truncation deleting FPPC cleavage site 3 and a modification of FPPC cleavage site 2 | MAFRTICVLVGVFICSICVKGSSQPQARVYLTFDELRETKTSEYFSLSHHPLDYRILLMDEDQDRIYVGSKDHILSLNINNISQEALSVFWPASTIKVEECKMAGKDPTHGCGNFVRVIQTFNRTHLYVCGSGAFSPVCTYLNRGRRSEDQVFMIDSKCESGKGRCSFNPNVNTVSVMINEELFSGMYIDFMGTDAAIFRSLTKRNAVRTDQHNSKWLSEPMFVDAHVIPDGTDPNDAKVYFFFKEKLTDNNRSTKQIHSMIARICPNDTGGLRSLVNKWTTFLKARLVCSVTDEDGPETHFDELEDVFLLETDNPRTTLVYGIFTTSSSVFKGSAVCVYHLSDIQTVFNGPFAHKEGPNHQLISYQGRIPYPRPGTCPGGAFTPNMRTTKEFPDDVVTFIRNHPLMYNSIYPIHKRPLIVRIGTDYKYTKIAVDRVNAADGRYHVLFLGTDRGTVQKVVVLPTNNSVSGELILEELEVFKNHAPITTMKISSKKQQLYVSSNEGVSQVSLHRCHIYGTACADCCLARDPYCAWDGHSCSRFYPTGKRKSKKQDVRHGNPLTQCRGFNLKAYRNAAEIVQYGVKNNTTFLECAPKSPQASIKWLLQKDKDRRKEVKLNERIIATSQGLLIRSVQGSDQGLYHCIATENSFKQTIAKINFKVLDSEMVAVVTDKWSPWTWASSVRALPFHPKDIMGAFSHSEMQMINQYCKDTRQQHQQGDESQKMRGDYGKLKALINS |
| SEQ ID NO: 36 | C-terminus of SEQ ID NO: 1 from FPPC cleavage site 3 and downstream | RNRRNQLPES |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating age-related macular degeneration and/or reducing abnormal angiogenesis and lymphangiogenesis in an eye of a patient comprising administering into an eye of a subject in need an effective amount of a variant of Semaphorin 3C (Sema3C) which has at least 80%, 90%, 95%, or 99% sequence identity with the amino acid set forth in SEQ ID NO: 1, wherein said variant comprises at least one modification in furin-like pro-protein convertase cleavage site 2 consisting of amino acid residues 549-552; and wherein said modification renders said variant resistant to cleavage at said cleavage site 2 and a pharmaceutically effective carrier.

2. The method of claim 1, wherein the age-related macular degeneration comprises geographic atrophy, dry age-related macular degeneration, choroidal neovascularization, or exudative age-related macular degeneration.

3. The method of claim 1, wherein said modification is a modification of at least one arginine residue within said furin-like pro-protein convertase cleavage site 2.

4. The method of claim 1, wherein said modification is a modification of at least one arginine residue within said furin-like pro-protein convertase cleavage site to a lysine residue.

5. The method of claim 1, wherein said variant further comprises at least one modification in a basic domain of said variant, the basic domain having an amino acid sequence as set forth in SEQ ID NO: 5.

6. The method of claim 1, wherein said at least one modification in cleavage site 2 is a modification as set forth in SEQ ID NO: 13.

7. The method of claim 1, wherein said at least one modification is a truncation of at least part of the C-terminus of said variant as set forth in SEQ ID NO: 34.

8. The method of claim 1, wherein said variant further comprises a modification which is a truncation of at least part of the C-terminus of said variant as set forth in SEQ ID NO: 34.

9. The method of claim 1, wherein the variant of Sema3C is as set forth in SEQ ID NO: 8.

10. The method of claim 1, wherein said administration into the eye of the subject in need is by a direct injection into the eye, by ocular, intraocular application or by application of eye drops.

11. The method of claim 1, wherein said Sema3C variant is in a complex comprising the Sema3C or variant thereof and a non-proteinaceous or proteinaceous moiety.

12. The method of claim 11, wherein the non-proteinaceous moiety is polyethylene glycol (PEG) or derivative thereof, polyvinyl pyrrolidone (PVP), divinyl ether, maleic anhydride copolymer (DIVEMA), polysialic acid (PSA), poly(styrene comaleic anhydride) (SMA), hyaluronic acid (HA), alginic acid (AA), polyhydroxyethyl methacrylate (Poly-HEMA), glyme or polyisopropylacrylamide or any combination thereof.

13. The method of claim 11, wherein the proteinaceous moiety is a peptide, polypeptide, or an immunoglobulin, or a part thereof.

14. The method of claim 13, wherein the immunoglobulin is an Fc region.

15. The method of claim 1, wherein said variant of Sema3C is administered together with another therapeutic agent or with another treatment for age-related macular degeneration and/or reducing abnormal angiogenesis and lymphangiogenesis.

16. The method of claim 15, wherein the another therapeutic agent is a VEGF inhibitor, or one or more inhibitors of FGF, PDGF, FGFR, VEGFR, or PDGFR, wherein the another therapeutic agent is administered simultaneously or consecutively with the Sema3C variant.

17. The method of claim 1, wherein the subject in need does not respond to an anti-VEGF, FGF, PDGF, FGFR, VEGFR, or PDGFR therapy.

18. The method of claim 1, wherein the subject in need developed resistance to VEGF, FGF, PDGF, FGFR, VEGFR, PDGFR therapy.

19. The method of claim 10, wherein said administration into the eye of the subject is by intravitreal application.

20. The method of claim 1, wherein said method comprises a method of treating age-related macular degeneration and/or reducing lymphangiogenesis in an eye of a patient.

* * * * *

SEQUENCE LISTING

<160> NUMBER OF SEQ ID NOS: 36

<210> SEQ ID NO 1
<211> LENGTH: 751
<212> TYPE: PRT
<213> ORGANISM: Homo sapiens

<400> SEQUENCE: 1

```
Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
        355                 360                 365
```

Arg Ile Pro Tyr Pro Arg Pro Gly Thr Cys Pro Gly Gly Ala Phe Thr
370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
                420                 425                 430

Ala Val Asp Arg Val Asn Ala Ala Asp Gly Arg Tyr His Val Leu Phe
                435                 440                 445

Leu Gly Thr Asp Arg Gly Thr Val Gln Lys Val Val Leu Pro Thr
450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
                500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
                580                 585                 590

Ala Pro Lys Ser Pro Gln Ala Ser Ile Lys Trp Leu Leu Gln Lys Asp
                595                 600                 605

Lys Asp Arg Arg Lys Glu Val Lys Leu Asn Glu Arg Ile Ile Ala Thr
610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Thr Asp
                660                 665                 670

Lys Trp Ser Pro Trp Thr Trp Ala Ser Ser Val Arg Ala Leu Pro Phe
                675                 680                 685

His Pro Lys Asp Ile Met Gly Ala Phe Ser His Ser Glu Met Gln Met
690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Arg Lys Ser Arg Asn Arg Arg Asn Gln Leu Pro Glu Ser
                740                 745                 750

<210> SEQ ID NO 2
<211> LENGTH: 4
<212> TYPE: PRT
<213> ORGANISM: Homo sapiens

<400> SEQUENCE: 2

```
Arg Gly Arg Arg
1

<210> SEQ ID NO 3
<211> LENGTH: 4
<212> TYPE: PRT
<213> ORGANISM: Homo sapiens

<400> SEQUENCE: 3

Arg Ser Arg Arg
1

<210> SEQ ID NO 4
<211> LENGTH: 4
<212> TYPE: PRT
<213> ORGANISM: Homo sapiens

<400> SEQUENCE: 4

Arg Asn Arg Arg
1

<210> SEQ ID NO 5
<211> LENGTH: 22
<212> TYPE: PRT
<213> ORGANISM: Homo sapiens

<400> SEQUENCE: 5

Lys Met Arg Gly Asp Tyr Gly Lys Leu Lys Ala Leu Ile Asn Ser Arg
1               5                   10                  15

Lys Ser Arg Asn Arg Arg
            20

<210> SEQ ID NO 6
<211> LENGTH: 548
<212> TYPE: PRT
<213> ORGANISM: Homo sapiens

<400> SEQUENCE: 6

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
```

```
                    165                 170                 175
Val Met Ile Asn Glu Leu Phe Ser Gly Met Tyr Ile Asp Phe Met
                180                 185                 190

Gly Thr Asp Ala Ala Ile Phe Arg Ser Leu Thr Lys Arg Asn Ala Val
            195                 200                 205

Arg Thr Asp Gln His Asn Ser Lys Trp Leu Ser Glu Pro Met Phe Val
        210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Leu Pro Thr
    450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
    530                 535                 540

Thr Gly Lys Arg
545

<210> SEQ ID NO 7
<211> LENGTH: 777
<212> TYPE: PRT
<213> ORGANISM: Homo sapiens
```

<400> SEQUENCE: 7

```
Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
```

```
                405                 410                 415
Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
        435                 440                 445

Leu Gly Thr Asp Arg Gly Thr Val Gln Lys Val Val Leu Pro Thr
    450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
        515                 520                 525

Asp Pro Tyr Cys Ala Trp Asp Gly His Ser Cys Ser Arg Phe Tyr Pro
    530                 535                 540

Thr Gly Lys Arg Leu Glu Asp Lys Thr His Thr Cys Pro Pro Cys Pro
545                 550                 555                 560

Ala Pro Glu Leu Leu Gly Gly Pro Ser Val Phe Leu Phe Pro Pro Lys
                565                 570                 575

Pro Lys Asp Thr Leu Met Ile Ser Arg Thr Pro Glu Val Thr Cys Val
            580                 585                 590

Val Val Asp Val Ser His Glu Asp Pro Glu Val Lys Phe Asn Trp Tyr
        595                 600                 605

Val Asp Gly Val Glu Val His Asn Ala Lys Thr Lys Pro Arg Glu Glu
    610                 615                 620

Gln Tyr Asn Ser Thr Tyr Arg Val Val Ser Val Leu Thr Val Leu His
625                 630                 635                 640

Gln Asp Trp Leu Asn Gly Lys Glu Tyr Lys Cys Lys Val Ser Asn Lys
                645                 650                 655

Ala Leu Pro Ala Pro Ile Glu Lys Thr Ile Ser Lys Ala Lys Gly Gln
            660                 665                 670

Pro Arg Glu Pro Gln Val Tyr Thr Leu Pro Pro Ser Arg Glu Glu Met
        675                 680                 685

Thr Lys Asn Gln Val Ser Leu Thr Cys Leu Val Lys Gly Phe Tyr Pro
    690                 695                 700

Ser Asp Ile Ala Val Glu Trp Glu Ser Asn Gly Gln Pro Glu Asn Asn
705                 710                 715                 720

Tyr Lys Thr Thr Pro Pro Val Leu Asp Ser Asp Gly Ser Phe Phe Leu
                725                 730                 735

Tyr Ser Lys Leu Thr Val Asp Lys Ser Arg Trp Gln Gln Gly Asn Val
            740                 745                 750

Phe Ser Cys Ser Val Met His Glu Ala Leu His Asn His Tyr Thr Gln
        755                 760                 765

Lys Ser Leu Ser Leu Ser Pro Gly Lys
    770                 775

<210> SEQ ID NO 8
<211> LENGTH: 967
<212> TYPE: PRT
<213> ORGANISM: Homo sapiens

<400> SEQUENCE: 8
```

-continued

```
Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
            115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
            165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
    195                 200                 205

Arg Thr Asp Gln His Asn Ser Lys Trp Leu Ser Glu Pro Met Phe Val
210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
            245                 250                 255

Gln Ile His Ser Met Ile Ala Arg Ile Cys Pro Asn Asp Thr Gly Gly
    260                 265                 270

Leu Arg Ser Leu Val Asn Lys Trp Thr Thr Phe Leu Lys Ala Arg Leu
    275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
    340                 345                 350

Phe Ala His Lys Glu Gly Pro Asn His Gln Leu Ile Ser Tyr Gln Gly
        355                 360                 365

Arg Ile Pro Tyr Pro Arg Pro Gly Thr Cys Pro Gly Gly Ala Phe Thr
    370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
            405                 410                 415

Arg Pro Leu Ile Val Arg Ile Gly Thr Asp Tyr Lys Tyr Thr Lys Ile
```

```
            420             425             430
Ala Val Asp Arg Val Asn Ala Ala Asp Gly Arg Tyr His Val Leu Phe
            435             440             445
Leu Gly Thr Asp Arg Gly Thr Val Gln Lys Val Val Leu Pro Thr
            450             455             460
Asn Asn Ser Val Ser Gly Glu Leu Ile Leu Glu Leu Glu Val Phe
465             470             475             480
Lys Asn His Ala Pro Ile Thr Thr Met Lys Ile Ser Ser Lys Lys Gln
                485             490             495
Gln Leu Tyr Val Ser Ser Asn Glu Gly Val Ser Gln Val Ser Leu His
            500             505             510
Arg Cys His Ile Tyr Gly Thr Ala Cys Ala Asp Cys Cys Leu Ala Arg
            515             520             525
Asp Pro Tyr Cys Ala Trp Asp Gly His Ser Cys Ser Arg Phe Tyr Pro
            530             535             540
Thr Gly Lys Arg Lys Ser Lys Lys Gln Asp Val Arg His Gly Asn Pro
545             550             555             560
Leu Thr Gln Cys Arg Gly Phe Asn Leu Lys Ala Tyr Arg Asn Ala Ala
                565             570             575
Glu Ile Val Gln Tyr Gly Val Lys Asn Asn Thr Thr Phe Leu Glu Cys
            580             585             590
Ala Pro Lys Ser Pro Gln Ala Ser Ile Lys Trp Leu Leu Gln Lys Asp
            595             600             605
Lys Asp Arg Arg Lys Glu Val Lys Leu Asn Glu Arg Ile Ile Ala Thr
            610             615             620
Ser Gln Gly Leu Leu Ile Arg Ser Val Gln Gly Ser Asp Gln Gly Leu
625             630             635             640
Tyr His Cys Ile Ala Thr Glu Asn Ser Phe Lys Gln Thr Ile Ala Lys
                645             650             655
Ile Asn Phe Lys Val Leu Asp Ser Glu Met Val Ala Val Thr Asp
            660             665             670
Lys Trp Ser Pro Trp Thr Trp Ala Ser Ser Val Arg Ala Leu Pro Phe
            675             680             685
His Pro Lys Asp Ile Met Gly Ala Phe Ser His Ser Glu Met Gln Met
            690             695             700
Ile Asn Gln Tyr Cys Lys Asp Thr Arg Gln Gln His Gln Gln Gly Asp
705             710             715             720
Glu Ser Gln Lys Met Arg Gly Asp Tyr Gly Lys Leu Lys Ala Leu Ile
                725             730             735
Asn Ser Leu Glu Asp Lys Thr His Thr Cys Pro Pro Cys Pro Ala Pro
            740             745             750
Glu Leu Leu Gly Gly Pro Ser Val Phe Leu Phe Pro Pro Lys Pro Lys
            755             760             765
Asp Thr Leu Met Ile Ser Arg Thr Pro Glu Val Thr Cys Val Val Val
            770             775             780
Asp Val Ser His Glu Asp Pro Glu Val Lys Phe Asn Trp Tyr Val Asp
785             790             795             800
Gly Val Glu Val His Asn Ala Lys Thr Lys Pro Arg Glu Glu Gln Tyr
                805             810             815
Asn Ser Thr Tyr Arg Val Val Ser Val Leu Thr Val Leu His Gln Asp
            820             825             830
Trp Leu Asn Gly Lys Glu Tyr Lys Cys Lys Val Ser Asn Lys Ala Leu
            835             840             845
```

```
Pro Ala Pro Ile Glu Lys Thr Ile Ser Lys Ala Lys Gly Gln Pro Arg
            850                 855                 860

Glu Pro Gln Val Tyr Thr Leu Pro Pro Ser Arg Glu Glu Met Thr Lys
865                 870                 875                 880

Asn Gln Val Ser Leu Thr Cys Leu Val Lys Gly Phe Tyr Pro Ser Asp
                885                 890                 895

Ile Ala Val Glu Trp Glu Ser Asn Gly Gln Pro Glu Asn Asn Tyr Lys
            900                 905                 910

Thr Thr Pro Pro Val Leu Asp Ser Asp Gly Ser Phe Phe Leu Tyr Ser
            915                 920                 925

Lys Leu Thr Val Asp Lys Ser Arg Trp Gln Gln Gly Asn Val Phe Ser
            930                 935                 940

Cys Ser Val Met His Glu Ala Leu His Asn His Tyr Thr Gln Lys Ser
945                 950                 955                 960

Leu Ser Leu Ser Pro Gly Lys
                965

<210> SEQ ID NO 9
<211> LENGTH: 766
<212> TYPE: PRT
<213> ORGANISM: Homo sapiens

<400> SEQUENCE: 9

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
            35                  40                  45

His His Pro Leu Asp Tyr Arg Ile Leu Leu Met Asp Glu Asp Gln Asp
        50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
            115                 120                 125

Val Cys Gly Ser Gly Ala Phe Ser Pro Val Cys Thr Tyr Leu Asn Arg
            130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
            195                 200                 205

Arg Thr Asp Gln His Asn Ser Lys Trp Leu Ser Glu Pro Met Phe Val
            210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
```

-continued

```
                245                 250                 255
Gln Ile His Ser Met Ile Ala Arg Ile Cys Pro Asn Asp Thr Gly Gly
                260                 265                 270

Leu Arg Ser Leu Val Asn Lys Trp Thr Thr Phe Leu Lys Ala Arg Leu
                275                 280                 285

Val Cys Ser Val Thr Asp Glu Asp Gly Pro Glu Thr His Phe Asp Glu
                290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Val Phe Lys Gly Ser Ala
                325                 330                 335

Val Cys Val Tyr His Leu Ser Asp Ile Gln Thr Val Phe Asn Gly Pro
                340                 345                 350

Phe Ala His Lys Glu Gly Pro Asn His Gln Leu Ile Ser Tyr Gln Gly
                355                 360                 365

Arg Ile Pro Tyr Pro Arg Pro Gly Thr Cys Pro Gly Gly Ala Phe Thr
                370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
                420                 425                 430

Ala Val Asp Arg Val Asn Ala Ala Asp Gly Arg Tyr His Val Leu Phe
                435                 440                 445

Leu Gly Thr Asp Arg Gly Thr Val Gln Lys Val Val Leu Pro Thr
                450                 455                 460

Asn Asn Ser Val Ser Gly Glu Leu Ile Leu Glu Leu Glu Val Phe
465                 470                 475                 480

Lys Asn His Ala Pro Ile Thr Thr Met Lys Ile Ser Ser Lys Lys Gln
                485                 490                 495

Gln Leu Tyr Val Ser Ser Asn Glu Gly Val Ser Gln Val Ser Leu His
                500                 505                 510

Arg Cys His Ile Tyr Gly Thr Ala Cys Ala Asp Cys Cys Leu Ala Arg
                515                 520                 525

Asp Pro Tyr Cys Ala Trp Asp Gly His Ser Cys Ser Arg Phe Tyr Pro
                530                 535                 540

Thr Gly Lys Arg Lys Ser Lys Lys Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
                580                 585                 590

Ala Pro Lys Ser Pro Gln Ala Ser Ile Lys Trp Leu Leu Gln Lys Asp
                595                 600                 605

Lys Asp Arg Arg Lys Glu Val Lys Leu Asn Glu Arg Ile Ile Ala Thr
610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Val Thr Asp
                660                 665                 670
```

```
Lys Trp Ser Pro Trp Thr Trp Ala Ser Ser Val Arg Ala Leu Pro Phe
            675                 680                 685

His Pro Lys Asp Ile Met Gly Ala Phe Ser His Ser Glu Met Gln Met
        690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Leu Glu Ser Arg Gly Pro Phe Glu Gln Lys Leu Ile Ser Glu
            740                 745                 750

Glu Asp Leu Asn Met His Thr Gly His His His His His
            755                 760                 765

<210> SEQ ID NO 10
<211> LENGTH: 751
<212> TYPE: PRT
<213> ORGANISM: Homo sapiens

<400> SEQUENCE: 10

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
```

```
            275                 280                 285
Val Cys Ser Val Thr Asp Glu Asp Gly Pro Glu Thr His Phe Asp Glu
            290                 295                 300
Leu Glu Asp Val Phe Leu Leu Glu Thr Asp Asn Pro Arg Thr Thr Leu
305                 310                 315                 320
Val Tyr Gly Ile Phe Thr Thr Ser Ser Ser Val Phe Lys Gly Ser Ala
                    325                 330                 335
Val Cys Val Tyr His Leu Ser Asp Ile Gln Thr Val Phe Asn Gly Pro
                340                 345                 350
Phe Ala His Lys Glu Gly Pro Asn His Gln Leu Ile Ser Tyr Gln Gly
            355                 360                 365
Arg Ile Pro Tyr Pro Arg Pro Gly Thr Cys Pro Gly Gly Ala Phe Thr
        370                 375                 380
Pro Asn Met Arg Thr Thr Lys Glu Phe Pro Asp Asp Val Val Thr Phe
385                 390                 395                 400
Ile Arg Asn His Pro Leu Met Tyr Asn Ser Ile Tyr Pro Ile His Lys
                    405                 410                 415
Arg Pro Leu Ile Val Arg Ile Gly Thr Asp Tyr Lys Tyr Thr Lys Ile
                420                 425                 430
Ala Val Asp Arg Val Asn Ala Ala Asp Gly Arg Tyr His Val Leu Phe
            435                 440                 445
Leu Gly Thr Asp Arg Gly Thr Val Gln Lys Val Val Leu Pro Thr
        450                 455                 460
Asn Asn Ser Val Ser Gly Glu Leu Ile Leu Glu Glu Leu Glu Val Phe
465                 470                 475                 480
Lys Asn His Ala Pro Ile Thr Thr Met Lys Ile Ser Ser Lys Lys Gln
                    485                 490                 495
Gln Leu Tyr Val Ser Ser Asn Glu Gly Val Ser Gln Val Ser Leu His
                500                 505                 510
Arg Cys His Ile Tyr Gly Thr Ala Cys Ala Asp Cys Cys Leu Ala Arg
            515                 520                 525
Asp Pro Tyr Cys Ala Trp Asp Gly His Ser Cys Ser Arg Phe Tyr Pro
        530                 535                 540
Thr Gly Lys Arg Lys Ser Lys Lys Gln Asp Val Arg His Gly Asn Pro
545                 550                 555                 560
Leu Thr Gln Cys Arg Gly Phe Asn Leu Lys Ala Tyr Arg Asn Ala Ala
                    565                 570                 575
Glu Ile Val Gln Tyr Gly Val Lys Asn Asn Thr Thr Phe Leu Glu Cys
                580                 585                 590
Ala Pro Lys Ser Pro Gln Ala Ser Ile Lys Trp Leu Leu Gln Lys Asp
            595                 600                 605
Lys Asp Arg Arg Lys Glu Val Lys Leu Asn Glu Arg Ile Ile Ala Thr
        610                 615                 620
Ser Gln Gly Leu Leu Ile Arg Ser Val Gln Gly Ser Asp Gln Gly Leu
625                 630                 635                 640
Tyr His Cys Ile Ala Thr Glu Asn Ser Phe Lys Gln Thr Ile Ala Lys
                    645                 650                 655
Ile Asn Phe Lys Val Leu Asp Ser Glu Met Val Ala Val Thr Asp
                660                 665                 670
Lys Trp Ser Pro Trp Thr Trp Ala Ser Ser Val Arg Ala Leu Pro Phe
            675                 680                 685
His Pro Lys Asp Ile Met Gly Ala Phe Ser His Ser Glu Met Gln Met
        690                 695                 700
```

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
            725                 730                 735

Asn Ser Arg Lys Ser Arg Asn Arg Arg Asn Gln Leu Pro Glu Ser
        740                 745                 750

<210> SEQ ID NO 11
<211> LENGTH: 4
<212> TYPE: PRT
<213> ORGANISM: Homo sapiens

<400> SEQUENCE: 11

Arg Ser Lys Arg
1

<210> SEQ ID NO 12
<211> LENGTH: 4
<212> TYPE: PRT
<213> ORGANISM: Homo sapiens

<400> SEQUENCE: 12

Lys Ser Lys Arg
1

<210> SEQ ID NO 13
<211> LENGTH: 4
<212> TYPE: PRT
<213> ORGANISM: Homo sapiens

<400> SEQUENCE: 13

Lys Ser Lys Lys
1

<210> SEQ ID NO 14
<211> LENGTH: 980
<212> TYPE: PRT
<213> ORGANISM: Homo sapiens

<400> SEQUENCE: 14

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu

```
        145                 150                 155                 160
Ser Gly Lys Gly Arg Cys Ser Phe Asn Pro Asn Val Asn Thr Val Ser
                    165                 170                 175
Val Met Ile Asn Glu Glu Leu Phe Ser Gly Met Tyr Ile Asp Phe Met
                    180                 185                 190
Gly Thr Asp Ala Ala Ile Phe Arg Ser Leu Thr Lys Arg Asn Ala Val
                    195                 200                 205
Arg Thr Asp Gln His Asn Ser Lys Trp Leu Ser Glu Pro Met Phe Val
                    210                 215                 220
Asp Ala His Val Ile Pro Asp Gly Thr Asp Pro Asn Asp Ala Lys Val
225                 230                 235                 240
Tyr Phe Phe Phe Lys Glu Lys Leu Thr Asp Asn Arg Ser Thr Lys
                    245                 250                 255
Gln Ile His Ser Met Ile Ala Arg Ile Cys Pro Asn Asp Thr Gly Gly
                    260                 265                 270
Leu Arg Ser Leu Val Asn Lys Trp Thr Thr Phe Leu Lys Ala Arg Leu
                    275                 280                 285
Val Cys Ser Val Thr Asp Glu Asp Gly Pro Glu Thr His Phe Asp Glu
                    290                 295                 300
Leu Glu Asp Val Phe Leu Leu Glu Thr Asp Asn Pro Arg Thr Thr Leu
305                 310                 315                 320
Val Tyr Gly Ile Phe Thr Thr Ser Ser Val Phe Lys Gly Ser Ala
                    325                 330                 335
Val Cys Val Tyr His Leu Ser Asp Ile Gln Thr Val Phe Asn Gly Pro
                    340                 345                 350
Phe Ala His Lys Glu Gly Pro Asn His Gln Leu Ile Ser Tyr Gln Gly
                    355                 360                 365
Arg Ile Pro Tyr Pro Arg Pro Gly Thr Cys Pro Gly Gly Ala Phe Thr
                    370                 375                 380
Pro Asn Met Arg Thr Thr Lys Glu Phe Pro Asp Asp Val Val Thr Phe
385                 390                 395                 400
Ile Arg Asn His Pro Leu Met Tyr Asn Ser Ile Tyr Pro Ile His Lys
                    405                 410                 415
Arg Pro Leu Ile Val Arg Ile Gly Thr Asp Tyr Lys Tyr Thr Lys Ile
                    420                 425                 430
Ala Val Asp Arg Val Asn Ala Ala Asp Gly Arg Tyr His Val Leu Phe
                    435                 440                 445
Leu Gly Thr Asp Arg Gly Thr Val Gln Lys Val Val Leu Pro Thr
450                 455                 460
Asn Asn Ser Val Ser Gly Glu Leu Ile Leu Glu Glu Leu Glu Val Phe
465                 470                 475                 480
Lys Asn His Ala Pro Ile Thr Thr Met Lys Ile Ser Ser Lys Lys Gln
                    485                 490                 495
Gln Leu Tyr Val Ser Ser Asn Glu Gly Val Ser Gln Val Ser Leu His
                    500                 505                 510
Arg Cys His Ile Tyr Gly Thr Ala Cys Ala Asp Cys Cys Leu Ala Arg
                    515                 520                 525
Asp Pro Tyr Cys Ala Trp Asp Gly His Ser Cys Ser Arg Phe Tyr Pro
                    530                 535                 540
Thr Gly Lys Arg Arg Ser Arg Arg Gln Asp Val Arg His Gly Asn Pro
545                 550                 555                 560
Leu Thr Gln Cys Arg Gly Phe Asn Leu Lys Ala Tyr Arg Asn Ala Ala
                    565                 570                 575
```

```
Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
        595                 600                 605

Lys Asp Arg Arg Lys Glu Val Lys Leu Asn Glu Arg Ile Ile Ala Thr
    610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Val Thr Asp
            660                 665                 670

Lys Trp Ser Pro Trp Thr Trp Ala Ser Ser Val Arg Ala Leu Pro Phe
        675                 680                 685

His Pro Lys Asp Ile Met Gly Ala Phe Ser His Ser Glu Met Gln Met
    690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Arg Lys Ser Arg Asn Arg Arg Asn Gln Leu Pro Glu Ser Leu
            740                 745                 750

Glu Asp Lys Thr His Thr Cys Pro Pro Cys Pro Ala Pro Glu Leu Leu
        755                 760                 765

Gly Gly Pro Ser Val Phe Leu Phe Pro Pro Lys Pro Lys Asp Thr Leu
    770                 775                 780

Met Ile Ser Arg Thr Pro Glu Val Thr Cys Val Val Val Asp Val Ser
785                 790                 795                 800

His Glu Asp Pro Glu Val Lys Phe Asn Trp Tyr Val Asp Gly Val Glu
                805                 810                 815

Val His Asn Ala Lys Thr Lys Pro Arg Glu Glu Gln Tyr Asn Ser Thr
            820                 825                 830

Tyr Arg Val Val Ser Val Leu Thr Val Leu His Gln Asp Trp Leu Asn
        835                 840                 845

Gly Lys Glu Tyr Lys Cys Lys Val Ser Asn Lys Ala Leu Pro Ala Pro
    850                 855                 860

Ile Glu Lys Thr Ile Ser Lys Ala Lys Gly Gln Pro Arg Glu Pro Gln
865                 870                 875                 880

Val Tyr Thr Leu Pro Pro Ser Arg Glu Glu Met Thr Lys Asn Gln Val
                885                 890                 895

Ser Leu Thr Cys Leu Val Lys Gly Phe Tyr Pro Ser Asp Ile Ala Val
            900                 905                 910

Glu Trp Glu Ser Asn Gly Gln Pro Glu Asn Asn Tyr Lys Thr Thr Pro
        915                 920                 925

Pro Val Leu Asp Ser Asp Gly Ser Phe Phe Leu Tyr Ser Lys Leu Thr
    930                 935                 940

Val Asp Lys Ser Arg Trp Gln Gln Gly Asn Val Phe Ser Cys Ser Val
945                 950                 955                 960

Met His Glu Ala Leu His Asn His Tyr Thr Gln Lys Ser Leu Ser Leu
                965                 970                 975

Ser Pro Gly Lys
            980
```

<210> SEQ ID NO 15
<211> LENGTH: 2256
<212> TYPE: DNA
<213> ORGANISM: Homo sapiens

<400> SEQUENCE: 15

| | | | | | |
|---|---|---|---|---|---|
| atggcattcc | ggacaatttg | cgtgttggtt | ggagtattta | tttgttctat | ctgtgtgaaa | 60
| ggatcttccc | agccccaagc | aagagtttat | ttaacatttg | atgaacttcg | agaaaccaag | 120
| acctctgaat | acttcagcct | ttcccaccat | cctttagact | acaggatttt | attaatggat | 180
| gaagatcagg | accggatata | tgtgggaagc | aaagatcaca | ttctttccct | gaatattaac | 240
| aatataagtc | aagaagcttt | gagtgttttc | tggccagcat | ctacaatcaa | agttgaagaa | 300
| tgcaaaatgg | ctggcaaaga | tcccacacac | ggctgtggga | actttgtccg | tgtaattcag | 360
| actttcaatc | gcacacattt | gtatgtctgt | gggagtggcg | ctttcagtcc | tgtctgtact | 420
| tacttgaaca | gagggaggag | atcagaggac | caagttttca | tgattgactc | caagtgtgaa | 480
| tctggaaaag | gacgctgctc | tttcaacccc | aacgtgaaca | cggtgtctgt | tatgatcaat | 540
| gaggagcttt | tctctggaat | gtatatagat | ttcatgggga | cagatgctgc | tattttcga | 600
| agtttaacca | gaggaatgc | ggtcagaact | gatcaacata | attccaaatg | gctaagtgaa | 660
| cctatgtttg | tagatgcaca | tgtcatccca | gatggtactg | atccaaatga | tgctaaggtg | 720
| tacttcttct | tcaaagaaaa | actgactgac | aataacagga | gcacgaaaca | gattcattcc | 780
| atgattgctc | gaatatgtcc | taatgacact | ggtggactgc | gtagccttgt | caacaagtgg | 840
| accactttct | taaaggcgag | gctggtgtgc | tcggtaacag | atgaagacgg | cccagaaaca | 900
| cactttgatg | aattagagga | tgtgtttctg | ctggaaactg | ataacccgag | gacaacacta | 960
| gtgtatggca | ttttacaac | atcaagctca | gttttcaaag | gatcagccgt | gtgtgtgtat | 1020
| catttatctg | atatacagac | tgtgtttaat | gggccttttg | cccacaaaga | agggcccaat | 1080
| catcagctga | tttcctatca | gggcagaatt | ccatatcctc | gccctggaac | ttgtccagga | 1140
| ggagcattta | cacccaatat | gcgaaccacc | aaggagttcc | cagatgatgt | tgtcactttt | 1200
| attcggaacc | atcctctcat | gtacaattcc | atctacccaa | tccacaaaag | gcctttgatt | 1260
| gttcgtattg | gcactgacta | caagtataca | aagatagctg | tggatcgagt | gaacgctgct | 1320
| gatgggagat | accatgtcct | gtttctcgga | acagatcggg | gtactgtgca | aaaagtggtt | 1380
| gttcttccta | ctaacaactc | tgtcagtggc | gagctcattc | tggaggagct | ggaagtcttt | 1440
| aagaatcatg | ctcctataac | aacaatgaaa | atttcatcta | aaaagcaaca | gttgtatgtg | 1500
| agttccaatg | aaggggtttc | ccaggtatct | ctgcaccgct | gccacatcta | tggtacagcc | 1560
| tgtgctgact | gctgcctggc | gcgggaccct | tattgcgcct | gggatggcca | ttcctgttcc | 1620
| agattctacc | caactgggaa | acggaggagc | cgaagacaag | atgtgagaca | tggaaaccca | 1680
| ctgactcaat | gcagaggatt | taatctaaaa | gcatacagaa | atgcagctga | aattgtgcag | 1740
| tatggagtaa | aaaataacac | cacttttctg | gagtgtgccc | ccaagtctcc | gcaggcatct | 1800
| atcaagtggc | tgttacagaa | agacaaagac | aggaggaaag | aggttaagct | gaatgaacga | 1860
| ataatagcca | cttcacaggg | actcctgatc | cgctctgttc | agggttctga | ccaaggactt | 1920
| tatcactgca | ttgctacaga | aaatagtttc | aagcagacca | tagccaagat | caacttcaaa | 1980
| gttttagatt | cagaaatggt | ggctgttgtg | acgacaaat | ggtccccatg | gacctgggcc | 2040
| agctctgtga | gggctttacc | cttccacccg | aaggacatca | tggggcatt | cagccactca | 2100
| gaaatgcaga | tgattaacca | atattgcaaa | gacactcggc | agcaacatca | gcaggagat | 2160

```
gaatcacaga aaatgagagg ggactatggc aagttaaagg ccctcatcaa tagtcggaaa    2220
agtagaaaca ggaggaatca gttgccagag tcataa                              2256

<210> SEQ ID NO 16
<211> LENGTH: 12
<212> TYPE: DNA
<213> ORGANISM: Homo sapiens

<400> SEQUENCE: 16
agagggagga ga                                                          12

<210> SEQ ID NO 17
<211> LENGTH: 12
<212> TYPE: DNA
<213> ORGANISM: Homo sapiens

<400> SEQUENCE: 17
aggagccgaa ga                                                          12

<210> SEQ ID NO 18
<211> LENGTH: 12
<212> TYPE: DNA
<213> ORGANISM: Homo sapiens

<400> SEQUENCE: 18
agaaacagga gg                                                          12

<210> SEQ ID NO 19
<211> LENGTH: 66
<212> TYPE: DNA
<213> ORGANISM: Homo sapiens

<400> SEQUENCE: 19
aaaatgagag gggactatgg caagttaaag gccctcatca atagtcggaa aagtagaaac      60
aggagg                                                                 66

<210> SEQ ID NO 20
<211> LENGTH: 1644
<212> TYPE: DNA
<213> ORGANISM: Homo sapiens

<400> SEQUENCE: 20
atggcattcc ggacaatttg cgtgttggtt ggagtattta tttgttctat ctgtgtgaaa      60
ggatcttccc agccccaagc aagagtttat ttaacatttg atgaacttcg agaaaccaag     120
acctctgaat acttcagcct ttcccaccat cctttagact acaggatttt attaatggat     180
gaagatcagg accggatata tgtgggaagc aaagatcaca ttctttccct gaatattaac     240
aatataagtc aagaagcttt gagtgttttc tggccagcat ctacaatcaa agttgaagaa     300
tgcaaaatgg ctggcaaaga tcccacacac ggctgtggga ctttgtccg tgtaattcag     360 actttcaatc gcacacattt gtatgtctgt gggagtggcg ctttcagtcc tgtctgtact     420
tacttgaaca gagggaggag atcagaggac caagttttca tgattgactc caagtgtgaa     480
tctggaaaag gacgctgctc tttcaacccc aacgtgaaca cggtgtctgt tatgatcaat     540
gaggagcttt tctctggaat gtatatagat ttcatgggga cagatgctgc tatttttcga     600
agtttaacca agaggaatgc ggtcagaact gatcaacata attccaaatg ctaagtgaa     660 cctatgtttg tagatgcaca tgtcatccca gatggtactg atccaaatga tgctaaggtg     720
```

| | |
|---|---|
| tacttcttct tcaaagaaaa actgactgac aataacagga gcacgaaaca gattcattcc | 780 |
| atgattgctc gaatatgtcc taatgacact ggtggactgc gtagccttgt caacaagtgg | 840 |
| accactttct taaaggcgag gctggtgtgc tcggtaacag atgaagacgg cccagaaaca | 900 |
| cactttgatg aattagagga tgtgtttctg ctggaaactg ataacccgag acaacacta | 960 |
| gtgtatggca tttttacaac atcaagctca gttttcaaag gatcagccgt gtgtgtgtat | 1020 |
| catttatctg atatacagac tgtgtttaat gggccttttg cccacaaaga agggcccaat | 1080 |
| catcagctga tttcctatca gggcagaatt ccatatcctc gccctggaac ttgtccagga | 1140 |
| ggagcattta cacccaatat gcgaaccacc aaggagttcc cagatgatgt tgtcactttt | 1200 |
| attcggaacc atcctctcat gtacaattcc atctacccaa tccacaaaag gcctttgatt | 1260 |
| gttcgtattg cactgactac aagtataca aagatagctg tggatcgagt gaacgctgct | 1320 |
| gatgggagat accatgtcct gtttctcgga acagatcggg gtactgtgca aaaagtggtt | 1380 |
| gttcttccta ctaacaactc tgtcagtggc gagctcattc tggaggagct ggaagtcttt | 1440 |
| aagaatcatg ctcctataac aacaatgaaa atttcatcta aaaagcaaca gttgtatgtg | 1500 |
| agttccaatg aaggggtttc ccaggtatct ctgcaccgct gccacatcta tggtacagcc | 1560 |
| tgtgctgact gctgcctggc gcgggaccct tattgcgcct gggatggcca ttcctgttcc | 1620 |
| agattctacc caactgggaa acgg | 1644 |

<210> SEQ ID NO 21
<211> LENGTH: 2334
<212> TYPE: DNA
<213> ORGANISM: Homo sapiens

<400> SEQUENCE: 21

| | |
|---|---|
| atggcattcc ggacaatttg cgtgttggtt ggagtattta tttgttctat ctgtgtgaaa | 60 |
| ggatcttccc agccccaagc aagagtttat ttaacatttg atgaacttcg agaaaccaag | 120 |
| acctctgaat acttcagcct ttcccaccat cctttagact acaggatttt attaatggat | 180 |
| gaagatcagg accggatata tgtgggaagc aaagatcaca ttctttccct gaatattaac | 240 |
| aatataagtc aagaagcttt gagtgttttc tggccagcat ctacaatcaa agttgaagaa | 300 |
| tgcaaaatgg ctggcaaaga tcccacacac ggctgtggga ctttgtccg tgtaattcag | 360 |
| actttcaatc gcacacattt gtatgtctgt gggagtggcg cttcagtcc tgtctgtact | 420 |
| tacttgaaca gagggaggag atcagaggac caagttttca tgattgactc caagtgtgaa | 480 |
| tctggaaaag gacgctgctc tttcaacccc aacgtgaaca cggtgtctgt tatgatcaat | 540 |
| gaggagcttt tctctggaat gtatatagat ttcatgggga cagatgctgc tattttttcga | 600 |
| agtttaacca agaggaatgc ggtcagaact gatcaacata attccaaatg gctaagtgaa | 660 |
| cctatgtttg tagatgcaca tgtcatccca gatggtactg atccaaatga tgctaaggtg | 720 |
| tacttcttct tcaaagaaaa actgactgac aataacagga gcacgaaaca gattcattcc | 780 |
| atgattgctc gaatatgtcc taatgacact ggtggactgc gtagccttgt caacaagtgg | 840 |
| accactttct taaaggcgag gctggtgtgc tcggtaacag atgaagacgg cccagaaaca | 900 |
| cactttgatg aattagagga tgtgtttctg ctggaaactg ataacccgag acaacacta | 960 |
| gtgtatggca tttttacaac atcaagctca gttttcaaag gatcagccgt gtgtgtgtat | 1020 |
| catttatctg atatacagac tgtgtttaat gggccttttg cccacaaaga agggcccaat | 1080 |
| catcagctga tttcctatca gggcagaatt ccatatcctc gccctggaac ttgtccagga | 1140 |
| ggagcattta cacccaatat gcgaaccacc aaggagttcc cagatgatgt tgtcactttt | 1200 |

| | |
|---|---|
| attcggaacc atcctctcat gtacaattcc atctacccaa tccacaaaag gcctttgatt | 1260 |
| gttcgtattg gcactgacta caagtataca aagatagctg tggatcgagt gaacgctgct | 1320 |
| gatgggagat accatgtcct gtttctcgga acagatcggg gtactgtgca aaaagtggtt | 1380 |
| gttcttccta ctaacaactc tgtcagtggc gagctcattc tggaggagct ggaagtcttt | 1440 |
| aagaatcatg ctcctataac aacaatgaaa atttcatcta aaaagcaaca gttgtatgtg | 1500 |
| agttccaatg aaggggtttc ccaggtatct ctgcaccgct gccacatcta tggtacagcc | 1560 |
| tgtgctgact gctgcctggc gcgggaccct tattgcgcct gggatggcca ttcctgttcc | 1620 |
| agattctacc caactgggaa acggctcgag gacaaaactc acacatgccc accgtgccca | 1680 |
| gcacctgaac tcctgggggg accgtcagtc ttcctcttcc ccccaaaacc caaggacacc | 1740 |
| ctcatgatct cccggacccc tgaggtcaca tgcgtggtgg tggacgtgag ccacgaagac | 1800 |
| cctgaggtca gttcaactg gtacgtggac ggcgtggagg tgcataatgc caagacaaag | 1860 |
| ccgcgggagg agcagtacaa cagcacgtac cgtgtggtca gcgtcctcac cgtcctgcac | 1920 |
| caggactggc tgaatggcaa ggagtacaag tgcaaggtct ccaacaaagc cctcccagcc | 1980 |
| cccatcgaga aaaccatctc caaagccaaa gggcagcccc gagaaccaca ggtgtacacc | 2040 |
| ctgcccccat cccgggagga gatgaccaag aaccaggtca gcctgacctg cctggtcaaa | 2100 |
| ggcttctatc ccagcgacat cgccgtggag tgggagagca atgggcagcc ggagaacaac | 2160 |
| tacaagacca cgcctcccgt gctggactcc gacggctcct tcttcctcta tagcaagctc | 2220 |
| accgtggaca agagcaggtg gcagcagggg aacgtcttct catgctccgt gatgcatgag | 2280 |
| gctctgcaca accactacac gcagaagagc ctctccctgt ccccgggtaa atga | 2334 |

<210> SEQ ID NO 22
<211> LENGTH: 2904
<212> TYPE: DNA
<213> ORGANISM: Homo sapiens

<400> SEQUENCE: 22

| | |
|---|---|
| atggcattcc ggacaatttg cgtgttggtt ggagtattta tttgttctat ctgtgtgaaa | 60 |
| ggatcttccc agccccaagc aagagtttat ttaacatttg atgaacttcg agaaaccaag | 120 |
| acctctgaat acttcagcct ttcccaccat cctttagact acaggatttt attaatggat | 180 |
| gaagatcagg accggatata tgtgggaagc aaagatcaca ttctttccct gaatattaac | 240 |
| aatataagtc aagaagcttt gagtgttttc tggccagcat ctacaatcaa agttgaagaa | 300 |
| tgcaaaatgg ctggcaaaga tcccacacac ggctgtggga ctttgtccg tgtaattcag | 360 |
| actttcaatc gcacacattt gtatgtctgt gggagtggcg ctttcagtcc tgtctgtact | 420 |
| tacttgaaca gagggaggag atcagaggac caagttttca tgattgactc caagtgtgaa | 480 |
| tctggaaaag gacgctgctc tttcaacccc aacgtgaaca cggtgtctgt tatgatcaat | 540 |
| gaggagcttt ctctggaat gtatatagat ttcatgggga cagatgctgc tattttttcga | 600 |
| agtttaacca agaggaatgc ggtcagaact gatcaacata attccaaatg gctaagtgaa | 660 |
| cctatgtttg tagatgcaca tgtcatccca gatggtactg atccaaatga tgctaaggtg | 720 |
| tacttcttct tcaaagaaaa actgactgac aataacagga gcacgaaaca gattcattcc | 780 |
| atgattgctc gaatatgtcc taatgacact ggtggactgc gtagccttgt caacaagtgg | 840 |
| accactttct taaggcgag gctggtgtgc tcggtaacag atgaagacgg cccagaaaca | 900 |
| cactttgatg aattagagga tgtgtttctg ctggaaactg ataaccccga gacaacacta | 960 |

| | |
|---|---|
| gtgtatggca ttttacaac atcaagctca gttttcaaag gatcagccgt gtgtgtgtat | 1020 |
| catttatctg atatacagac tgtgtttaat gggccttttg cccacaaaga agggcccaat | 1080 |
| catcagctga tttcctatca gggcagaatt ccatatcctc gccctggaac ttgtccagga | 1140 |
| ggagcattta cacccaatat gcgaaccacc aaggagttcc cagatgatgt tgtcactttt | 1200 |
| attcggaacc atcctctcat gtacaattcc atctacccaa tccacaaaag gcctttgatt | 1260 |
| gttcgtattg cactgactac aagtataca aagatagctg tggatcgagt gaacgctgct | 1320 |
| gatgggagat accatgtcct gtttctcgga acagatcggg gtactgtgca aaaagtggtt | 1380 |
| gttcttccta ctaacaactc tgtcagtggc gagctcattc tggaggagct ggaagtcttt | 1440 |
| aagaatcatg ctcctataac aacaatgaaa atttcatcta aaaagcaaca gttgtatgtg | 1500 |
| agttccaatg aaggggtttc ccaggtatct ctgcaccgct gccacatcta tggtacagcc | 1560 |
| tgtgctgact gctgcctggc gcgggaccct tattgcgcct gggatggcca ttcctgttcc | 1620 |
| agattctacc caactgggaa acggaagagc aaaaaacaag atgtgagaca tggaaaccca | 1680 |
| ctgactcaat gcagaggatt taatctaaaa gcatacagaa atgcagctga aattgtgcag | 1740 |
| tatggagtaa aaataacac cacttttctg gagtgtgccc ccaagtctcc gcaggcatct | 1800 |
| atcaagtggc tgttacagaa agacaaagac aggaggaaag aggttaagct gaatgaacga | 1860 |
| ataatagcca cttcacaggg actcctgatc cgctctgttc agggttctga ccaaggactt | 1920 |
| tatcactgca ttgctacaga aaatagtttc aagcagacca tagccaagat caacttcaaa | 1980 |
| gttttagatt cagaaatggt ggctgttgtg acggacaaat ggtccccatg gacctgggcc | 2040 |
| agctctgtga gggctttacc cttccacccg aaggacatca tggggcatt cagccactca | 2100 |
| gaaatgcaga tgattaacca atattgcaaa gacactcggc agcaacatca gcagggagat | 2160 |
| gaatcacaga aaatgagagg ggactatggc aagttaaagg ccctcatcaa tagtctcgag | 2220 |
| gacaaaactc acacatgccc accgtgccca gcacctgaac tcctggggg accgtcagtc | 2280 |
| ttcctcttcc ccccaaaacc caaggacacc ctcatgatct cccggacccc tgaggtcaca | 2340 |
| tgcgtggtgg tggacgtgag ccacgaagac cctgaggtca agttcaactg gtacgtggac | 2400 |
| ggcgtggagg tgcataatgc caagacaaag ccgcgggagg agcagtacaa cagcacgtac | 2460 |
| cgtgtggtca gcgtcctcac cgtcctgcac caggactggc tgaatggcaa ggagtacaag | 2520 |
| tgcaaggtct ccaacaaagc cctcccagcc cccatcgaga aaaccatctc caaagccaaa | 2580 |
| gggcagcccc gagaaccaca ggtgtacacc ctgcccccat cccgggagga gatgaccaag | 2640 |
| aaccaggtca gcctgacctg cctggtcaaa ggcttctatc ccagcgacat cgccgtggag | 2700 |
| tgggagagca atgggcagcc ggagaacaac tacaagacca cgcctcccgt gctggactcc | 2760 |
| gacggctcct tcttcctcta tagcaagctc accgtggaca agagcaggtg gcagcagggg | 2820 |
| aacgtcttct catgctccgt gatgcatgag gctctgcaca accactacac gcagaagagc | 2880 |
| ctctccctgt ccccgggtaa atga | 2904 |

<210> SEQ ID NO 23
<211> LENGTH: 2301
<212> TYPE: DNA
<213> ORGANISM: Homo sapiens

<400> SEQUENCE: 23

| | |
|---|---|
| atggcattcc ggacaatttg cgtgttggtt ggagtattta tttgttctat ctgtgtgaaa | 60 |
| ggatcttccc agccccaagc aagagtttat ttaacatttg atgaacttcg agaaaccaag | 120 |
| acctctgaat acttcagcct ttcccaccat cctttagact acaggatttt attaatggat | 180 |

```
gaagatcagg accggatata tgtgggaagc aaagatcaca ttctttccct gaatattaac      240
aatataagtc aagaagcttt gagtgttttc tggccagcat ctacaatcaa agttgaagaa      300
tgcaaaatgg ctggcaaaga tcccacacac ggctgtggga actttgtccg tgtaattcag      360
actttcaatc gcacacattt gtatgtctgt gggagtggcg ctttcagtcc tgtctgtact      420
tacttgaaca gagggaggag atcagaggac caagttttca tgattgactc caagtgtgaa      480
tctgaaaaag gacgctgctc tttcaacccc aacgtgaaca cggtgtctgt tatgatcaat      540
gaggagcttt tctctggaat gtatatagat ttcatgggga cagatgctgc tattttcga       600 agtttaacca agaggaatgc ggtcagaact gatcaacata attccaaatg ctaagtgaa       660 cctatgtttg tagatgcaca tgtcatccca gatggtactg atccaaatga tgctaaggtg      720
tacttcttct tcaaagaaaa actgactgac aataacagga gcacgaaaca gattcattcc      780
atgattgctc gaatatgtcc taatgacact ggtggactgc gtagccttgt caacaagtgg      840
accactttct taaaggcgag gctggtgtgc tcggtaacag atgaagacgg cccagaaaca      900
cactttgatg aattagagga tgtgtttctg ctggaaactg ataacccgag acaacacta       960 gtgtatggca ttttttacaac atcaagctca gttttcaaag gatcagccgt gtgtgtgtat     1020
catttatctg atatacagac tgtgtttaat gggccttttg cccacaaaga agggcccaat     1080
catcagctga tttcctatca gggcagaatt ccatatcctc gccctggaac ttgtccagga     1140
ggagcattta cacccaatat gcgaaccacc aaggagttcc cagatgatgt tgtcactttt     1200
attcggaacc atcctctcat gtacaattcc atctacccaa tccacaaaag gcctttgatt     1260
gttcgtattg gcactgacta caagtataca aagatagctg tggatcgagt gaacgctgct     1320
gatgggagat accatgtcct gtttctcgga acagatcggg gtactgtgca aaaagtggtt     1380
gttcttccta ctaacaactc tgtcagtggc gagctcattc tggaggagct ggaagtctt     1440 aagaatcatg ctcctataac aacaatgaaa atttcatcta aaaagcaaca gttgtatgtg     1500
agttccaatg aaggggtttc ccaggtatct ctgcaccgct gccacatcta tggtacagcc     1560
tgtgctgact gctgcctggc gcgggaccct tattgcgcct gggatggcca ttcctgttcc     1620
agattctacc caactgggaa acggaagagc aaaaaacaag atgtgagaca tggaaaccca     1680
ctgactcaat gcagaggatt taatctaaaa gcatacagaa atgcagctga aattgtgcag     1740
tatggagtaa aaataacac cacttttctg gagtgtgccc ccaagtctcc gcaggcatct     1800
atcaagtggc tgttacagaa agacaaagac aggaggaaag aggttaagct gaatgaacga     1860
ataatagcca cttcacaggg actcctgatc cgctctgttc agggttctga ccaaggactt     1920
tatcactgca ttgctacaga aaatagtttc aagcagacca tagccaagat caacttcaaa     1980
gttttagatt cagaaatggt ggctgttgtg acggacaaat ggtccccatg gacctgggcc     2040
agctctgtga gggctttacc cttccacccg aaggacatca tgggggcatt cagccactca     2100
gaaatgcaga tgattaacca atattgcaaa gacactcggc agcaacatca gcagggagat     2160
gaatcacaga aaatgagagg ggactatggc aagttaaagg ccctcatcaa tagtctcgag     2220
tctagagggc ccttcgaaca aaaactcatc tcagaagagg atctgaatat gcataccggt     2280
catcatcacc atcaccattg a                                                2301

<210> SEQ ID NO 24
<211> LENGTH: 38
<212> TYPE: DNA
<213> ORGANISM: Homo sapiens
```

```
<400> SEQUENCE: 24
gggaaacgga ggagcaaaag acaagatgtg agacatgg                              38

<210> SEQ ID NO 25
<211> LENGTH: 38
<212> TYPE: DNA
<213> ORGANISM: Homo sapiens

<400> SEQUENCE: 25
ccatgtctca catcttgtct tttgctcctc cgtttccc                              38

<210> SEQ ID NO 26
<211> LENGTH: 47
<212> TYPE: DNA
<213> ORGANISM: Homo sapiens

<400> SEQUENCE: 26
tacccaactg ggaaacggaa gagcaaaaga caagatgtga gacatgg                    47

<210> SEQ ID NO 27
<211> LENGTH: 47
<212> TYPE: DNA
<213> ORGANISM: Homo sapiens

<400> SEQUENCE: 27
ccatgtctca catcttgtct tttgctcttc cgtttcccag ttgggta                    47

<210> SEQ ID NO 28
<211> LENGTH: 44
<212> TYPE: DNA
<213> ORGANISM: Homo sapiens

<400> SEQUENCE: 28
gggaaacgga agagcaaaaa acaagatgtg agacatggaa accc                       44

<210> SEQ ID NO 29
<211> LENGTH: 44
<212> TYPE: DNA
<213> ORGANISM: Homo sapiens

<400> SEQUENCE: 29
gggtttccat gtctcacatc ttgtttttttg ctcttccgtt tccc                      44

<210> SEQ ID NO 30
<211> LENGTH: 29
<212> TYPE: DNA
<213> ORGANISM: Homo sapiens

<400> SEQUENCE: 30
cgggatccac catggcatcg gacaatttg                                        29

<210> SEQ ID NO 31
<211> LENGTH: 32
<212> TYPE: DNA
<213> ORGANISM: Homo sapiens

<400> SEQUENCE: 31
cgctcgagac tattgatgag ggcctttaac tt                                    32

<210> SEQ ID NO 32
<211> LENGTH: 42
<212> TYPE: DNA
<213> ORGANISM: Homo sapiens
```

<400> SEQUENCE: 32
cggaaaagta gaaacaggag gaatcagttg ccagagtcat aa                    42

<210> SEQ ID NO 33
<211> LENGTH: 738
<212> TYPE: PRT
<213> ORGANISM: Homo sapiens

<400> SEQUENCE: 33

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350

Phe Ala His Lys Glu Gly Pro Asn His Gln Leu Ile Ser Tyr Gln Gly
            355                 360                 365

Arg Ile Pro Tyr Pro Arg Pro Gly Thr Cys Pro Gly Gly Ala Phe Thr
370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
            405                 410                 415

Arg Pro Leu Ile Val Arg Ile Gly Thr Asp Tyr Lys Tyr Thr Lys Ile
            420                 425                 430

Ala Val Asp Arg Val Asn Ala Ala Asp Gly Arg Tyr His Val Leu Phe
            435                 440                 445

Leu Gly Thr Asp Arg Gly Thr Val Gln Lys Val Val Val Leu Pro Thr
            450                 455                 460

Asn Asn Ser Val Ser Gly Glu Leu Ile Leu Glu Glu Leu Glu Val Phe
465                 470                 475                 480

Lys Asn His Ala Pro Ile Thr Thr Met Lys Ile Ser Ser Lys Lys Gln
            485                 490                 495

Gln Leu Tyr Val Ser Ser Asn Glu Gly Val Ser Gln Val Ser Leu His
            500                 505                 510

Arg Cys His Ile Tyr Gly Thr Ala Cys Ala Asp Cys Cys Leu Ala Arg
            515                 520                 525

Asp Pro Tyr Cys Ala Trp Asp Gly His Ser Cys Ser Arg Phe Tyr Pro
            530                 535                 540

Thr Gly Lys Arg Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
            565                 570                 575

Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
            595                 600                 605

Lys Asp Arg Arg Lys Glu Val Lys Leu Asn Glu Arg Ile Ile Ala Thr
610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
            645                 650                 655

Ile Asn Phe Lys Val Leu Asp Ser Glu Met Val Ala Val Val Thr Asp
            660                 665                 670

Lys Trp Ser Pro Trp Thr Trp Ala Ser Ser Val Arg Ala Leu Pro Phe
            675                 680                 685

His Pro Lys Asp Ile Met Gly Ala Phe Ser His Ser Glu Met Gln Met
            690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
            725                 730                 735

Asn Ser

<210> SEQ ID NO 34
<211> LENGTH: 13
<212> TYPE: PRT
<213> ORGANISM: Homo sapiens

```
<400> SEQUENCE: 34

Arg Lys Ser Arg Asn Arg Arg Asn Gln Leu Pro Glu Ser
1               5                   10

<210> SEQ ID NO 35
<211> LENGTH: 738
<212> TYPE: PRT
<213> ORGANISM: Homo sapiens

<400> SEQUENCE: 35

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
            100                 105                 110

Gly Asn Phe Val Arg Val Ile Gln Thr Phe Asn Arg Thr His Leu Tyr
        115                 120                 125

Val Cys Gly Ser Gly Ala Phe Ser Pro Val Cys Thr Tyr Leu Asn Arg
    130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
            180                 185                 190

Gly Thr Asp Ala Ala Ile Phe Arg Ser Leu Thr Lys Arg Asn Ala Val
        195                 200                 205

Arg Thr Asp Gln His Asn Ser Lys Trp Leu Ser Glu Pro Met Phe Val
    210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
            260                 265                 270

Leu Arg Ser Leu Val Asn Lys Trp Thr Thr Phe Leu Lys Ala Arg Leu
        275                 280                 285

Val Cys Ser Val Thr Asp Glu Asp Gly Pro Glu Thr His Phe Asp Glu
    290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
            340                 345                 350
```

-continued

Phe Ala His Lys Glu Gly Pro Asn His Gln Leu Ile Ser Tyr Gln Gly
            355                 360                 365
Arg Ile Pro Tyr Pro Arg Pro Gly Thr Cys Pro Gly Gly Ala Phe Thr
    370                 375                 380
Pro Asn Met Arg Thr Thr Lys Glu Phe Pro Asp Asp Val Val Thr Phe
385                 390                 395                 400
Ile Arg Asn His Pro Leu Met Tyr Asn Ser Ile Tyr Pro Ile His Lys
                405                 410                 415
Arg Pro Leu Ile Val Arg Ile Gly Thr Asp Tyr Lys Tyr Thr Lys Ile
            420                 425                 430
Ala Val Asp Arg Val Asn Ala Ala Asp Gly Arg Tyr His Val Leu Phe
        435                 440                 445
Leu Gly Thr Asp Arg Gly Thr Val Gln Lys Val Val Leu Pro Thr
    450                 455                 460
Asn Asn Ser Val Ser Gly Glu Leu Ile Leu Glu Glu Leu Glu Val Phe
465                 470                 475                 480
Lys Asn His Ala Pro Ile Thr Thr Met Lys Ile Ser Ser Lys Lys Gln
                485                 490                 495
Gln Leu Tyr Val Ser Ser Asn Glu Gly Val Ser Gln Val Ser Leu His
            500                 505                 510
Arg Cys His Ile Tyr Gly Thr Ala Cys Ala Asp Cys Cys Leu Ala Arg
        515                 520                 525
Asp Pro Tyr Cys Ala Trp Asp Gly His Ser Cys Ser Arg Phe Tyr Pro
    530                 535                 540
Thr Gly Lys Arg Lys Ser Lys Lys Gln Asp Val Arg His Gly Asn Pro
545                 550                 555                 560
Leu Thr Gln Cys Arg Gly Phe Asn Leu Lys Ala Tyr Arg Asn Ala Ala
                565                 570                 575
Glu Ile Val Gln Tyr Gly Val Lys Asn Asn Thr Thr Phe Leu Glu Cys
            580                 585                 590
Ala Pro Lys Ser Pro Gln Ala Ser Ile Lys Trp Leu Leu Gln Lys Asp
        595                 600                 605
Lys Asp Arg Arg Lys Glu Val Lys Leu Asn Glu Arg Ile Ile Ala Thr
    610                 615                 620
Ser Gln Gly Leu Leu Ile Arg Ser Val Gln Gly Ser Asp Gln Gly Leu
625                 630                 635                 640
Tyr His Cys Ile Ala Thr Glu Asn Ser Phe Lys Gln Thr Ile Ala Lys
                645                 650                 655
Ile Asn Phe Lys Val Leu Asp Ser Glu Met Val Ala Val Thr Asp
            660                 665                 670
Lys Trp Ser Pro Trp Thr Trp Ala Ser Ser Val Arg Ala Leu Pro Phe
        675                 680                 685
His Pro Lys Asp Ile Met Gly Ala Phe Ser His Ser Glu Met Gln Met
    690                 695                 700
Ile Asn Gln Tyr Cys Lys Asp Thr Arg Gln Gln His Gln Gln Gly Asp
705                 710                 715                 720
Glu Ser Gln Lys Met Arg Gly Asp Tyr Gly Lys Leu Lys Ala Leu Ile
                725                 730                 735
Asn Ser

<210> SEQ ID NO 36
<211> LENGTH: 10
<212> TYPE: PRT

```
<213> ORGANISM: Homo sapiens

<400> SEQUENCE: 36

Arg Asn Arg Arg Asn Gln Leu Pro Glu Ser
1               5                   10
```